US010000809B2

(12) United States Patent
Keshavjee et al.

(10) Patent No.: US 10,000,809 B2
(45) Date of Patent: Jun. 19, 2018

(54) METHODS FOR DETERMINING RISK OF CHRONIC LUNG ALLOGRAFT DYSFUNCTION (CLAD) AND SUBTYPES THEREOF

(71) Applicant: University Health Network, Toronto (CA)

(72) Inventors: Shaf Keshavjee, Toronto (CA); Mingyao Liu, North York (CA); Marcelo Cypel, Toronto (CA)

(73) Assignee: University Health Network, Toronto (CA)

( * ) Notice: Subject to any disclaimer, the term of this patent is extended or adjusted under 35 U.S.C. 154(b) by 0 days. days.

(21) Appl. No.: 14/769,425

(22) PCT Filed: Feb. 20, 2014

(86) PCT No.: PCT/CA2014/000139
§ 371 (c)(1),
(2) Date: Aug. 20, 2015

(87) PCT Pub. No.: WO2014/127463
PCT Pub. Date: Aug. 28, 2014

(65) Prior Publication Data
US 2016/0002726 A1 Jan. 7, 2016

Related U.S. Application Data

(60) Provisional application No. 61/766,894, filed on Feb. 20, 2013.

(51) Int. Cl.
*G01N 33/68* (2006.01)
*C12Q 1/68* (2018.01)

(52) U.S. Cl.
CPC ....... *C12Q 1/6883* (2013.01); *G01N 33/6869* (2013.01); *C12Q 2600/112* (2013.01); *C12Q 2600/158* (2013.01); *G01N 2333/4727* (2013.01); *G01N 2333/5412* (2013.01); *G01N 2333/5428* (2013.01); *G01N 2800/245* (2013.01); *G01N 2800/50* (2013.01)

(58) Field of Classification Search
None
See application file for complete search history.

(56) References Cited

PUBLICATIONS

Kaneda et al, American Journal of Transplantation 2006; vol. 6, pp. 544-551.*
Tirkos et al, Respiratory Research, 2006, vol. 7, No. 51, pp. 1-11.*
Kosanam et al, Clinical Biochemistry, Dec. 14, 2011, vol. 45, pp. 223-230.*
McMorran et al reference, Clinical Chemistry, 2007, vol. 53, No. 10, pp. 1782-1791.*
Hubner et al, European Respiratory Journal, 2005, vol. 25, pp. 494-501.*
Vanaudenaerde et al. The Role of the IL23/IL17 Axis in Bronchiolitis Obliterans Syndrome After Lung Transplantation, The American Journal of Transplantation 2008, vol. 8, pp. 1911-1920.
Saito et al. Biologic Subtyping of Human Chronic Lung Allograft Dysfunction, The Journal of Heart and Lung Transplantation, vol. 31, No. 4S, Apr. 2012, pp. S124-S125.
Hodge et al. Posttransplant Bronchiolitis Obliterans Syndrome is Associated with Bronchial Epithelial to Mesenchymal Transition. American Journal of Transplantation 2009, vol. 9, pp. 727-733.
Saito, T. et al. Impact of cytokine expression in the pre-implanted donor lung on the development of chronic lung allograft dysfunction subtypes. American Journal of Transplantation, Dec. 2013, vol. 13, No. 12, pp. 3192-3201.
Kennedy, V. et al. Bronchoalveolar lavage as a tool to predict, diagnose and understood bronchiolitis obliterans syndrome. Am. J. Transplant, Mar. 2013, vol. 13, No. 2, pp. 552-561.
Quetant, S. et al. 181 Pulmonary transplantation and bronchiolitis obliterans syndrome: characterization of diagnostic biomarkers in bronchiolo-aveolar lavage fluid by SELDI-TOF proteomic analysis. 2009. Retrieved on Mar. 21, 2014 <http://www.ersnet.org/learning_resources_player/abstract_print_09/files/35.pdf>.
Chien, J. et al. Evaluation of published single nucleotide polymorphisms associated with acute GVHD. Blood, 2012, vol. 119, pp. 5311-5319.
Lu, K. et al. Interleukin-6 and interferon-gama gene polymorphisms in the development of bronchilitis obliterans syndrome after lung transplantation. Transplantation, 2002, vol. 74, No. 9, pp. 1297-1302.

(Continued)

*Primary Examiner* — Bridget E Bunner
*Assistant Examiner* — Fozia Hamud
(74) *Attorney, Agent, or Firm* — Bereskin & Parr LLP; Carmela De Luca

(57) ABSTRACT

Methods for assaying a donor lung for chronic allograft lung dysfunction (CLAD) optionally bronchiolitis obliterans syndrome (BOS) subtype or restrictive allograft syndrome (RAS) subtype of CLAD or risk of developing BOS subtype or RAS subtype CLAD post-transplant, the method comprising: a. measuring a normalized expression level of an RNA transcript of IL-6 or an expression product thereof in a sample of the donor lung pre-transplant or a normalized expression level of one or more S100 protein, optionally S100A8 and/or S100A9, polypeptide expression product in a sample from the donor lung post-transplant; b. assessing the likelihood of the donor lung developing BOS subtype CLAD or RAS subtype CLAD post-transplant based on said IL-6, S100, optionally S100A8 and/or S100A9, expression level wherein IL-6 expression level is positively correlated with an increased likelihood of developing BOS post-transplant, S100A8 expression level is positively correlated with having or having an increased likelihood of developing RAS and/or BOS subtype CLAD, and S100A9 is positively correlated with having and having an increased likelihood of developing RAS subtype CLAD.

12 Claims, 20 Drawing Sheets

(56) References Cited

PUBLICATIONS

Hall, D. et al. Immediate postoperative inflammatory response predicts long term outcome in lung-transplant recipients. Interactive Cardio Vascular and Thoracic Surgery, 2013, vol. 15, No. 4, pp. 603-607.

\* cited by examiner

S100A9 (MRP14) for
Differentiating RAS from BOS

AUC: 0.95 [0.85- 1.05]
p= 0.0045

S100A8 (MRP8) for
Differentiating CLAD from No CLAD

AUC: 0.89 [0.78- 1.01]
p= 0.0004

SEQUENCE LISTING

```
<160> NUMBER OF SEQ ID NOS: 14

<210> SEQ ID NO 1
<211> LENGTH: 20
<212> TYPE: DNA
<213> ORGANISM: Homo Sapiens

<400> SEQUENCE: 1
cacacagaca gccactcacc                                                   20

<210> SEQ ID NO 2
<211> LENGTH: 20
<212> TYPE: DNA
<213> ORGANISM: Homo Sapiens

<400> SEQUENCE: 2
ttttctgcca gtgcctcttt                                                   20

<210> SEQ ID NO 3
<211> LENGTH: 20
<212> TYPE: DNA
<213> ORGANISM: Homo Sapiens

<400> SEQUENCE: 3
ggacaagctg aggaagatgc                                                   20

<210> SEQ ID NO 4
<211> LENGTH: 20
<212> TYPE: DNA
<213> ORGANISM: Homo Sapiens

<400> SEQUENCE: 4
tcgttatccc atgtgtcgaa                                                   20
```

```
<210> SEQ ID NO 5
<211> LENGTH: 20
<212> TYPE: DNA
<213> ORGANISM: Homo Sapiens

<400> SEQUENCE: 5
caggaattga atgggtttgc                                               20

<210> SEQ ID NO 6
<211> LENGTH: 20
<212> TYPE: DNA
<213> ORGANISM: Homo Sapiens

<400> SEQUENCE: 6
agcagactag ggttgccaga                                               20

<210> SEQ ID NO 7
<211> LENGTH: 20
<212> TYPE: DNA
<213> ORGANISM: Homo Sapiens

<400> SEQUENCE: 7
aagcctgacc acgctttcta                                               20

<210> SEQ ID NO 8
<211> LENGTH: 20
<212> TYPE: DNA
<213> ORGANISM: Homo Sapiens

<400> SEQUENCE: 8
gctccctggt ttctcttcct                                               20

<210> SEQ ID NO 9
<211> LENGTH: 20
<212> TYPE: DNA
<213> ORGANISM: Homo Sapiens

<400> SEQUENCE: 9
gtccaacgca aagcaataca                                               20

<210> SEQ ID NO 10
<211> LENGTH: 20
<212> TYPE: DNA
<213> ORGANISM: Homo Sapiens

<400> SEQUENCE: 10
atattgcagg caggacaacc                                               20

<210> SEQ ID NO 11
<211> LENGTH: 20
<212> TYPE: DNA
<213> ORGANISM: Homo Sapiens

<400> SEQUENCE: 11
agcccatgtt gtagcaaacc                                               20

<210> SEQ ID NO 12
<211> LENGTH: 20
<212> TYPE: DNA
<213> ORGANISM: Homo Sapiens

<400> SEQUENCE: 12
tgaggtacag gccctctgat                                               20
```

```
<210> SEQ ID NO 13
<211> LENGTH: 20
<212> TYPE: DNA
<213> ORGANISM: Homo Sapiens

<400> SEQUENCE: 13 gtaaccgtt gaaccccatt                                          20

<210> SEQ ID NO 14
<211> LENGTH: 20
<212> TYPE: DNA
<213> ORGANISM: Homo Sapiens

<400> SEQUENCE: 14
ccatccaatc ggtagtagcg                                         20
```

METHODS FOR DETERMINING RISK OF CHRONIC LUNG ALLOGRAFT DYSFUNCTION (CLAD) AND SUBTYPES THEREOF

RELATED APPLICATIONS

This is a Patent Cooperation Treaty Application which claims the benefit of 35 U.S.C. § 119 based on the priority of U.S. Provisional Patent Application No. 61/766,894, filed Feb. 20, 2013 which is incorporated herein by reference in its entirety.

INCORPORATION OF SEQUENCE LISTING

A computer readable form of the Sequence Listing "P43473US01_ST25.txt" (2,339 bytes), submitted via EFS-WEB and created on Jun. 23, 2017, is herein incorporated by reference.

FIELD

The present disclosure relates to methods for assessing the likelihood of a lung transplant recipient developing chronic lung allograft dysfunction or a subtype thereof post-transplant.

BACKGROUND

Lung transplantation is lifesaving for patients with end-stage lung diseases. However, its long-term success continues to be challenged by chronic lung allograft dysfunction (CLAD) despite the improvement of the early survival[1]. CLAD, mainly recognized as bronchiolitis obliterans syndrome (BOS), is a major cause of morbidity and mortality in long-term survivors. CLAD affects about 50% of lung transplant recipients 5 years after lung transplantation[1]. No effective treatment has yet been established.

Recently, restrictive allograft syndrome (RAS) has been identified as a novel subtype of CLAD[10,11]. Since RAS and BOS (CLAD without RAS) show distinct clinical, radiological and pathological manifestations, it is suggested that development of these CLAD subtypes may involve distinct molecular pathways.

U.S. Pat. No. 8,247,175 (Keshavjee et al), describes that IL-6/IL-10 ratio measured in the donor lung before implantation significantly predicted recipient 30 day primary graft failure.

A differential proteomic analysis of BAL fluid from a small group of lung transplant patients with or without chronic graft dysfunction RAS subtype identified 30 proteins that were not present in BAL from non-CGD samples (18).

SUMMARY

An aspect includes a method for assaying a donor lung for bronchiolitis obliterans syndrome (BOS) subtype or restrictive allograft syndrome (RAS) subtype of chronic allograft lung dysfunction (CLAD) or risk of developing CLAD and/or developing BOS subtype or RAS subtype CLAD post-transplant, the method comprising:
a. measuring a normalized expression level of an RNA transcript of IL-6 or an expression product thereof in a sample of the donor lung pre-transplant or a normalized expression level of one or more S100A8, S100A8/A9, S100A9, S100A12, S100P and/or HMGB1, polypeptide expression product in a sample from the donor lung post-transplant;
b. assessing the likelihood of the donor lung of having and/or developing CLAD, BOS subtype CLAD or RAS subtype CLAD post-transplant based on said IL-6, S100A8 S100A8/A9, S100A9, S100A12, S100P and/or HMGB1, expression level wherein detecting increased IL-6 expression identifies an increased likelihood of developing BOS post-transplant, detecting an increased level of S100A8, S100A8/A9, S1009, S10012, S100P and/or HMGB1 expression identifies an increased likelihood of having and/or developing CLAD (RAS and/or BOS subtype CLAD), and/or detecting an increased level of S100A9, S100A8/A9, S10012, S100P and/or HMGB1 identifies an increased likelihood of having and/or developing RAS subtype CLAD.

In an embodiment, the normalized expression of level of IL-6 transcript or an expression product thereof is measured.

In an embodiment, the normalized expression level of the RNA transcription of IL-6 or the expression product thereof is measured, the method further comprising:
a. measuring a normalized expression level of an RNA transcript of IL-10 or an expression product thereof in a sample from the donor lung pre-transplant;
b. calculating an IL-6/1L-10 expression level ratio; and
c. assessing the likelihood of the donor lung developing BOS subtype CLAD post-transplant based on said IL-6/IL-10 expression level ratio wherein said ratio is positively correlated with an increased likelihood of developing BOS subtype CLAD post-transplant.

In an embodiment, a normalized expression level of S100A8, S100A9, S100A8/A9 and S100A12 polypeptide expression product in a sample from the donor lung post-transplant is measured and a subject with an increased level of S100A8 S100A9, S100A8/A9 and S100A12 compared to a control is assessed as having or having an increased likelihood of developing CLAD, e.g. RAS and/or BOS subtype CLAD.

In an embodiment, a normalized expression level of S100A8 polypeptide expression product in a sample from the donor lung post-transplant is measured and a subject with an increased level of S100A8 compared to a control is assessed as having or having an increased likelihood of developing CLAD, e.g. RAS and/or BOS subtype CLAD.

In an embodiment, a normalized expression level of S100A9, S100A8/A9, S100A12 and HMGB1 polypeptide expression product in a sample from the donor lung post-transplant is measured and a subject with an increased level of S100A9, S100A8/A9 S100A12 and HMGB1 compared to a control is assessed as having or having an increased likelihood of developing RAS type CLAD.

In an embodiment, a normalized expression level of S100A9, S100A8/A9, S100A12 and/or HMGB1 polypeptide expression product in a sample from the donor lung post-transplant is measured and a subject with an increased level of S100A9, S100A8/A9, S100A12 and/or HMGB1 compared to a control is assessed as having or having an increased likelihood of developing RAS subtype CLAD.

In an embodiment, the sample from the donor lung is a bronchoalveolar lavage (BAL) sample. In another embodiment, the sample is a post-transplant lung biopsy, such as a transbronchial lung biopsy (TBB) and/or a combination thereof.

A further aspect includes a method for assaying a donor lung for risk of developing bronchiolitis obliterans syndrome (BOS) subtype of chronic allograft lung dysfunction (CLAD) post-transplant, the method comprising:
  a. measuring a normalized expression level of an RNA transcript of IL-6 or an expression product thereof in a sample from the donor lung pre-transplant;
  b. predicting the likelihood of the donor lung developing BOS subtype CLAD post-transplant based on said IL-6 expression level wherein said IL-6 expression level is positively correlated with an increased likelihood of developing BOS subtype CLAD post-transplant.

In an embodiment, a normalized expression level of the RNA transcription of IL-6 or the expression product thereof is measured, the method further comprising:
  a. measuring a normalized expression level of an RNA transcript of IL-10 or an expression product thereof in a sample from the donor lung pre-transplant;
  b. calculating an IL-6/1L-10 expression level ratio; and
  c. predicting the likelihood of the donor lung developing BOS subtype CLAD post-transplant based on said IL-6/IL-10 expression level ratio wherein said ratio is positively correlated with an increased likelihood of developing BOS subtype CLAD post-transplant.

A further aspect includes a method for assaying a donor lung for risk of developing bronchiolitis obliterans syndrome (BOS) subtype of chronic allograft lung dysfunction (CLAD) post-transplant, the method comprising:
  a. measuring a normalized expression level of an RNA transcript of IL-6 or an expression product thereof and measuring a normalized expression level of an RNA transcript of IL-10 or an expression product thereof in a sample from the donor lung pre-transplant;
  b. calculating an IL-6/1L-10 expression level ratio; and
  c. predicting the likelihood of the donor lung developing BOS subtype CLAD post-transplant based on said IL-6/IL-10 expression level ratio wherein said ratio is positively correlated with an increased likelihood of developing BOS subtype CLAD post-transplant.

In an embodiment, predicting the likelihood comprises comparing the IL-6/IL-10 expression level ratio with a control ratio determined from levels in control lung samples.

A further aspect includes, method to identify a donor lung that has decreased risk of bronchiolitis obliterans syndrome (BOS) subtype chronic allograft lung dysfunction (CLAD) post-transplant, the method comprising:
  a. measuring a normalized expression level of an RNA transcript of IL-6 or an expression product thereof and measuring a normalized expression level of an RNA transcript of IL-10 or an expression product thereof in a sample from the donor lung;
  b. calculating an IL-6/IL-10 expression level ratio; and
  c. identifying the donor lung as one with a decreased risk of developing BOS subtype CLAD post-transplant if said IL-6/IL-10 expression level ratio is lower in the sample than a control ratio determined from levels from control lung samples.

Yet a further aspect includes a method to identify a donor lung that has increased risk of bronchiolitis obliterans syndrome (BOS) subtype CLAD, the method comprising:
  a. measuring a normalized expression level of an RNA transcript of IL-10 or an expression product thereof and measuring a normalized expression level of an RNA transcript of IL-6 or an expression product thereof in a sample from the donor lung;
  b. calculating an IL-6/IL-10 expression level ratio; and
  c. identifying the donor lung as one with an increased risk of developing BOS subtype CLAD post-transplant based on said IL-6/IL-10 expression level ratio wherein said ratio is positively correlated with an increased likelihood of developing BOS subtype CLAD.

In an embodiment, the method further comprising selecting the donor lung with a risk of developing BOS subtype CLAD or RAS subtype CLAD below a desired risk level for transplant.

A further aspect includes a method of selecting a donor lung for transplant, the method comprising:
  a. measuring a normalized expression level of an RNA transcript of IL-6 or an expression product thereof, in a sample of the donor lung pre-transplant;
  b. predicting the risk of the donor lung developing BOS subtype CLAD or RAS subtype CLAD post-transplant based on said IL-6, wherein IL-6 expression level is positively correlated with an increased likelihood of developing BOS post-transplant; and
  c. selecting the donor lung for transplant if the risk of developing BOS subtype CLAD or RAS subtype CLAD is below a desired risk level.

In an embodiment, a normalized expression level of the RNA transcription of IL-6 or the expression product thereof is measured, the method further comprising:
  a. measuring a normalized expression level of an RNA transcript of IL-10 or an expression product thereof in a sample from the donor lung pre-transplant;
  b. calculating an IL-6/1L-10 expression level ratio; and
  c. predicting the likelihood of the donor lung developing BOS subtype CLAD post-transplant based on said IL-6/IL-10 expression level ratio wherein said ratio is positively correlated with an increased likelihood of developing BOS subtype CLAD post-transplant.

In an embodiment, the method comprises first obtaining a sample of the donor lung (such as a biopsy) or a BAL sample from the donor lung for measuring the normalized expression levels.

In an embodiment, the expression level ratio is calculated according to the formula log normalized IL-6 expression level/log normalized IL-10 expression level.

In an embodiment, the expression level and/or expression level ratio is associated with early onset BOS or early onset RAS.

In an embodiment, the donor lung is identified to be one with an increased risk of early BOS subtype CLAD development when the IL-6/IL-10 ratio is greater than 0.78.

In an embodiment, the donor lung is identified to be one with an increased risk of early RAS subtype CLAD development when the IL-6/IL-10 ratio is less than or equal to 1.175.

In an embodiment, the donor lung is identified to be one with an increased risk of early CLAD when the IL6/IL-10 ratio is greater than 0.78 and less than 1.175 or greater than 1.175. In yet another embodiment, the donor lung is identified to be one with an increased risk of early allograft loss when the when the IL6/IL-10 ratio is greater than 0.78 and less than 1.175.

In an embodiment, the prediction/identification comprising pre-transplant expression levels further comprises assessing one or more of diffuse alveolar damage (DAD), acute rejection CMV mismatch and late new onset DAD.

In an embodiment, the level of RNA transcript is measured by quantitative real time PCR.

A further aspect includes a method for assaying a donor lung as having BOS subtype and/or RAS subtype CLAD post-transplant, the method comprising:
  a. measuring a normalized expression level of S100A8, S100A9, S100A8/A9, S100A12 and/or HMGB1, polypeptide expression product in a BAL sample from the donor lung post-transplant;

b. determining an increased expression of S100A8, S100A9, S100A8/A9 and/or S100A12 compound to a CLAD threshold and/or detecting an increased expression of S100A9, S100A8/A9, S100A12 and/or HMGB1 compared to a RAS threshold; and c. identifying the donor lung with increased S100A8, S100A9, S100A8/A9 and/or S100A12 expression level compound to the CLAD threshold as having or having an increased likelihood of developing CLAD, RAS and/or BOS subtype CLAD, and/or identifying the donor lung with increased S100A9, S100A8/A9, S100A12 and/or HMGB1 expression level compared to RAS threshold as having or having an increased likelihood of developing RAS subtype CLAD.

In an embodiment, the level of S100A9 in BAL identifying the donor lung as having or having an increased likelihood of developing CLAD and/or RAS subtype CLAD (e.g. RAS threshold) is greater than at least 18 ng/mL, at least 20 ng/mL, at least 22 ng/mL, at least 24 ng/mL, at least 26 ng/mL, at least 28 ng/mL, at least 30 ng/mL, at least 32 ng/mL, at least 34 ng/mL, at least 36 ng/mL, at least 38 ng/mL, at least 40 ng/mL, at least 42 ng/mL, at least 44 ng/mL, at least 46 ng/mL, at least 48 ng/mL, at least 50 ng/mL, at least 52 ng/mL, at least 54 ng/mL, at least 56 ng/mL or at least 58 ng/mL.

In an embodiment, the level of S100A8/A9 identifying the donor lung as having or having an increased likelihood of developing RAS subtype CLAD is greater than at least 3 ng/mL, at least 3.5 ng/mL, at least 4 ng/mL, at least 5 ng/mL, at least 6 ng/mL, at least 7 ng/mL, at least 8 ng/mL, at least 9 ng/mL and at least 10 ng/mL.

In an embodiment, the level of S100A12 in BAL identifying the donor lung as having or having an increased likelihood of developing CLAD and/or RAS subtype CLAD is greater than at least 150 ng/mL, at least 160 ng/mL, at least 170 ng/mL, at least 180 ng/mL, at least 190 ng/mL, at least 200 ng/mL, at least 210 ng/mL, at least 220 ng/mL, at least 230 ng/mL, at least 240 ng/mL and at least 250 ng/mL.

In an embodiment, the level of S100A12 identifying the donor lung as having or having an increased likelihood of developing CLAD, is greater than at least 35 ng/mL, at least 40 ng/mL, at least 50 ng/mL, at least 55 ng/mL, at least 60 ng/mL.

In another embodiment, the level of S100A8 in BAL identifying the donor lung as having or having an increased likelihood of developing BOS subtype CLAD is greater than about 28 ng/mL, about 30 ng/mL, about 32 ng/mL, about 34 ng/mL, about 36 ng/mL, about 38 ng/mL, about 40 ng/mL, about 32 ng/mL, about 34 ng/mL or about 36 ng/mL and less than about 200 ng/mL, about 250 ng/mL, about 300 ng/mL, and/or about 350 ng/mL.

In yet a further embodiment, the level of S100A8 identifying the donor lung as having or having an increased likelihood of developing RAS subtype CLAD is greater than about 200 ng/mL.

In another embodiment, the level of S100A12 in BAL identifying the donor lung as having or having an increased likelihood of developing BOS subtype CLAD is greater than about 30 ng/mL, about 35 ng/mL, about 40 ng/mL, about 45 ng/mL and/or 50 ng/mL and less than about 190 ng/mL, about 180 ng/mL, about 170 ng/mL and/or 160 ng/mL.

In an embodiment, the level of HMGB1, in BAL identifying the donor lung as having or having an increased likelihood of developing RAS type CLAD is at least 10 ng/mL, at least 12 ng/mL, at least 15 ng/mL, at least 17.5 ng/mL, and/or at least 20 ng/mL.

In an embodiment, the level of polypeptide expression product is measured by immunoassay. In an embodiment, the immunoassay is an ELISA.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

An embodiment of the present disclosure will now be described in relation to the drawings in which:

FIG. 6A shows S100A9 and S100A8 and FIG. 6B shows S100P and S100A12.

FIGS. 9A, 9C and 9D, illustrate that S100A8, S100A8/A9 and S100A12 showed higher expressions in RAS and BOS compared with No CLAD (p<0.0001, p<0.0001 and p<0.0001 for S100A8, S100A8/A9 and S100A12 between RAS and No CLAD; p=0.0006, p=0.0044 and p=0.0086 for S100A8, S100A8/A9 and S100A12 between BOS and No CLAD, respectively). Up-regulation of S100A8/A9 and S100A12 were significantly greater in RAS compared to BOS (p=0.038 and p=0.041, respectively). Furthermore, expression levels of S100A9, S100P and HMGB1 shown in FIGS. 9B, 9E and 9F were higher in RAS compared to BOS as well as No CLAD (p=0.0094, p=0.035 and p=0.0062 for S100A9, S100P and HMGB1 between RAS and BOS; p<0.0001, p<0.0001 and p<0.0001 for S100A9, S100P and HMGB1 between RAS and No CLAD, respectively). sRAGE (FIG. 9G) did not show any statistically significant difference (p=0.174 among RAS, BOS and No CLAD). Adjusted p-values are: *p<0.05, p<0.01, *p<0.001 and ****p<0.0001. BOS, bronchiolitis obliterans syndrome; CLAD, chronic lung allograft dysfunction; HMGB1, high-mobility box group 1; RAS, restrictive allograft syndrome; sRAGE, soluble receptor for advanced glycation endproducts;

FIG. 10A shows that 0 out of 169 potential study participants, 109 patients were included in this study. By the end of the observation period, the development of CLAD was observed in 71 patients, of which 50 were diagnosed with BOS and 21 with RAS. FIG. 10B shows that five- and ten-year survival rates were 62.4% and 43.8%, respectively. FIG. 10C shows survival curves according to CLAD phenotypes demonstrated five-year survival rate of 68.4% in No CLAD, 66.0% in BOS and 42.9% in RAS. RAS group showed lower survival rate compared to No CLAD and BOS (adjusted p-value=0.008 and 0.029, respectively). Although BOS group did not show a significant difference in survival rate compared to No CLAD (adjusted p-value=0.795), early-onset BOS showed significantly worse survival rate than No CLAD (adjusted p-value=0.005). FIG. 10D shows that CLAD-free survival rates were 42.7% and 25.6%, respectively. BOS, bronchiolitis obliterans syndrome; CLAD, chronic lung allograft dysfunction; $FEV_1$, forced expiratory volume in one second; RAS, restrictive allograft syndrome; TLC, total lung capacity.

FIG. 12 shows the cumulative incidence of CLAD was higher in patients comprising the top quartile compared to those in the bottom quartile. $^†$p-value=0.021 in Quartile 4 vs. Quartile 1. FIG. 12B shows that the cumulative incidence of BOS was higher in patients comprising the top quartile compared to those in the bottom and lower middle quartiles. $^‡$p-value=0.002 in Quartile4 vs. Quartile 1 and $^\#$p-value=0.016 in Quartile4 vs. Quartile 2. FIG. 12C shows the cumulative incidence of RAS in patients comprising the lower middle quartile tended to be higher compared to those in the upper middle, but it did not reach statistical significance (p=0.081).

DETAILED DESCRIPTION OF THE DISCLOSURE

I. Definitions

Figure 1:
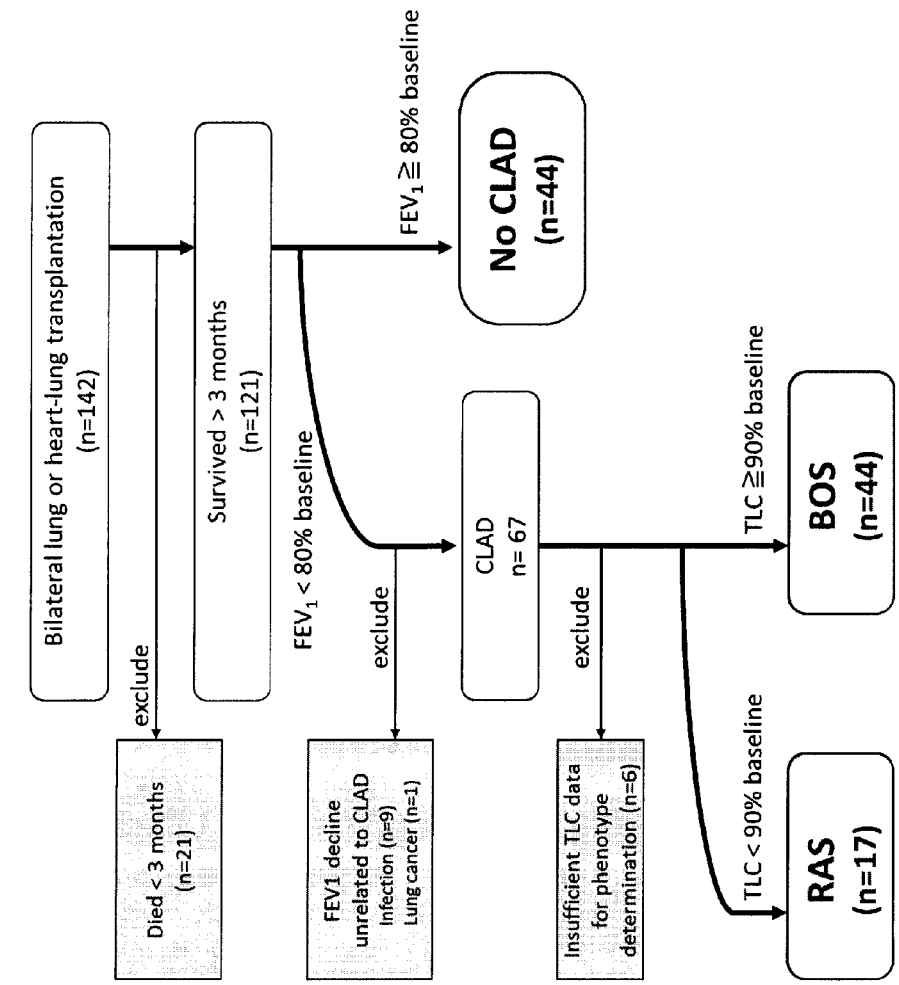
FIG. 1: Overview of separation of patients (All lungs were retrieved from DBD).

The term "antibody" as used herein is intended to include monoclonal antibodies, polyclonal antibodies, and chimeric antibodies. The antibody may be from recombinant sources and/or produced in transgenic animals. Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, dsFv, ds-scFv, dimers, minibodies, diabodies, bispecific antibody fragments and other fragments can also be synthesized by recombinant techniques. Antibody fragments mean binding fragments.

Antibodies having specificity for a specific protein, such as the protein product of a biomarker of the disclosure, may be prepared by conventional methods. A mammal (e.g. a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g. the hybridoma technique originally developed by Kohler and Milstein (Nature 256:495-497 (1975)) as well as other techniques such as the human B-cell hybridoma technique (Kozbor et al., Immunol. Today 4:72 (1983)), the EBV-hybridoma technique to produce human monoclonal antibodies (Cole et al., Methods Enzymol, 121: 140-67 (1986)), and screening of combinatorial antibody libraries (Huse et al., Science 246:1275 (1989)). Hybridoma cells can be screened immunochemically for production of antibodies specifically reactive with the peptide and the monoclonal antibodies can be isolated.

The term "CLAD" or "chronic lung allograft dysfunction" as used herein means for example a subject or lung with an irreversible decline in forced expiratory volume in one second (FEV$_1$) below 80% of baseline total lung capacity. Two subtypes of CLAD have been identified bronchiolitis obliterans syndrome (BOS) and restrictive allograft syndrome (RAS) subtypes.

The term "BOS subtype of CLAD" as used herein means for example CLAD without restrictive RAS. Bronchiolitis obliterans syndrome shows relatively slow progression with minimal interstitial infiltration.

The term "early-onset BOS" or "early BOS" or "early BOS subtype CLAD" as used herein means for example BOS subtype of CLAD which develops within three years after lung transplant.

The term "RAS subtype of CLAD" as used herein means for example CLAD with an irreversible decline in TLC below 90% of baseline. RAS accounts for approximately 30% of chronic allograft dysfunction. Restrictive allograft syndrome is a rapidly progressive disease with short survival time after its onset, showing radiological characteristics of interstitial lung disease.

The term "detection agent" refers to an agent that selectively binds and is capable of binding its cognate biomarker compared to another molecule and which can be used to detect a level and/or the presence of the biomarker. A biomarker specific detection agent can include probes, primers and the like as well as binding polypeptides such as antibodies which can for example be used with immunohistochemistry (IHC), ELISA, immunofluorescence, radioimmunoassay, dot blotting, FACS and protein microarray to detect the expression level of a biomarker described herein. Similarly, "an antibody or fragment thereof" (e.g. binding fragment), that specifically binds a biomarker refers to an antibody or fragment that selectively binds its cognate biomarker compared to another molecule. "Selective" is used contextually, to characterize the binding properties of an antibody. An antibody that binds specifically or selectively to a given biomarker or epitope thereof will bind to that biomarker and/or epitope either with greater avidity or with more specificity, relative to other, different molecules. For example, the antibody can bind 3-5, 5-7, 7-10, 10-15, 5-15, or 5-30 fold more efficiently to its cognate biomarker compared to another molecule. The "detection agent" can for example be coupled to or labeled with a detectable marker. The label is preferably capable of producing, either directly or indirectly, a detectable signal. For example, the label may be radio-opaque or a radioisotope, such as $^3$H, $^{14}$C, $^{32}$P, $^{35}$S, $^{123}$I, $^{125}$I, $^{131}$I; a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion.

The term "control" to a sample (e.g. control sample) from (e.g. lung sample) or derived from a donor lung (e.g. BAL fluid) or a group of individuals (e.g. standardized control) who are known as no CLAD, BOS subtype CLAD or RAS subtype CLAD or a value derived therefrom (e.g. control value such as a cut off value or threshold) above and/or below which identifies a test donor lung as more likely a CLAD subtype and/or more likely to develop CLAD or no CLAD. For example, the control can be a value that corresponds to the median level of the biomarker in a set of samples from no CLAD, BOS subtype CLAD or RAS subtype CLAD known outcome subjects. The control level can for example be a range of values and biomarker levels can be compared to a single control value, to a range of control values, to the upper level of normal, or to the lower level of normal as appropriate for the assay. The standardized control can for example be predetermined using an average of the levels of expression of one or more biomarkers from a population of subjects having no CLAD, CLAD, BOS and/or RAS subtype.

The term "sample" as used herein can include a lung sample such as biopsy and/or a fluid derived from a lung such as bronchoalveolar lavage (BAL) fluid and/or any lung cell or lung biological fluid suitable for protein and/or transcript analysis.

The term "CLAD threshold" refers to a value derived from a plurality of samples of donor lungs for a biomarker polypeptide selected from S100A8, S100A9, S100A8/A9, S100A12, S100P, HMGB1 and/or any other marker described herein, above which threshold is associated with an increased likelihood of having and/or developing CLAD.

The term "RAS threshold" refers to a value derived from the plurality of donor lungs corresponding to a biomarker polypeptide selected from S100A8, S100A9, S100A8/A9, S100A12, S100P, HMGB1 and/or any other marker described herein, above which indicates the donor lung is more likely to have and/or develop RAS subtype CLAD.

As used herein, "changed as compared to a control" sample or subject is understood as having a level of the analyte or diagnostic or therapeutic indicator (e.g., marker) to be detected at a level that is statistically different than a sample from a normal, untreated, or abnormal state control sample. Determination of statistical significance is within the ability of those skilled in the art, e.g., the number of standard deviations from the mean that constitute a positive or negative result.

As used herein, "one or more" is understood as each value 1, 2, 3, 4, 5, 6, 7, 8, 9, 10, and any value greater than 10.

The term "hybridize" refers to the sequence specific non-covalent binding interaction with a complementary nucleic acid. In a preferred embodiment, the hybridization is under high stringency conditions. Appropriate stringency conditions which promote hybridization are known to those skilled in the art, or can be found in Current Protocols in Molecular Biology, John Wiley & Sons, N.Y. (1989), 6.3.1-6.3.6. For example, 6.0× sodium chloride/sodium citrate (SSC) at about 45° C., followed by a wash of 2.0×SSC at 50° C. may be employed.

The term "IL-6" or "interleukin-6" as used herein includes all know IL-6 molecules including human, naturally occurring variants and those deposited in Genbank, for example, with accession number AAH15511, each of which is herein incorporated by reference.

The term "IL-10" or "interleukin-10" as used herein includes all know IL-10 molecules including human, naturally occurring variants and those deposited in Genbank, for example, with accession number CAG46825, each of which is herein incorporated by reference.

The term "level" as used herein refers to an amount (e.g. relative amount or concentration) of biomarker (e.g. IL-6, IL-10, S100A8 or S100A9) that is detectable, measurable or quantifiable in a test biological sample and/or a reference biological sample. For example, the level can be a concentration such as μg/L or ng/L, or a relative amount such as 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 10, 15, 20, 25, and/or 30 times more or less than a control biomarker level. The control biomarker polypeptide level, can for example, be the average or median level in a plurality of control samples (e.g. donor lung or BAL fluid samples).

The term "normalized expression" as used herein means a set of protein and/or RNA transcript values measured on different scales and adjusted to a notionally common scale. For example normalized expression can be relative to 18S ribosomal RNA, and/or one or more housekeeping gene.

The term "isolated nucleic acid sequence" as used herein refers to a nucleic acid substantially free of cellular material or culture medium when produced by recombinant DNA techniques, or chemical precursors, or other chemicals when chemically synthesized. An "isolated nucleic acid" is also substantially free of sequences which naturally flank the nucleic acid (i.e. sequences located at the 5' and 3' ends of the nucleic acid) from which the nucleic acid is derived. The term "nucleic acid" is intended to include DNA and RNA and can be either double stranded or single stranded.

The term "primer" as used herein refers to a nucleic acid sequence, whether occurring naturally as in a purified restriction digest or produced synthetically, which is capable of acting as a point of synthesis of when placed under conditions in which synthesis of a primer extension product, which is complementary to a nucleic acid strand is induced (e.g. in the presence of nucleotides and an inducing agent such as DNA polymerase and at a suitable temperature and pH). The primer must be sufficiently long to prime the synthesis of the desired extension product in the presence of the inducing agent. The exact length of the primer will depend upon factors, including temperature, sequences of the primer and the methods used. A primer typically contains 15-25 or more nucleotides, although it can contain less. The factors involved in determining the appropriate length of primer are readily known to one of ordinary skill in the art.

The term "probe" as used herein refers to a nucleic acid sequence that will hybridize to a nucleic acid target sequence. In one example, the probe hybridizes to an RNA transcript or a nucleic acid sequence complementary to the RNA transcript to be detected. The length of probe depends on the hybridize conditions and the sequences of the probe and nucleic acid target sequence. In one embodiment, the probe is at least 8, 10, 15, 20, 25, 50, 75, 100, 150, 200, 250, 400, 500 or more nucleotides in length.

The term "S100A8" as used herein means a family member of the S100 calcium binding proteins and includes all know S100A8 molecules including human, naturally occurring variants and those deposited in Genbank, for example, with accession number CAG28602, each of which is herein incorporated by reference.

The term "S100A9" as used herein means a family member of the S100 calcium binding proteins and includes all know S100A9 molecules including human, naturally occurring variants and those deposited in Genbank, for example, with accession number CAG47020, each of which is herein incorporated by reference.

The term "S100A8/A9" as used herein means a family member of the S100 calcium binding proteins and includes all know S100A8/A9 molecules including human, naturally occurring variants and those deposited in Genbank, for example, with accession number NM_002964, NM_02965, each of which is herein incorporated by reference.

The term "S100A12" as used herein means a family member of the S100 calcium binding proteins and includes all know S100A12 molecules including human, naturally occurring variants and those deposited in Genbank, for example, with accession number NM_005621, each of which is herein incorporated by reference.

The term "HMGB1" as used herein means a family member of the S100 calcium binding proteins and includes all know HMGB1 molecules including human, naturally occurring variants and those deposited in Genbank, for example, with accession number NM_002128.4, each of which is herein incorporated by reference.

The term "subject" as used herein includes all members of the animal kingdom including mammals, and suitably refers to humans.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives.

The term "consisting" and its derivatives, as used herein, are intended to be closed ended terms that specify the presence of stated features, elements, components, groups, integers, and/or steps, and also exclude the presence of other unstated features, elements, components, groups, integers and/or steps.

Further, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

More specifically, the term "about" means plus or minus 0.1 to 50%, 5-50%, or 10-40%, 10-20%, 10%-15%, preferably 5-10%, most preferably about 5% of the number to which reference is being made.

As used in this specification and the appended claims, the singular forms "a", "an" and "the" include plural references unless the content clearly dictates otherwise. Thus for example, a composition containing "a compound" includes a mixture of two or more compounds. It should also be noted that the term "or" is generally employed in its sense including "and/or" unless the content clearly dictates otherwise.

The definitions and embodiments described in particular sections are intended to be applicable to other embodiments herein described for which they are suitable as would be understood by a person skilled in the art.

The recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

Further, the definitions and embodiments described in particular sections are intended to be applicable to other embodiments herein described for which they are suitable as would be understood by a person skilled in the art. For example, in the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

II. Methods

Subtyping chronic lung allograft dysfunction (CLAD) can allow for specifically targeted personalized therapy. CLAD is a heterogenous entity and is defined as an irreversible decline in forced expiratory volume in one second below 80% of baseline. The International Society for Heart and Lung Transplantation (ISHLT) diagnosis criteria of BOS, published in 2002, describes the variable progression pattern of CLAD that suggested a heterogenous pathogenesis and restrictive conditions should be excluded before diagnosing BOS (14). CLAD has been dissected into two distinct subtypes based on pulmonary function. The first subtype is restrictive allograft syndrome (RAS) which is defined as CLAD with irreversible decline in total lung capacity to less than 90% of baseline. RAS accounts for approximately 30% of CLAD. Bronchiolitis obliterans syndrome (BOS) is a second subtype defined as CLAD without RAS. These two subtypes show distinct clinical and radiological manifestations. RAS is a rapidly progressive disease with short survival time after its onset, showing radiological characteristics of interstitial lung disease. In contrast, BOS shows relatively slow progression with minimal interstitial infiltration (11, 19, 20). These findings illustrate distinction of the subtypes of CLAD. The relative risk of death in BOS patients has been reported to decrease over time, whereas RAS is associated with high risk of death for several years (21). There are radiological distinctions that are statistically different. For example, RAS is characterized by upper-lobe dominant fibrosis, interstitial opacity and traction bronchiectasis, while BOS is characterized by mosaic attenuation and air trapping (11, 19, 20).

Biological subtyping of human chronic lung allograft dysfunction can optionally be performed as demonstrated herein by assessing a pre-implantation IL-6 RNA transcript and/or expression product level and/or IL6 and IL-10 expression level ratio in the donor lung.

For example it is demonstrated herein that increased levels of IL-6 levels and/or IL-6/IL-10 expression level ratio in donor lung is associated with increased risk of developing BOS.

It was demonstrated in U.S. Pat. No. 8,247,175 (Keshavjee et al), that IL-6/IL-10 ratio measured in the donor lung before implantation significantly predicted recipient 30 day mortality. An increased ratio predicted worse outcome.

It is herein demonstrated that IL-6/IL-10 ratio is predictive of CLAD subtype. An increased ratio of IL-6/IL-10 is associated with BOS subtype CLAD. As mentioned above BOS is associated with a decreased risk of death compared to RAS. Patient survival of RAS has been shown to be significantly worse than BOS after CLAD development (Sato et al, 2011). U.S. Pat. No. 8,247,175 (Keshavjee et al) discloses for example that increased IL-6/IL-10 ratio in donor lungs is associated with a worse acute outcome, primary graft dysfunction (PGD).

Biological subtyping of human chronic lung allograft dysfunction can optionally be performed as demonstrated herein by profiling bronchoalveolar lavage (BAL) fluid.

A differential proteomic analysis of BAL fluid from a group of lung transplant patients with or without CLAD RAS subtype identified 30 proteins that were not present in BAL from non-CGD (e.g. non chronic graft dysfunction or no-CLAD) samples IS NON-CGD=NON-CLAD, including S100 family proteins S100-A9, S100-A8, S100-A12 and S100P (19). These proteins were not validated and were not assessed for their ability to discriminate BOS and RAS subtypes.

It is also demonstrated herein that S100A8, S100A9, S100A8/A9 and/or S100A12 can distinguish RAS from no CLAD and RAS from BOS, in BAL fluid. It is further shown that S100A8 can distinguish RAS from no CLAD and BOS from no CLAD in BAL fluid, e.g. distinguishing CLAD from no CLAD. Accordingly, it is demonstrated herein that HMGB1 can distinguish RAS from BOS subtype CLAD and that S100P can distinguish RAS subtype from no CLAD.

Accordingly an aspect includes a method for assaying a donor lung for bronchiolitis obliterans syndrome (BOS) subtype or restrictive allograft syndrome (RAS) subtype of chronic allograft lung dysfunction (CLAD) or risk of developing BOS subtype or RAS subtype CLAD post-transplant, the method comprising:
 a. measuring a normalized expression level of an RNA transcript of IL-6 or an expression product thereof in a sample of the donor lung pre-transplant or a normalized expression level of one or more S100A8, S100A8/A9, S100A9, S100A12, S100P and/or HMGB1, polypeptide expression product in a sample from the donor lung post-transplant;
 b. assessing the likelihood of the donor lung of having and/or developing CLADBOS subtype CLAD or RAS subtype CLAD post-transplant based on said IL-6, S100A8 S100A8/A9, S100A9, S100A12, S100P and/or HMGB1, expression level wherein detecting increased IL-6 expression identifies an increased likelihood of developing BOS post-transplant, detecting an increased level of S100A8, S100A8/A9, S100A9, S100A12, S100P and/or HMGB1 expression identifies an increased likelihood of having and/or developing CLAD (RAS and/or BOS subtype CLAD), and/or detecting an increased level of S100A9, S100A8/A9, S100A9, S100A12, S100P and/or HMGB1 identifies an increased likelihood of having and/or developing RAS subtype CLAD.

As mentioned above an IL-6/IL-10 expression level ratio can also be used to differentiate BOS and RAS subtypes.

In an embodiment, the normalized expression level of the RNA transcription of IL-6 or the expression product thereof is measured, the method further comprising:
 a. measuring a normalized expression level of an RNA transcript of IL-10 or an expression product thereof in a sample from the donor lung pre-transplant;
 b. calculating an IL-6/1L-10 expression level ratio; and
 c. assessing the likelihood of the donor lung developing BOS subtype CLAD post-transplant based on said IL-6/IL-10 expression level ratio wherein said ratio is positively correlated with an increased likelihood of developing BOS subtype CLAD post-transplant.

The sample from the donor lung for assessing IL-6 and/or IL-10 expression levels and/or ratio is optionally a biopsy taken from the lung, for example taken after the cold ischemic period.

In an embodiment, the RNA transcript level of IL-6 and/or IL-10 is measured. In another embodiment, the polypeptide expression level of IL-6 and/or IL-10 is measured.

As described above, BOS subtype is associated with increased allograft survival post-transplant. Identifying donor lungs which have increased likelihood of allograft survival post-transplant can be useful when assessing whether an organ should be transplanted.

In an embodiment, a normalized expression level of an RNA transcript of IL-6 or an expression product thereof is measured.

As demonstrated in Example 5, higher levels of relative IL-6 RNA transcript expression are present in donor lungs that develop post-transplant CLAD, and/or BOS subtype CLAD.

Accordingly in a further aspect the method is for assaying a donor lung for risk of developing BOS subtype of CLAD post-transplant, the method comprising:

a. measuring a normalized expression level of an RNA transcript of IL-6 or an expression product thereof in a sample from the donor lung pre-transplant;
b. predicting the likelihood of the donor lung developing BOS subtype CLAD post-transplant based on said IL-6 expression level wherein said IL-6 expression level is positively correlated with an increased likelihood of developing BOS subtype CLAD post-transplant.

In an embodiment, levels of IL-6 are used for assessing late onset CLAD, optionally late onset RAS and/or late onset BOS.

Figure 2:
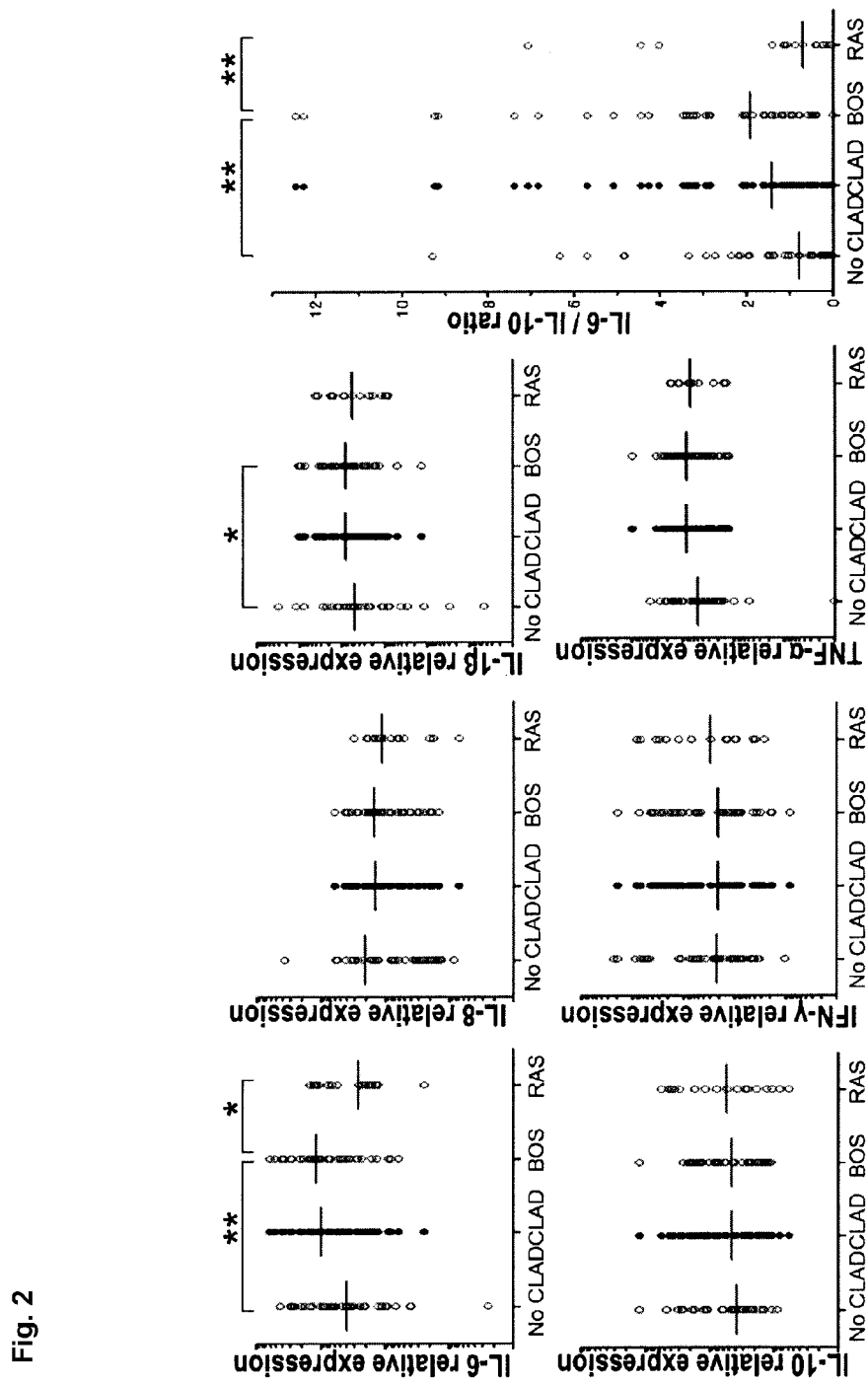
FIG. 2: Cytokine mRNA relative expression and IL-6/IL-10 ratio in PRE-transplant donor lung according to long-term outcome. Each circle shows $\log_2$-transformed relative expression levels of the cytokines normalized with the expression levels of 18S rRNA. Vertical lines show the medians of each groups. The p-values of each comparison among three groups (No CLAD, BOS and RAS) are: for IL-6: 0.002, for IL-8: 0.367, for IL-1β: 0.050, for IL-10: 0.913, for INF-γ: 0.813, for TNF-α: 0.343 and IL-6/IL-10 ratio: 0.001. Kruskal-Wallis analysis of variance test with Dunn's post-tests: *$p<0.05$ and **$p<0.01$.

As demonstrated for example in FIG. 2, increased IL-6/IL-10 expression level ratio is associated with BOS subtype. Accordingly, in an embodiment a normalized expression level of an RNA transcript of IL-6 or an expression product thereof and a normalized expression level of an RNA transcript of IL-10 or an expression product thereof are measured in a sample from the donor lung pre-transplant; an IL-6/IL-10 expression level ratio is calculated; and the likelihood of the donor lung developing BOS subtype CLAD post-transplant is predicted based on said IL-6/IL-10 expression level ratio wherein said ratio is positively correlated with an increased likelihood of developing BOS subtype CLAD post-transplant.

In an embodiment, IL6/IL10 ratio is used for assessing early onset CLAD, optionally early onset RAS and/or early onset BOS.

In an embodiment, the method further comprises measuring $PaO_2/FiO_2$ value. In an embodiment, a $PaO_2/FiO_2$ value below 200 mmHg, for example at ICU arrival, is indicative of early-onset BOS.

In an embodiment, predicting the likelihood comprises comparing the IL-6 level and/or the IL-6/IL-10 expression level ratio with a control ratio determined from levels in control lung samples. The control ratio can be calculated from a lung/subject with known outcome or based on a population of lungs/subjects with known outcome. In an embodiment, the control ratio is a median ratio or average ratio associated with a control population.

In an embodiment, a normalized expression level of an RNA transcript of IL-6 or an expression product thereof and a normalized expression level of an RNA transcript of IL-10 or an expression product thereof are measured in a sample from the donor lung; an IL-6/IL-10 expression level ratio is calculated; and the donor lung is identified as one with a decreased risk of developing BOS subtype CLAD post-transplant if said IL-6/IL-10 expression level ratio is lower in the sample than a control ratio determined from levels from control lung samples. In embodiments, wherein said IL-6/IL-10 expression level ratio is higher in the sample than a control ratio determined from levels from control lung samples, the donor lung is identified as one with a increased risk of developing BOS subtype CLAD post-transplant.

The control ratio can for example be a cut-off value. In an embodiment, the control ratio is a predetermined value below which a lung/subject has a decreased risk of developing BOS post-transplant and above which the lung/subject has an increased risk of developing BOS post-transplant. The control value can be the comparator population. For example, the comparator population can be a population with no CLAD, RAS or BOS depending on the method.

In an embodiment, the cut-off value and/or threshold is calculated from a control group, optionally a control group of a large cohort. In an embodiment, the cut-off value and/or threshold is adjusted to include additional control samples, for example as the sample size assessed is increased.

In an embodiment, the cut-off value is calculated from a plurality of known outcome patients. For example, running log-rank statistics can be used to obtain a best-fit cutoff point of the cytokine mRNA expression levels for discriminating long-term outcomes over time. In an embodiment, running log-rank statistics can be used to divide patients into two groups based on whether their cytokine mRNA expression levels are above or below a cutoff point and donor lungs can be classified as more likely to develop for example i) RAS or BOS subtype CLAD, or ii) CLAD or NO-CLAD. In an embodiment, the maximum log-rank statistical test can be used to obtain the best-fit cutoff point of the cytokine mRNA expression levels and to determine whether lung transplant recipients have a higher likelihood of having and/or developing CLAD and/or a BOS or RAS subtype thereof. Based on this cut-off, a donor lung can be identified as more or less likely to have the associated outcome. The optimal cut-off can be selected for a specific sensitivity and/or specificity.

A further aspect includes a method for determining the increased likelihood of a donor lung having CLAD and/or a BOS or RAS subtype thereof, the method comprising
a. measuring a IL-6 mRNA relative expression level in a pre-transplant donor lung;
b. detecting an increased relative expression of IL-6 mRNA;
c. identifying the donor lung with increased IL-6 mRNA relative expression level relative to a control as having or having an increased likelihood of developing CLAD and/or a BOS or RAS subtype thereof and/or identifying the donor lung with increased IL-6 mRNA relative expression compared to a cutoff point as having or having an increased likelihood of developing CLAD and/or a BOS or RAS subtype thereof.

In an embodiment, the level of IL-6 mRNA relative expression identifying the donor lung as having or having an increased likelihood of developing CLAD is greater than at least 0.04, at least 0.05, at least 0.06, at least 0.07, at least 0.08, at least 0.09, at least 0.10, at least 0.11, at least 0.12, at least 0.121, at least 0.122, at least 0.123, at least 0.124, at least 0.125, at least 0.126, at least 0.127, at least 0.128, at least 0.129 at least 0.13, at least 0.14, at least 0.15, at least 0.16, at least 0.17, at least 0.18, at least 0.19, at least 0.20, at least 0.21, or at least 0.22.

In an embodiment, the level of IL-6 mRNA relative expression identifying the donor lung as having or having an increased likelihood of developing CLAD and/or a RAS subtype thereof is at least 0.04, is at least 0.05, is at least 0.06, is at least 0.07, is at least 0.071, is at least 0.072, is at least 0.073, is at least 0.074, is at least 0.075, is at least 0.076, is at least 0.077, is at least 0.078, is at least 0.079, and less than about 0.08, about 0.085, about 0.09, about 0.095 and/or about 0.10.

In an embodiment, the maximum log-rank statistical value of developing CLAD is 12.5, which results in an optimal cutoff point for IL-6 mRNA relative expression level of 0.124.

In an embodiment, the maximum log-rank statistical value of developing CLAD and/or a BOS subtype thereof is 24.6, which results in an optimal cutoff point for IL-6 mRNA relative expression level of 0.124.

In an embodiment, the maximum log-rank statistical value of developing CLAD and/or a RAS subtype thereof is 7.64, which results in an optimal cutoff point for IL-6 mRNA relative expression level ranging from 0.077 to 0.079.

In a further embodiment, the lung donation received by the lung transplant recipient is from a brain death donor (DBD). In an embodiment the DBD donor lung is assessed for relative expression levels of an SL100A protein described herein, HMGB1, IL-6 land/or IL6/IL-10 ratio.

In an embodiment, the lung donation is not a DCD donor lung.

In an embodiment, an expression level or expression level ratio is increased or decreased by at least 10%, 20%, 30%, 40%, 50%, 60%, 70%, 80%, 90% or 95%. In another embodiment, the expression level or expression level ratio is increased or decreased by at least 1.2×, 1.5× 2×, 3×, 4×, 5×, or more.

For example, in an embodiment, the ratio is greater than 0.78, 1, 1.2, 1.5, 1.7, 2, 3, 3, 5, 10, 15, 20 or more, or the ratio is less than 1.175, 1, 0.8, 0.6, 0.4, 0.2, 0.1, 0.05, 0.001 or less. In another embodiment the differential expression is measured using p-value. For instance, when using p-value, a is identified as being differentially expressed as between a first and second population when the p-value is less than 0.1, preferably less than 0.05, more preferably less than 0.01, even more preferably less than 0.005, the most preferably less than 0.001.

Accordingly, yet a further aspect includes a method to identify a donor lung that has increased risk of BOS subtype CLAD, the method comprising:
a. measuring a normalized expression level of an RNA transcript of IL-10 or an expression product thereof and measuring a normalized expression level of an RNA transcript of IL-6 or an expression product thereof in a sample from the donor lung;
b. calculating an IL-6/IL-10 expression level ratio; and
c. identifying the donor lung as one with an increased risk of developing BOS subtype CLAD post-transplant based on said IL-6/IL-10 expression level ratio wherein said ratio is positively correlated with an increased likelihood of developing BOS subtype CLAD.

The above method steps can also be used in some embodiments to assess likelihood of developing RAS.

In an embodiment, the method further comprises selecting the donor lung with a risk of developing BOS subtype CLAD or RAS subtype CLAD below a desired risk level for transplant.

The desired risk can be a selected hazard ratio (for example less than about 3, less than about 2.5, less than about 2, or less than about 1.5). The hazard risk selected can for example depend on the subject to be transplanted and the general health of the recipient.

A further aspect includes a method of selecting a donor lung for transplant, the method comprising:
a. measuring a normalized expression level of an RNA transcript of IL-6 or an expression product thereof, in a sample of the donor lung pre-transplant;
b. predicting the risk of the donor lung developing BOS subtype CLAD or RAS subtype CLAD post-transplant based on said IL-6, wherein IL-6 expression level is positively correlated with an increased likelihood of developing BOS post-transplant; and
c. selecting the donor lung for transplant if the risk of developing BOS subtype CLAD or RAS subtype CLAD is below a desired risk level.

In some embodiments, the method further comprises:
a. measuring a normalized expression level of an RNA transcript of IL-10 or an expression product thereof in a sample from the donor lung pre-transplant;
b. calculating an IL-6/1L-10 expression level ratio; and
c. predicting the likelihood of the donor lung developing BOS subtype CLAD post-transplant based on said IL-6/IL-10 expression level ratio wherein said ratio is positively correlated with an increased likelihood of developing BOS subtype CLAD post-transplant.

In an embodiment, the expression level ratio is calculated according to the formula log normalized IL-6 expression level/log normalized IL-10 expression level.

In embodiments wherein an IL-6/IL-10 expression level ratio is determined such can be determined by taking the log 2 normalized expression level of IL-6 RNA transcript divided by the log 2 normalized expression level of IL-10 RNA transcript, for example according to the following:

$$\text{Gene Ratio} = \text{Log}_2 \frac{\text{Level of } RNA \text{ transcript of } IL\text{-}6 \text{ in Sample}}{\text{Level of } RNA \text{ transcript of } IL\text{-}10 \text{ in Sample}} \quad \text{(Equation 1)}$$

In an embodiment, the expression level and/or expression level ratio is associated with early onset BOS or early onset RAS.

Kaplan-Meier curves in FIG. 4 shows probability of developing BOS, RAS and CLAD and allograft survival rate according to IL-6/IL-10 subgroups. In the univariate analysis, IL-6/IL-10 ratio>0.78 was associated with earlier development of BOS, while IL-6/IL-10≤1.175 was associated with earlier development of RAS (FIGS. 4 A, B). Probability to develop CLAD and overall allograft survival are shown in FIGS. 4 C and D.

Table 2 shows the results of multivariate Cox regression analysis. Early development of BOS were associated with early DAD, acute rejection and IL-6/IL-10 ratio>0.78 ratio with hazard ratio of 2.507 [1.112-5.652], 2.715 [1.099-6.708] and 4.557 [1.798-11.616], respectively (Table 2A). On the other hand, early RAS onset was associated with CMV mismatch (D+R−), late new-onset DAD and female-to-female gender matching. The hazard ratio was 10.297 [1.675-63.316], 40.780 [7.374-225.486] and 5.007 [1.030-24.335], respectively (Table 2B). Cystic fibrosis and pulmonary arterial hypertension showed lower hazard ratio compared with idiopathic pulmonary fibrosis. In addition, early CLAD development was associated with late new-onset DAD, female-to-female gender matching, IL-6/IL-10 ratio between 0.78 and 1.175 and IL-6/IL-10 ratio>1.175. The hazard ratio was 3.761 [1.645-8.598], 2.293 [1.070-4.914], 3.803 [1.600-9.040] and 2.231 [1.123-4.429], respectively (Table 2C). Early allograft loss was associated with female-to-female gender matching and IL-6/IL-10 ratio between 0.78 and 1.175 with hazard ratio of 2.396 [1.098-5.226] and 2.995 [1.352-6.637], respectively (FIG. 2D).

In an embodiment, the donor lung is identified to be one with an increased risk of early BOS subtype CLAD development when the IL-6/IL-10 ratio is greater than 0.78.

In an embodiment, the donor lung is identified to be one with an increased risk of early RAS subtype CLAD when the IL-6/IL-10 ratio is less than or equal to 1.175.

Also, in an embodiment, the method can be used to assess for early CLAD development. As described, CLAD development was associated with an IL-6/IL-10 ratio between 0.78 and 1.175 and IL-6/IL-10 ratio>1.175. In another embodiment, the method can be used to assess early allograft loss, for example when the IL-6/IL-10 ratio between 0.78 and 1.175.

A person skilled the art would recognize that other ratios can be used depending for example on the desired sensitivity and specificity.

Assessing and/or predicting the likelihood of and/or identifying the donor lung as one to develop BOS subtype CLAD or RAS subtype CLAD post-transplant based on said expression levels can involve comparing the measured expression level or calculated expression ratio to one or more controls and assessing one or more clinically relevant factors.

In an embodiment, the prediction/identification comprising pre-transplant expression levels further comprises assessing one or more of diffuse alveolar damage (DAD), acute rejection CMV mismatch and late new onset DAD.

In an embodiment, the level of RNA transcript is measured by quantitative real time PCR.

A person skilled in the art will appreciate that a number of methods can be used to measure or detect the level of RNA transcripts within a sample, including microarrays, RT-PCR (including quantitative RT-PCR and rapid RT-PCR), nuclease protection assays, in situ hybridization, in situ RT-PCR and northern blots.

In an embodiment, IL-6 and IL-10 RNA transcript levels are measured by quantitative RT-PCR, optionally quantitative multiplex rapid RT-PCR, which can be carried using for example SmartCycler II® (Cephied). In an embodiment, QuantiTect SYBR Green PCR kit is used.

IL-6 and IL-10 transcript levels can be normalized to levels of 18S ribosomal RNA. The measurement of the cytokine expression ratio using the same amount of cDNA transcribed from total RNA can obviate the need for endogenous controls, which are eventually cancelled out in the process of calculating a ratio. This strategy can improve accuracy in measurement which is relevant for clinical use.

In an embodiment, the level of the RNA transcript is normalized with the expression of 18s rRNA.

In an embodiment, the methods comprise selecting a threshold or cut off to provide greater than 70%, 80%, 85%, 90%, 95% or 98% diagnostic accuracy.

In an embodiment, the method comprises first obtaining a sample of the donor lung for measuring the normalized expression levels.

As mentioned above, several S100 family proteins including S100A8, S100A9, S100A8/A9, S100A12, S100P as well as HMGB1 are also shown to be associated with CLAD and/or CLAD subtype It is demonstrated herein using receiver operating characteristic (ROC) curves that S100A9 is able to differentiate RAS from BOS and S100A8 is able to differentiate CLAD from no CLAD. Area under the ROC curves are 0.95 [95% CI, 0.85-1.05] in differentiating RAS from BOS by S100A9 and 0.89 [95% CI, 0.78-1.01] in differentiating CLAD from No CLAD by S100A8 (FIG. 7).

Figure 7:
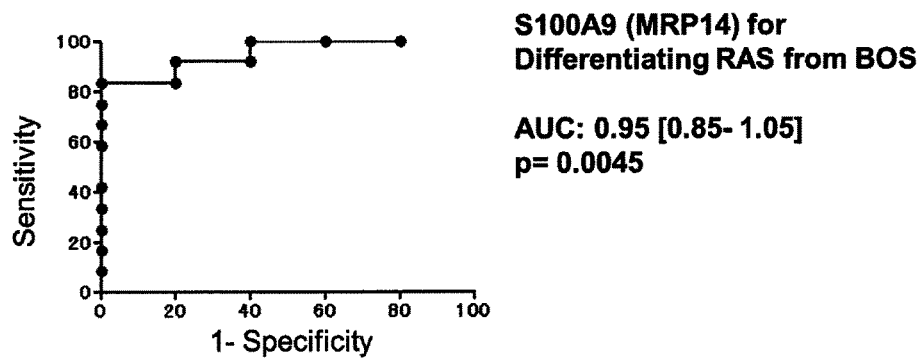
FIG. 7: Receiver operating characteristic curves for S100 A8 and A9.
Figure 7:
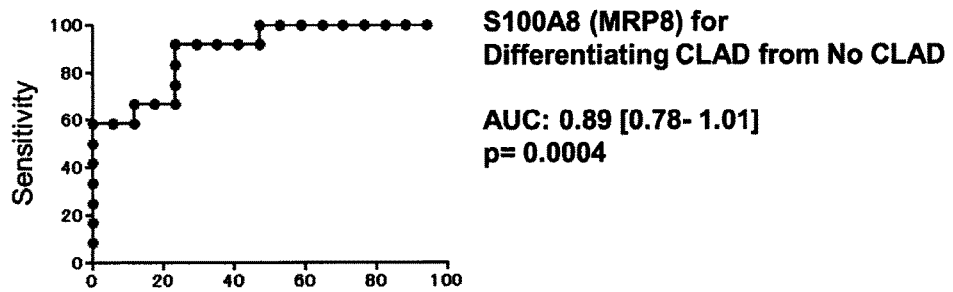

It is also demonstrated herein using ROC curves that S100A8/A9 and S100A12 are able to differentiate CLAD versus no CLAD and that S100A9, S100A8/A9, S100A12 and HMGB1 are able to differentiate RAS from BOS CLAD subtype (see FIG. 7 and table 14). Accordingly a further aspect includes a method for assaying a donor lung as having CLAD, optionally BOS subtype or RAS subtype CLAD, post-transplant, the method comprising:
  a. measuring a normalized expression level of S100A8, S100A9, S100A8/A9, S100A12 and/or HMGB1, polypeptide expression product in a BAL sample from the donor lung post-transplant;
  b. determining an increased expression of S100A8, S100A9, S100A8/A9 and/or S100A12 compound to a CLAD threshold and/or detecting an increased expression of S100A8, S100fA9, S100A8/A9, S100A12 and/or HMGB1 compared to a RAS threshold; and
  c. identifying the donor lung with increased S100A8, S100A9, S100A8/A9 and/or S100A12 expression level compound to the CLAD threshold as having or having an increased likelihood of developing CLAD, optionally RAS and/or BOS subtype CLAD, and/or identifying the donor lung with increased S100A9, S100A8/A9, S100A12 and/or HMGB1 expression level compared to RAS threshold as having or having an increased likelihood of developing RAS subtype CLAD.

In an embodiment, the method comprises measuring the method comprises measuring a normalized expression level of S100A8 polypeptide expression product in a sample from the donor lung post-transplant and a subject with an increased level of S100A8 compared to a control is assessed as having or having an increased likelihood of developing CLAD optionally RAS and/or BOS subtype CLAD.

In an embodiment, the method comprises measuring a normalized expression level of S100A9 polypeptide expression product in a sample from the donor lung post-transplant and a subject with an increased level of S100A9 compared to a control is assessed as having or having an increased likelihood of developing RAS subtype CLAD.

In an embodiment, the method comprises measuring a normalized expression level of S100A8 polypeptide expression product in a sample from the donor lung post-transplant and a subject with an increased level of S100A8 compared to a control is assessed as having or having an increased likelihood of developing RAS subtype CLAD.

In an embodiment, the method comprises measuring a normalized expression level of S100A8/A9 polypeptide expression product in a sample from the donor lung post-transplant and a subject with an increased level of S100A8/A9 compared to a control is assessed as having or having an increased likelihood of developing RAS subtype CLAD.

In an embodiment, the method comprises measuring a normalized expression level of S100A12 polypeptide expression product in a sample from the donor lung post-transplant and a subject with an increased level of S100A12 compared to a control is assessed as having or having an increased likelihood of developing RAS subtype CLAD.

In an embodiment, the method comprises measuring a normalized expression level of S100P polypeptide expression product in a sample from the donor lung post-transplant and a subject with an increased level of S100P compared to a control is assessed as having or having an increased likelihood of developing RAS subtype CLAD.

In an embodiment, the method comprises measuring a normalized expression level of HMGB1 polypeptide expression product in a sample from the donor lung post-transplant and a subject with an increased level of HMGB1 compared to a control is assessed as having or having an increased likelihood of developing RAS subtype CLAD.

In an embodiment, the sample from the donor lung is a bronchoalveolar lavage (BAL) sample.

In an embodiment, the level of S100A9 in BAL identifying the donor lung as having or having an increased likelihood of developing CLAD and/or RAS subtype CLAD (e.g. RAS threshold) is greater than at least at least 18 ng/mL, at least 20 ng/mL, at least 22 ng/mL, at least 24 ng/mL, at least 26 ng/mL, at least 28 ng/mL, at least 30 ng/mL, at least 32 ng/mL, at least 34 ng/mL, at least 36 ng/mL, at least 38 ng/mL, at least 40 ng/mL, at least 42 ng/mL, at least 44 ng/mL, at least 46 ng/mL, at least 48 ng/mL, at least 50 ng/mL, at least 52 ng/mL, at least 54 ng/mL, at least 56 ng/mL or at least 58 ng/mL.

In another embodiment, the level of S100A8 in BAL identifying the donor lung as having or having an increased likelihood of developing BOS subtype CLAD is greater than about 28 ng/mL, about 30 ng/mL, about 32 ng/mL, about 34 ng/mL, about 36 ng/mL, about 38 ng/mL, about 40 ng/mL, about 32 ng/mL, about 34 ng/mL or about 36 ng/mL and less than about 200 ng/mL, about 250 ng/mL, about 300 ng/mL, and/or about 350 ng/mL.

In an embodiment, the level of S100A8/A9 identifying the donor lung as having or having an increased likelihood of developing RAS subtype CLAD is greater than at least 3 ng/mL, at least 3.5 ng/mL, at least 4 ng/mL, at least 5 ng/mL, at least 6 ng/mL, at least 7 ng/mL, at least 8 ng/mL, at least 9 ng/mL and at least 10 ng/mL.

In an embodiment, the level of S100A12 in BAL identifying the donor lung as having or having an increased likelihood of developing CLAD and/or RAS subtype CLAD is greater than at least 150 ng/mL, at least 160 ng/mL, at least 170 ng/mL, at least 180 ng/mL, at least 190 ng/mL, at least 200 ng/mL, at least 210 ng/mL, at least 220 ng/mL, at least 230 ng/mL, at least 240 ng/mL and at least 250 ng/mL.

In an embodiment, the level of S100A12 identifying the donor lung as having or having an increased likelihood of developing CLAD, optionally in BAL, is greater than at least 35 ng/mL, at least 40 ng/mL, at least 50 ng/mL, at least 55 ng/mL, at least 60 ng/mL.

In an embodiment, the level of S100A9 identifying the donor lung as having or having an increased likelihood of developing RAS type CLAD is increased at least 2 fold, at least 3 fold, at least 4 fold, at least 5 fold, compared to a no CLAD and/or BOS subtype control and/or threshold.

In another embodiment, the level of S100A8 identifying the donor lung as having or having an increased likelihood of developing RAS subtype CLAD is at least 4 times, at least 5 times, at least 6 times, at least 7 times, at least 8 times, at least 9 times, at least 10 times, at least 11 times, at least 12 times, at least 13 times, at least 14 times and/or at least 15 times, compared to a RAS threshold e.g. above which and below which is indicative of BOS subtype.

In another embodiment, the level of S100A8 identifying the donor lung as having or having an increased likelihood of developing RAS subtype CLAD is at least 20, at least 25, at least 30 times increased compared to a CLAD threshold, above which is indicative CLAD and below which is indicative of no CLAD.

In another embodiment, the level of S100A8/A9 identifying the donor lung as having or having an increased likelihood of developing RAS subtype CLAD is at least 3, at least 4, at least 5, at least 6, at least 7, at least 8, at least 9 and/or at least 10 times increased compared to a RAS threshold and/or a CLAD threshold.

In another embodiment, the level of S100A12 identifying the donor lung as having or having an increased likelihood of developing RAS subtype CLAD is at least 6, at least 7, at least 8, at least 9, and/or at least 10 times increased compared to a medium level in BOS and/or at least 8, at least 9, at least 10 and at least 12, at least 14, at least 16, at least 18, at least 20 times increased compared to a no CLAD medium.

In an embodiment, the level of S100P identifying the donor lung as having or having an increased likelihood of developing CLAD is at least 3, at least 4 at least 5 times greater than a no CLAD and/or BOS medium.

In an embodiment, the level of HMGB1 identifying the donor lung as having or having an increased likelihood of developing CLAD is at least 3, at least 4 at least 5 times greater than a no CLAD and/or BOS medium.

In yet a further embodiment, the level of S100A8 identifying the donor lung as having or having an increased likelihood of developing RAS subtype CLAD is greater than about 200 ng/mL.

In an embodiment, the level of polypeptide expression product is measured by immunoassay. In an embodiment, the immunoassay is an ELISA.

In an embodiment, the measuring comprises contacting the sample with an antibody and creating a biomarker (e.g. IL-6, IL-10, S100A8, S100A9, S100A8/A9, S100A12, S100P and/or HMGB1): antibody complex normalizing the amount of biomarker antibody complex to obtain a normalized expression level.

A person skilled in the art would recognize that the level of a polypeptide can be determined by a number of methods using different assays including for example mass spectrometric based assays, including for example MS, MS/MS, LC-MS/MS, SRM etc where a peptide of a biomarker is labeled and the amount of labeled biomarker peptide is ascertained, immunoassays including for example immunohistochemistry, ELISA, e.g. sandwich type ELISA, Western blot, immunoprecipitation, immunofluorescence, radioimmunoassay, dot blotting, FACS and the like, where a biomarker specific detection agent such as an antibody for example, a labeled antibody, specifically binds the biomarker (e.g. an epitope therein) and permits for example relative or absolute ascertaining of the amount of polypeptide biomarker.

In an embodiment, the methods described herein are used to predict onset of CLAD, and/or onset of RAS and/or BOS subtype prior to clinical manifestation. In an embodiment, the methods further include initiating early therapeutic and/or preventative intervention.

A further aspect includes a method of treating a lung transplant recipient when the donor lung has been identified to have an increased likelihood of having and/or developing CLAD and/or a BOS or RAS subtype thereof.

Therapeutic and preventive treatment of BOS may include IL-6 blockade, neutralization or attenuation. IL-6 neutralization [has been demonstrated to attenuate airway obliteration and IL-17 mRNA expression in a mouse model of obliterative bronchiolitis[16]. Adenoviral IL-10 gene therapy under normothermic ex vivo lung perfusion has also been demonstrated to attenuate both IL-6 and IL-1β production in lung tissue after four hours of reperfusion in a large-animal lung transplant model[47,48]. IL-6 neutralization or IL-10 gene therapy or both could be explored as a therapeutic pre-transplant intervention to prevent BOS. Immunosuppressants such as tacrolimus and/or antibacterials such as azithromycin can optionally be used.

III. Kit and Composition

Another embodiment includes a kit for detecting the expression level of two or more of IL-6, IL-10, HMGA1, and a SL100A protein described herein. In an embodiment, the kit comprises at least two antibodies, specific for two or more of IL-6, IL-10, HMGA1, and a SL100A protein described herein. In yet another embodiment, the kit comprises at least 2 primers, optionally primers described herein or primers that are similar there to, for example having at least at least 7, 8, 9, 10, 11 or 12 contiguous nucleotides in common. The primers are optionally labelled. In an embodiment, the kit comprises one or more reference standards, for example protein or DNA reference standards, reagents for detecting protein and/or RNA expression. In an embodiment, the kit is an ELISA, optionally a standardized ELISA for detecting one, two or more of the proteins described herein.

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Chronic lung allograft dysfunction (CLAD) is the major limitation to long-term success of lung transplantation. However, it is currently difficult to predict CLAD based on the characteristics of donor lung.

The mechanism of CLAD is a complex multifactorial process involving alloimmune-dependent and alloimmune-independent injury with aberrant tissue remodeling[2,3]. Development of CLAD has been shown to be associated with activation of tissue-resident stromal cells such as endothelial and epithelial cells, formation of lymphoid-like stroma and formation of intrapulmonary de novo lymphoid tissue[4,5].

Cytokines may play important roles in development of CLAD. In fact, several cytokines in bronchoalveolar lavage fluid and plasma have been shown to be contributing factors of CLAD[6-9]. However, since these previous reports were based on post-transplant specimens, the impact of pre-transplant cytokine profile of donor lung is yet to be elucidated.

Lung tissue biopsy specimens were taken from 143 transplanted donor lungs at the end of cold ischemic time. Expression levels of interleukin IL-6, IL-1β, IL-8, IL-10, interferon-γ, and tumor necrosis factor-α messenger RNA were measured by quantitative real-time reverse transcription polymerase chain reaction. Prospectively collected clinical data on 143 recipients were retrospectively reviewed and compared with the cytokine profiles. CLAD and its subtypes, restrictive allograft syndrome (RAS) and bronchiolitis obliterans syndrome (BOS), were defined based on pulmonary function test results.

122 of 143 recipients survived more than 3 months after transplantation. 16 patients were excluded because of $FEV_1$ decline unrelated to graft dysfunction or insufficient data. Finally 44 patients with no CLAD, 44 with BOS and 17 with RAS were identified. Relative expression level of IL-6 and IL-6/IL-10 ratio were significantly higher in BOS compared with RAS and no CLAD patients (p=0.0019 and p=0.0010, respectively). Multivariate Cox regression analysis demonstrated early diffuse alveolar damage (DAD), acute rejection and high/intermediate IL-6/IL-10 ratio in donor lung as independent risk factors for early BOS development. On the other hand, early RAS onset was associated with CMV mismatch (D+R−) and late new-onset DAD.

High IL-6/IL-10 ratio in pre-implantation donor lungs were associated with eventual development of BOS, not RAS.

Materials and Methods

We prospectively collected lung graft biopsies taken from donor lungs at the end of the cold ischemia (just prior to implantation) in the Toronto Lung Transplant Program from 1998 to 2003. A piece of the biopsy sample (about 2×1 cm) was taken from the peripheral part of the donor lung with a mechanical stapler and immediately snap-frozen in liquid nitrogen and stored at −80° C. for subsequent analysis. Among the 169 consecutive biopsies that were taken in that period, 142 biopsies from donor lungs that were utilized for bilateral lung and heart-lung transplantation were analyzed. Patients consented to biopsies of the donor lung prior to implantation or to the use of the excess lung tissue in donor lungs that would be reduced in size to fit in the recipients.

Expression levels of IL-6, IL-8, IL-10, interferon (IFN)-γ, tumor necrosis factor (TNF)-α and IL-1β mRNA were measured in a blinded fashion by quantitative real-time RT-PCR (qRT-PCR). Prospectively collected clinical data were analyzed retrospectively and then compared to cytokine expression data. Primary endpoint was development of CLAD, BOS or RAS. Secondary endpoint was allograft survival.

Measurement of Gene Expression

The primers used for real-time PCR to amplify cytokine mRNA were designed using Primer3 website developed by the Whitehead Institute for Biomedical Research[12]. Total RNA was extracted from a portion of the lung tissue biopsies with an RNeasy Mini Kit (Qiagen, Mississauga, Canada), according to the manufacturer's instructions. cDNA was synthesized from total RNA using MultiScribe Reverse Transcriptase and random hexamers from Taqman Reverse Transcription Reagent kit (Applied Biosystems, Toronto, Canada). The reaction mix (20 μL) for reverse transcription contained 2.0 μL of 10× Taq Man RT Buffer, 4.4 μL of 25 mM magnesium chloride, 4.0 μL of 2.5 mM deoxy NTPs mixture, 1.0 μL of 50 IM random hexamers, 0.4 μL of 20 U/μL RNase inhibitor, 0.5 μL of 50 U/μL MultiScribe Reverse Transcriptase and 7.7 μL of RNase-free H2O with 500 ng of total RNA. The mixture was incubated at 25° C. for 10 min, at 48° C. for 30 min for reverse transcription and at 95° C. for 5 min for reverse transcriptase inactivation. Reactions were diluted to 60 μL with RNase-free water and stored at −20° C. PCR amplification mixtures (30 IL) contained 3 μL of the template cDNA, 15 μL of 2× QuantiTect SYBR Green PCR kit (Qiagen) and 300 nM forward and reverse primers. Reactions were run on a PRISM 9700HT (Applied Biosystems). Conditions for PCR included 95° C. for 15 min, and 40 cycles of 94° C. for 15 s (denaturation) and 60° C. for 60 s (annealing/extension). Each assay included a standard curve of five serial dilutions and a no-template negative control. All assays were performed in duplicate. The cytokine expression levels were normalized to the level of 18S ribosomal RNA.

Definition of CLAD and its Subtypes

CLAD, RAS and BOS were defined as described in detail previously[11,13]. The baseline $FEV_1$ was defined according to the criteria recommended by the International Society for Heart and Lung Transplantation (ISHLT)[14], and then the baseline TLC value was taken as the average of the parameters measured at the time of the best $FEV_1$ measurements. CLAD was defined as an irreversible decline in $FEV_1$ below 80% of baseline. RAS was defined as CLAD with an irreversible decline in TLC below 90% of baseline. BOS was strictly defined as CLAD without restrictive changes of RAS. Thus, the diagnosis of RAS was not made until $FEV_1$ dropped to meet the criteria of CLAD, even if TLC had already declined to meet the threshold. The diagnosis of BOS was not made until a valid TLC measurement was done to rule out RAS. The diagnosis of CLAD was made only if functional decline persisted after appropriate treatment for infection or acute rejection, or both. Declines in $FEV_1$ and TLC were considered reproducible only when 2 separate measurements at least 3 weeks apart met the threshold. The first date of decline in PFTs that met the criterion of each condition was recorded as the onset date.

The long-term outcome of each patient was determined by the last valid PFT result during the observation period. Allograft survival was defined as patient death or retransplantation.

Statistical Analysis

One-way analysis of variance (ANOVA) was used for parametric data, Pearson's chi-square test for categoric data, and a Kruskal-Wallis test for nonparametric data. Kaplan-Meier analyses and proportional hazard models were used to examine the effect of cytokine expression in donor lungs on eventual development of CLAD, BOS and RAS and allograft survival. Multivariate analyses included: primary diagnosis of recipients; donor and recipient age; donor-recipient gender combination and cytomegalovirus serology combination at the time of transplant; and IL-6/IL-10 ratio with cutpoints determined by calculation as described later. Early or late new-onset diffuse alveolar damage and grade 2 or more severe acute rejection within 6 months after lung transplantation were also included only if their p value was below 0.10 in the preliminary log-rank tests.

The cutpoints of IL-6/IL-10 were determined according to running log-rank statistics. In brief, all potential cutpoints for CLAD, RAS and BOS were analyzed by log-rank tests. The best cutpoints were then determined if they had the maximum log-rank statistics.

Values of p<0.05 were reported to be significant. SPSS Statistics 17.0 software (IBM, Armonk, N.Y.) for Windows (Microsoft, Redmond, Wash.) was applied.

Results

Among 143 recipients who underwent bilateral lung or heart-lung transplantation, 21 cases died within 3 months, including all the 4 cases that developed primary graft dysfunction.

121 recipients survived more than 3 months after transplantation. 16 patients were excluded because of $FEV_1$ decline unrelated to graft dysfunction or insufficient data. Finally 44 patients with No CLAD, 44 with BOS and 17 with RAS were identified (FIG. 1). Demographics and clinical characteristics of the 121 patients are shown in Table 1. There was no significant difference in clinical background among the three groups except for follow-up period.

FIG. 2 shows cytokine mRNA relative expression and IL-6/IL-10 ratio in pre-transplant donor lung according to long-term outcomes. IL-6 and IL-6/IL-10 ratio showed higher expression in BOS development group compared with No CLAD and RAS development group (p=0.002 and p=0.001, respectively), while no other cytokines (IL-8, IL-1β, IL-10, IFN-γ, TNF-α) showed significant differences.

Figure 3:
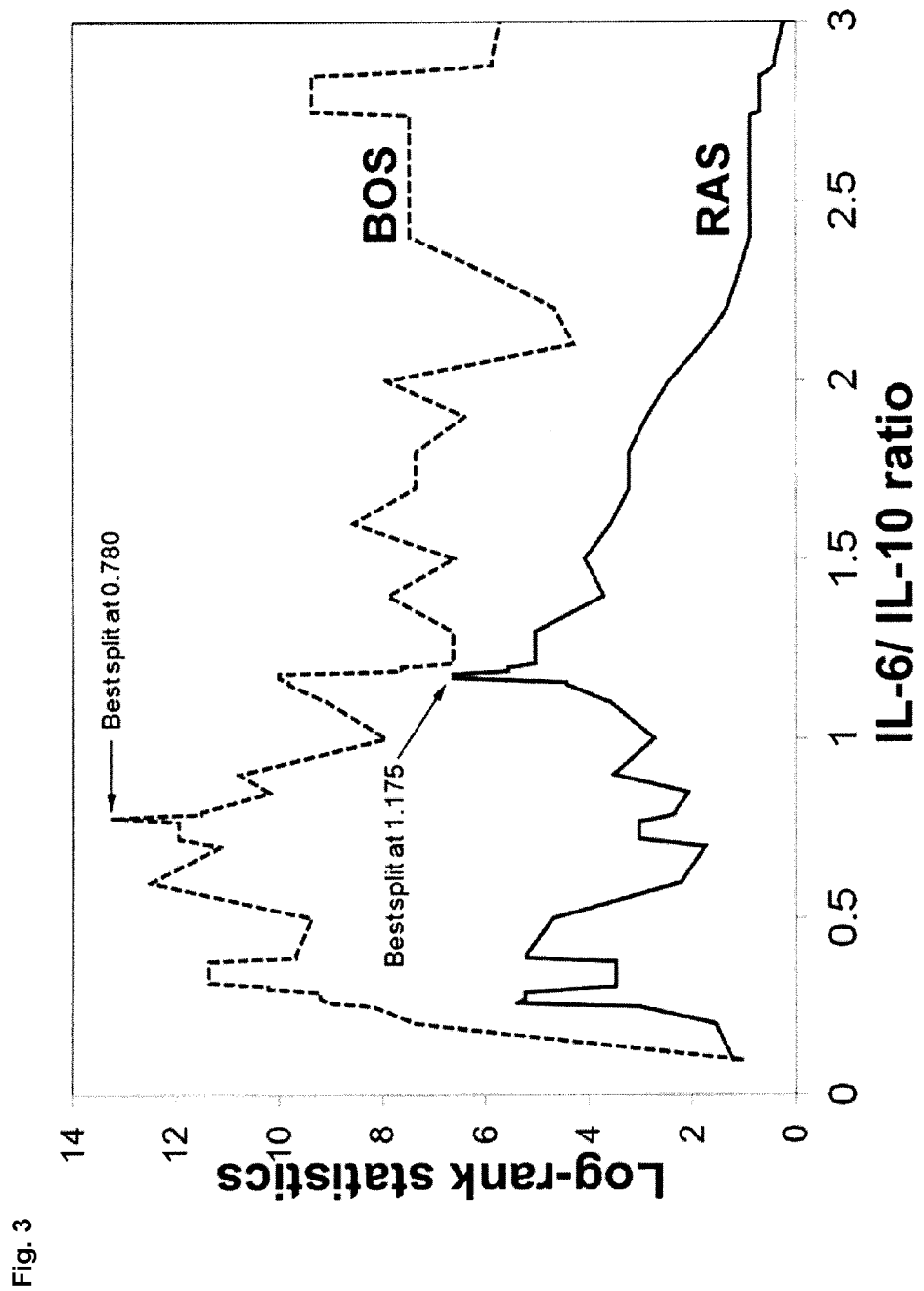
FIG. 3: Running log-rank statistics for a cutpoint of IL-6/IL-10 ratio.
Figure 4A:
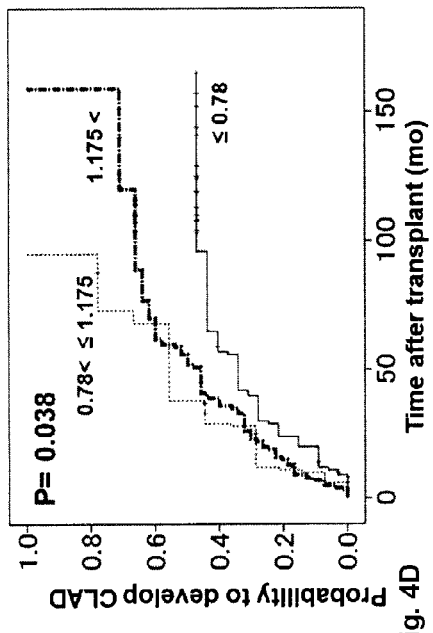
FIGS. 4A-B is a series of graphs showing the Probability to develop BOS (FIG. 4A), RAS (FIG. 4B) and CLAD (FIG. 4C) and allograft survival (FIG. 4D).
Figure 4B:
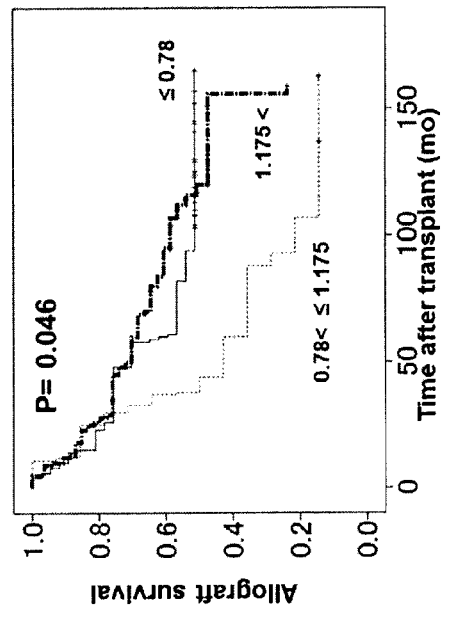
Figure 4C:
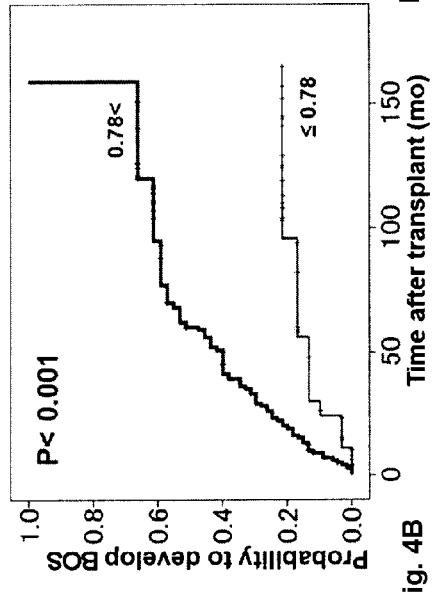
Figure 4D:
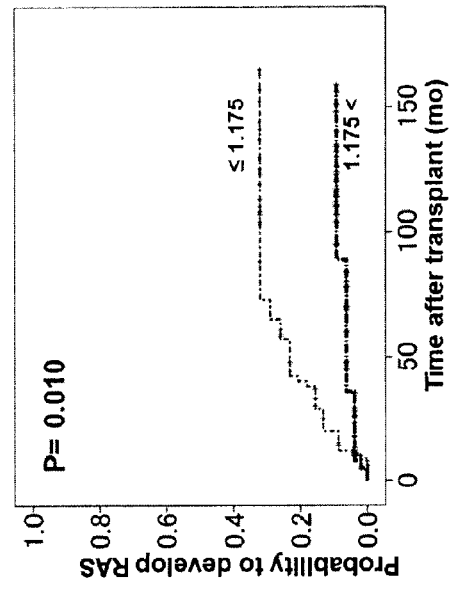

FIG. 3 shows running log-rank statistics for IL-6/IL-10 ratio cutpoints. The highest log-rank statistics were coincided with 0.78 when comparing BOS development and 1.175 when comparing RAS development. Then we employed these values as cut-points for BOS and RAS.

Kaplan-Meier curves in FIG. 4 shows probability of developing BOS, RAS and CLAD and allograft survival rate according to IL-6/IL-10 subgroups. In the univariate analysis, IL-6/IL-10 ratio>0.78 was associated with earlier development of BOS, while IL-6/IL-10≤1.175 was associated with earlier development of RAS (FIGS. 4 A, B). Probability to develop CLAD and overall allograft survival are shown in FIGS. 4 C and D. We employed both BOS and RAS cut-points in analysis on CLAD and overall allograft survival to evaluate the effect of IL-6/IL-10 ratio on them.

Table 2 shows the results of multivariate Cox regression analysis. Early development of BOS were associated with early DAD, acute rejection and IL-6/IL-10 ratio>0.78 ratio with hazard ratio of 2.507 [1.112-5.652], 2.715 [1.099-6.708] and 4.557 [1.798-11.616], respectively (Table 2A). On the other hand, early RAS onset was associated with CMV mismatch (D+R−), late new-onset DAD and female-to-female gender matching. The hazard ratio was 10.297 [1.675-63.316], 40.780 [7.374-225.486] and 5.007 [1.030-24.335], respectively (Table 2B). Cystic fibrosis and pulmonary arterial hypertension showed lower hazard ratio compared with idiopathic pulmonary fibrosis. In addition, early CLAD development was associated with late new-onset DAD, female-to-female gender matching, IL-6/IL-10 ratio between 0.78 and 1.175 and IL-6/IL-10 ratio>1.175. The hazard ratio was 3.761 [1.645-8.598], 2.293 [1.070-4.914], 3.803 [1.600-9.040] and 2.231 [1.123-4.429], respectively (Table 2C). Early allograft loss was associated with female-to-female gender matching and IL-6/IL-10 ratio between 0.78 and 1.175 with hazard ratio of 2.396 [1.098-5.226] and 2.995 [1.352-6.637], respectively (FIG. 2D).

TABLE 1

Demographics and clinical characteristics of lung transplant patients

| Characteristics | | No CLAD (n = 44) | RAS (n = 17) | BOS (n = 44) | P-Value |
|---|---|---|---|---|---|
| Follow-up period*, mo | | 93.3 ± 48.2 | 55.2 ± 40.6 | 80.5 ± 48.8 | 0.021 |
| Donor age, yr | | 39.6 ± 16.2 | 36.7 ± 16.5 | 44.6 ± 14.3 | 0.167 |
| Recipient age, yr | | 43.2 ± 15.5 | 41.2 ± 12.6 | 43.4 ± 14.2 | 0.968 |
| Donor smoking ≥20 pack-year | | 9 | 6 | 13 | 0.427 |
| Cold ischemic time (first lung), min | | 187.9 ± 75.0 | 214.4 ± 78.6 | 191.3 ± 68.7 | 0.524 |
| Primary diagnosis | IPF | 10 | 5 | 7 | 0.633 |
| | COPD | 8 | 5 | 12 | |
| | CF | 12 | 4 | 13 | |
| | PAH | 3 | 1 | 1 | |
| | A1AT | 4 | 0 | 1 | |
| | Others | 7 | 2 | 10 | |
| Transplant type | Bilateral lung | 41 | 17 | 44 | 0.243 |
| | Heart-lung | 2 | 0 | 0 | |
| Gender matching | M-M | 22 | 7 | 20 | 0.678 |
| | M-F | 1 | 1 | 4 | |
| | F-F | 13 | 4 | 14 | |
| | F-M | 8 | 5 | 6 | |
| CMV matching | D−R− | 12 | 2 | 11 | 0.105 |
| | D−R+ | 15 | 3 | 11 | |

TABLE 1-continued

Demographics and clinical characteristics of lung transplant patients

| Characteristics | No CLAD (n = 44) | RAS (n = 17) | BOS (n = 44) | P-Value |
|---|---|---|---|---|
| D+R+ | 12 | 4 | 16 | |
| D+R− | 5 | 8 | 6 | |

TABLE 2 (A)

The results of a Cox proportional hazard model for BOS development.

| Factors (P-Value) | | HR | 95% CI |
|---|---|---|---|
| Donor age (0.552) | | 1.120 | 0.883-1.420 |
| Recipient age (0.351) | | 1.120 | 0.770-1.629 |
| Primary diagnosis | IPF | 1 | — |
| | COPD (0.214) | 2.154 | 0.645-7.195 |
| | CF (0.090) | 4.218 | 0.798-22.294 |
| | PAH (0.264) | 0.261 | 0.025-2.748 |
| | A1AT (0.828) | 0.771 | 0.075-7.978 |
| Gender matching | M-M | 1 | — |
| | M-F (0.898) | 1.080 | 0.335-3.475 |
| | F-F (0.119) | 2.032 | 0.833-4.955 |
| | F-M (0.760) | 0.840 | 0.273-2.579 |
| CMV matching | D-R− | 1 | — |
| | D-R+ (0.779) | 1.155 | 0.422-3.166 |
| | D+R+ (0.103) | 2.218 | 0.852-5.774 |
| | D+R− (0.909) | 0.938 | 0.314-2.800 |
| Early DAD | (−) | 1 | — |
| | (+) (0.027) | 2.507 | 1.112-5.652 |
| Acute rejection; Grade ≥2 within 6 mo | (−) | 1 | — |
| | (+) (0.030) | 2.715 | 1.099-6.708 |
| IL-6/IL-10 ratio | ≤0.78 | 1 | — |
| | 0.78 < (0.001) | 4.557 | 1.798-11.616 |

TABLE 2 (B)

The results of a Cox proportional hazard model for RAS development.

| Factors (P-Value) | | HR | 95% CI |
|---|---|---|---|
| Donor age (0.920) | | 0.977 | 0.615-1.551 |
| Recipient age (0.017) | | 0.315 | 0.122-0.816 |
| Primary diagnosis | IPF | 1 | — |
| | COPD (0.501) | 1.885 | 0.297-11.966 |
| | CF (0.018) | 0.025 | 0.001-0.537 |
| | PAH (0.032) | 0.020 | 0.001-0.716 |
| | A1AT | — | — |
| Gender matching | M-M | 1 | — |
| | M-F (0.248) | 4.649 | 0.343-62.960 |
| | F-F (0.046) | 5.007 | 1.030-24.335 |
| | F-M (0.104) | 4.552 | 0.732-28.318 |
| CMV matching | D-R− | 1 | — |
| | D-R+ (0.485) | 2.206 | 0.239-20.349 |
| | D+R+ (0.504) | 2.102 | 0.238-18.579 |
| | D+R− (0.012) | 10.297 | 1.675-63.316 |
| Late new-onset DAD | (−) | 1 | — |
| | (+) (<0.001) | 40.780 | 7.375-225.486 |
| IL-6/IL-10 ratio | ≤1.175 | 1 | — |
| | 1.175 < (0.154) | 0.344 | 0.079-1.493 |

TABLE 2 (C)

The results of a Cox proportional hazard model for CLAD development.

| Factors (P-Value) | | HR | 95% CI |
|---|---|---|---|
| Donor age (0.464) | | 1.075 | 0.886-1.306 |
| Recipient age (0.543) | | 0.909 | 0.667-1.237 |
| Primary diagnosis | IPF | 1 | — |
| | COPD (0.128) | 2.005 | 0.819-4.905 |
| | CF (0.555) | 1.464 | 0.413-5.188 |

TABLE 2 (C)-continued

The results of a Cox proportional hazard model for CLAD development.

| Factors (P-Value) | | HR | 95% CI |
|---|---|---|---|
| | PAH (0.187) | 0.318 | 0.058-1.744 |
| | A1AT (0.213) | 0.294 | 0.043-2.024 |
| Gender matching | M-M | 1 | — |
| | M-F (0.483) | 1.456 | 0.510-4.155 |
| | F-F (0.033) | 2.293 | 1.070-4.914 |
| | F-M (0.308) | 1.584 | 0.654-3.836 |
| CMV matching | D-R− | 1 | — |
| | D-R+ (0.617) | 0.801 | 0.335-1.914 |
| | D+R+ (0.193) | 1.704 | 0.764-3.804 |
| | D+R− (0.381) | 1.473 | 0.619-3.501 |
| Late new-onset DAD | (−) | 1 | — |
| | (+) (0.002) | 3.761 | 1.645-8.598 |
| Acute rejection; Grade ≥2 within 6 mo | (−) | 1 | — |
| | (+) (0.106) | 1.935 | 0.870-4.302 |
| IL-6/IL-10 ratio | ≤0.78 | 1 | — |
| | 0.78< ≤1.175 (0.002) | 3.803 | 1.600-9.040 |
| | 1.175 < (0.022) | 2.231 | 1.123-4.429 |

TABLE 2 (D)

The results of a Cox proportional hazard model for allograft loss. Likelihood statistics was greater than the model including CLAD development instead of IL-6/IL-10 ratio.

| Factors (P-Value) | | HR | 95% CI |
|---|---|---|---|
| Donor age (0.181) | | 1.148 | 0.938-1.406 |
| Recipient age (0.636) | | 0.926 | 0.673-1.273 |
| Primary diagnosis | IPF | 1 | — |
| | COPD (0.121) | 2.058 | 0.827-5.120 |
| | CF (0.895) | 1.089 | 0.307-3.864 |
| | PAH (0.044) | 0.099 | 0.010-0.939 |
| | A1AT (0.187) | 2.265 | 0.673-7.624 |
| Gender matching | M-M | 1 | — |
| | M-F (0.086) | 0.257 | 0.054-1.213 |
| | F-F (0.028) | 2.396 | 1.098-5.226 |
| | F-M (0.069) | 2.319 | 0.937-5.740 |
| CMV matching | D-R− | 1 | — |
| | D-R+ (0.506) | 1.359 | 0.551-3.348 |
| | D+R+ (0.142) | 1.860 | 0.813-4.258 |
| | D+R− (0.326) | 1.605 | 0.624-4.126 |
| Late new-onset DAD | (−) | 1 | — |
| | (+) (0.054) | 2.189 | 0.987-4.856 |
| Acute rejection; Grade ≥2 within 6 mo | (−) | 1 | — |
| | (+) (0.023) | 2.700 | 1.149-6.344 |
| IL-6/IL-10 ratio | ≤0.78 | 1 | — |
| | 0.78< ≤1.175 (0.007) | 2.995 | 1.352-6.637 |
| | 1.175 < (0.861) | 0.943 | 0.490-1.817 |

Example 2

Chronic lung allograft dysfunction (CLAD) remains a major cause of mortality and morbidity after transplantation. We have noted restrictive allograft syndrome (RAS) as a novel subtype of CLAD. We aimed to further characterize human CLAD subtypes by profiling damage-associated molecular pattern molecules in bronchoalveolar lavage fluid (BALF).

Materials and Methods 17 consecutively identified specimens from patients with CLAD (5 RAS, 12 bronchiolitis obliterans syndrome (BOS)) and 12 controls from patients with no CLAD were included. All the BALF specimens from CLAD cases were taken after their clinical onset. CLAD and its subtypes were defined based on pulmonary function test results. S100A8, S100A9, S100A12, S100P and high mobility group box-1 (HMGB-1) expression were measured in BALF by enzyme-linked immunosorbent assay.

Results

All of S100A8, S100A9, S100A12 and S100P were upregulated in RAS compared to controls ($p<0.005$, $p<0.005$, $p<0.01$ and $p<0.01$, respectively), whereas HMGB-1 showed no statistically significant differences. Moreover, S100A9 was upregulated in RAS compared to BOS (median 37.5 vs. 5.1 ng/mL, $p<0.05$). In contrast, S100A8 was elevated in BOS compared with controls (median 58.8 vs. 19.1 ng/mL, $p<0.05$). Neither S100A12 or S100 showed any differences in RAS vs. BOS or in BOS vs. controls.

Conclusions

In CLAD patients, we have noted a distinct difference in the expression of S100 family proteins in BALF. It appears that S100A9 is associated with RAS and not BOS. Hopefully, further characterization of molecular pathways involved in the development of CLAD subtypes will help to develop more accurate diagnostics and specifically directed therapies.

Background

Lung transplantation has become a mainstay of treatment for terminal respiratory disorders. However, chronic lung allograft dysfunction (CLAD) is the major limitation to its long-term success[1]. Survival 5 years after transplantation is only about 50%, which is significantly inferior to other solid organ transplantation[1]. Although CLAD is predominantly represented as bronchiolitis obliterans syndrome (BOS), we have noted restrictive allograft syndrome (RAS) as a novel form of CLAD[11]. RAS is a rapidly progressive disease with short survival time after its onset, showing characteristics of interstitial lung disease, while BOS (CLAD without RAS) shows relatively slow progression with minimal interstitial infiltration. Additionally, we demonstrated the pathological distinction[10]. These findings may suggest that RAS and BOS may represents different CLAD subtypes.

Development of CLAD is a complex multifactorial process, involving both adaptive immunity and innate immunity[2]. Although innate immunity has been simply thought to serve as the first line of defense against microbes, there is now increasing evidence for critical role in lung transplantation[15-17]. In addition, our proteomic analysis on bronchoalveolar lavage fluid (BALF) demonstrated that S100 calcium-binding proteins, one of the important danger signals inducing innate immune response, was expressed only in patients with CLAD, while no expression in control subjects[18].

The aim of this study is to identify the biological characteristics of RAS and BOS. In this study, expressions of S100 family proteins in 30 BALF were analyzed. We herein demonstrate distinction in S100 expression among RAS, BOS and controls.

Methods

Collection of Bronchoalveolar Lavage Fluid

Excess biological samples of BALF were collected in all patients at routine follow-up times. BALF was collected following two repeat lavages of 50 mL of normal saline solution in the right middle lobe or the lingula in lung transplant recipients. Bronchoscopies with BALF collection and transbronchial biopsy are routinely performed in the Toronto Lung Transplant Program at 2 and 6 weeks after transplantation, every 3 months for the first year, every 6 months for the second year, and thereafter, as clinically indicated. Cytological investigation was carried out on each BALF.

Aliquots of the BALF were collected and immediately snap-frozen at −80° C. After thawing, protease inhibitors (Complete Mini tabs, Boehringer-Mannheim, Germany) were added to the samples that were then clarified by centrifugation at 5000 g for 10 min. The resulting supernatants were analyzed in further step as described below.

Definition of CLAD and its Subtypes and Sample Selection

CLAD, RAS and BOS were defined as described in detail previously[11,13]. Briefly, CLAD was defined as an irreversible decline in $FEV_1$ below 80% of baseline. RAS was defined as CLAD with an irreversible decline in TLC below 90% of baseline. BOS was strictly defined as CLAD without restrictive changes of RAS.

From banked BALF specimens, samples were included in the present study if the patient had developed CLAD at the time of BALF collection. Acute rejection, overt infection, and other causes for chronic decline in FEV1 were excluded based on the definition of CLAD. Patients with CLAD with overlapped infection at the time of BALF collection were also excluded after patient selection.

ELISA

S100A8, S100A9, S100A12, S100P and high mobility group box-1 (HMGB-1) expression were measured in BALF by specific enzyme-linked immunosorbent assay kits (CircuLex S100A8, CircuLex S100A9, CircuLex S100A12, CircuLex P, CycLex, Japan, and HMGB1 ELISA Kit II, Shino-Test, Japan).

Statistical Analysis

One-way analysis of variance (ANOVA) was used for parametric data, Pearson's chi-square test for categoric data, and a Kruskal-Wallis test for nonparametric data. Values of $p<0.05$ were reported to be significant. SPSS Statistics 17.0 software (IBM, Armonk, N.Y.) for Windows (Microsoft, Redmond, Wash.) was applied.

Results

Figure 5:
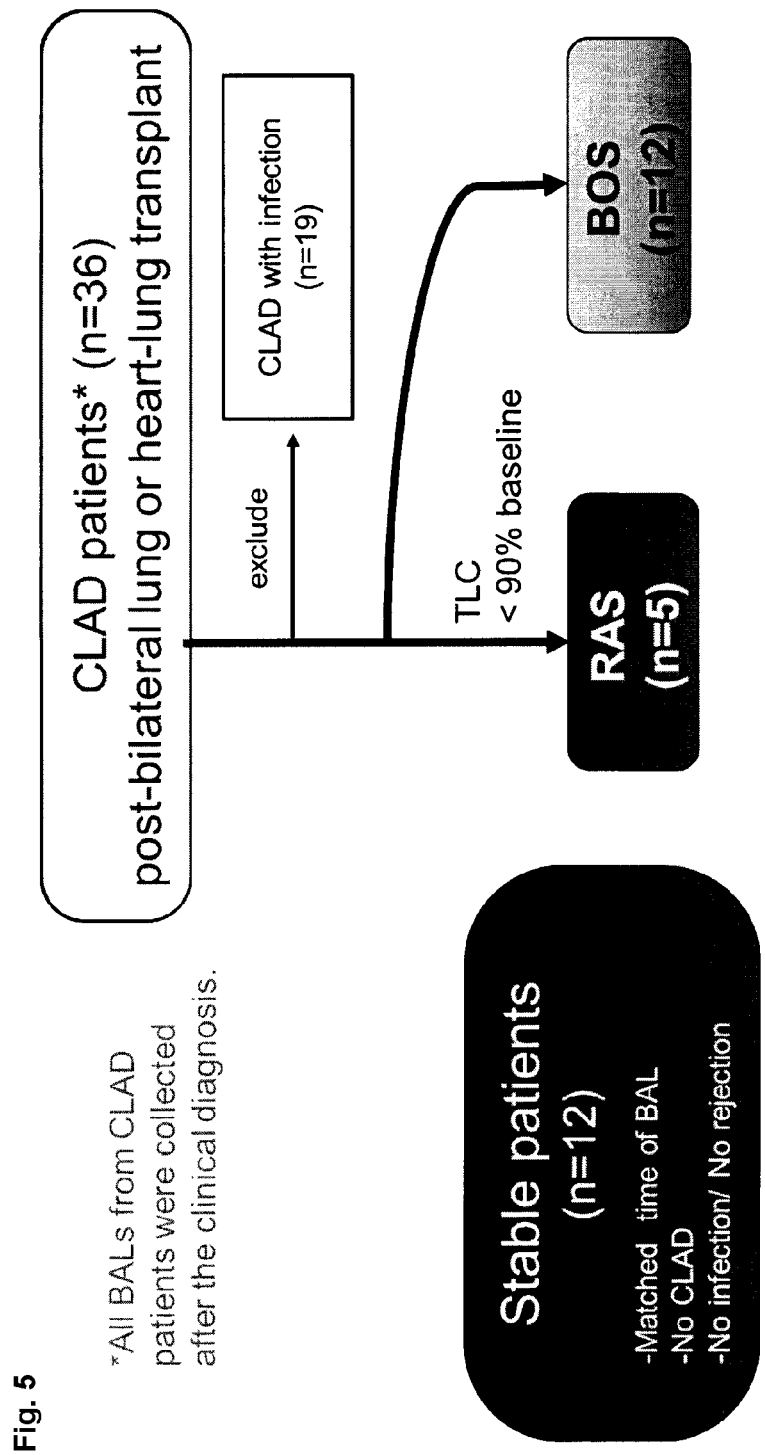
FIG. 5: Quantification of S100 family protein in bronchoalveolar lavage (BAL) fluid.

FIG. 5 summarizes the patient group included in the present study. Initially, 36 samples from CLAD were included in the study, but 19 of those were excluded because of overlapped infection. Finally, 17 consecutively identified specimens from patients with CLAD (5 RAS and 12 BOS) and 12 controls from patients with no CLAD and matched time of bronchoscopy were included in this study.

Patient demographics are described in Table 4. There was no significant difference in clinical background among RAS, BOS and stable controls except for immunosuppressive regimen and azithromycin administration.

BALF cytology and histology in the concurrent TBLB are shown in Table 5. Notably, BOS was associated with "no abnormal findings" which was not found in RAS.

Figure 6A:
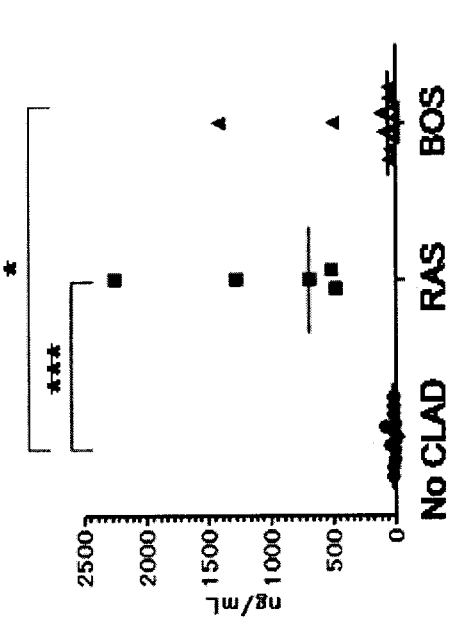
FIGS. 6A-B is a series of graphs showing S100 family protein in BAL.
Figure 6A:
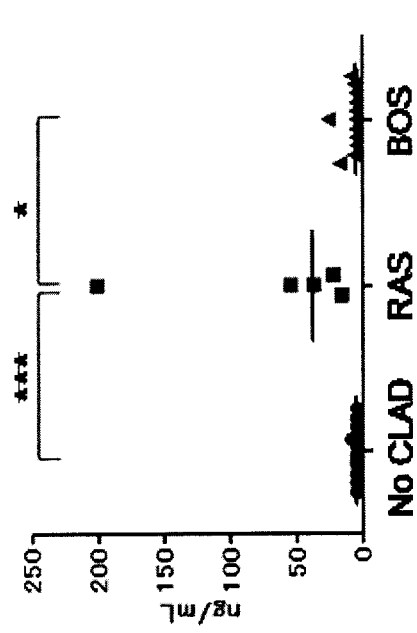
Figure 6B:
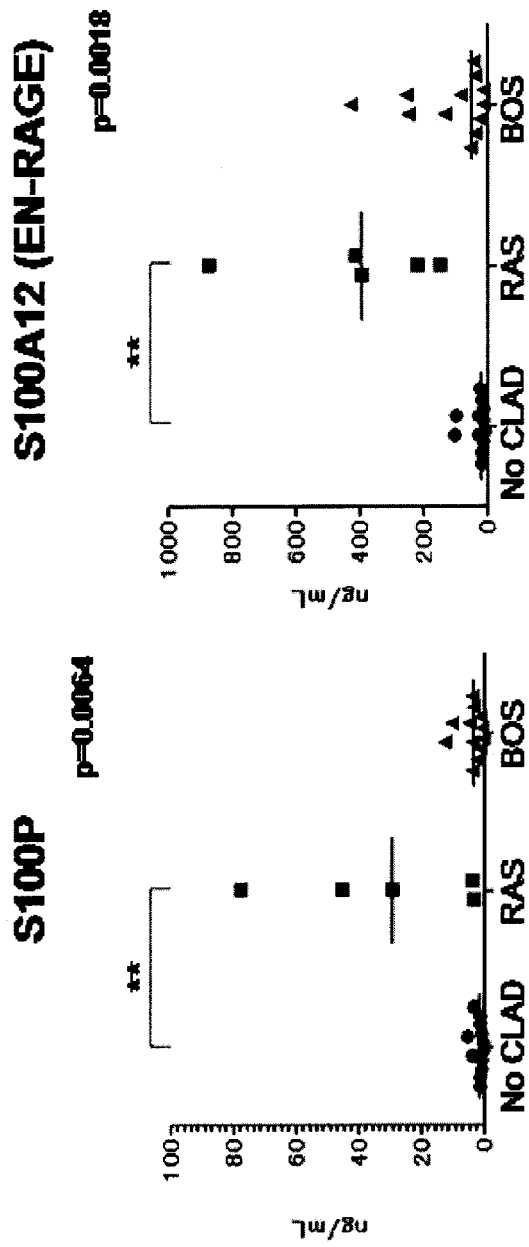

Expressions of S100 family in BALF are demonstrated in FIG. 6. All of S100A8, S100A9, S100A12 and S100P were upregulated in RAS compared to controls ($p<0.005$, $p<0.005$, $p<0.01$ and $p<0.01$, respectively), whereas HMGB-1 did not show any statistically significant difference (FIG. 6). Moreover, S100A9 showed higher expression in RAS compared to BOS (median 37.5 vs. 5.1 ng/mL, $p<0.05$). On the other hand, S100A8 was elevated in BOS compared with controls (median 58.8 vs. 19.1 ng/mL, $p<0.05$). Neither S100A12 or S100 showed any differences in RAS vs. BOS or, in BOS vs. controls.

To assess diagnostic accuracy, receiver operating characteristic (ROC) curves are analyzed. Area under the ROC curves are 0.95 [95% CI, 0.85-1.05] in differentiating RAS from BOS by S100A9 and 0.89 [95% CI, 0.78-1.01] in differentiating CLAD from No CLAD by S100A8 (FIG. 7).

TABLE 3

Differential proteomic analysis of bronchoalveolar lavage fluid from lung transplant patients with and without chronic graft dysfunction RAS subtype.

| S100 family | No CLAD | | | CLAD(RAS) | | |
|---|---|---|---|---|---|---|
| Protein S100-A9 | 0 | 0 | 0 | 1 | 7 | 6 |
| Protein S100-A8 | 0 | 0 | 0 | 1 | 5 | 5 |
| Protein S100-A12 | 0 | 0 | 0 | 4 | 3 | 4 |
| Protein S100-P | 0 | 0 | 0 | 1 | 3 | 3 |

TABLE 4

Patient characteristics

| variable | Stable (n = 12) | RAS (n = 5) | BOS (n = 12) | P value |
|---|---|---|---|---|
| Age at transplant, yr | 60 (47-63) | 53 (44-56) | 42 (33-54) | 0.186 |
| Gender (M/F) | 7/5 | 3/2 | 9/3 | 0.776 |
| Type (double lung/heart-lung) | 10/2 | 5/0 | 11/1 | 0.603 |
| Primary diagnosis | | | | 0.264 |
| COPD | 3 | 2 | 0 | |
| IPF | 2 | 1 | 4 | |
| Cystic fibrosis | 2 | 0 | 4 | |
| Bronchiectasis | 2 | 1 | 0 | |
| Others | 3 | 1 | 4 | |
| Immunosuppressive Tx | | | | |
| Steroids | 12 | 5 | 12 | — |
| FK506/CSA | 6/6 | 5/0 | 10/2 | 0.035 |
| AZA/MMF | 8/4 | 1/4 | 6/6 | 0.199 |
| Azithromycin Tx at BAL | 1 | 1 | 10 | <0.0001 |
| Gender combination mismatch | 2 | 2 | 3 | 0.534 |
| CMV mismatch | 5 | 3 | 4 | 0.586 |
| Timing of BAL, months post-op | 24 (23-25) | 41 (31-50) | 27 (24-52) | .0123 |

TABLE 5

Characteristics in BAL

| Findings | Stable (n = 12) | RAS (n = 5) | BOS (n = 12) | P value | RAS vs BOS |
|---|---|---|---|---|---|
| Cytology | | | | | |
| Acute inflammation | 0 | 4 | 3 | 0.0027 | 0.101 |
| Acute and chronic inflammation | 0 | 1 | 2 | 0.2735 | 1.000 |
| Chronic inflammation | 2 | 0 | 0 | 0.2463 | — |
| No abnormal findings | 10 | 0 | 7 | 0.0012 | 0.041 |
| Histology (rejection score) | | | | | |
| Grade 0 | 6 | 3 | 7 | | |
| Grade 1 | 1 | 0 | 2 | | |
| N/A or suboptimal sampling | 5 | 2 | 3 | | |
| Colonization | | | | 0.316 | |
| Gram negative bacterium | 2 | 0 | 4 | | |
| Fungus | 1 | 0 | 2 | | |
| None | 9 | 5 | 6 | | |

TABLE 6

Candidate Biomarkers for CLAD

| Sample source | Potential marker | | Endpoint | N |
|---|---|---|---|---|
| Donor lung (CIT) | IL-6/IL-10 ratio | mRNA | Predict BOS | 121 |
| BAL (post-diagnosis) | S100A9 | Protein | Distinguish RAS from No CLAD, Distinguish RAS from BOS | 30 |
| | S100A8 | Protein | Distinguish RAS from No CLAD, Distinguish BOS from No CLAD | 30 |

Example 4

The long-term success of lung transplantation is limited by chronic lung allograft dysfunction (CLAD). This study investigated the alveolar alarmin profiles in CLAD subtypes, restrictive allograft syndrome (RAS) and bronchiolitis obliterans syndrome (BOS). Bronchoalveolar lavage (BAL) samples were collected from 53 recipients who underwent double lung or heart-lung transplantation, including patients with RAS (n=10), BOS (n=18) and No CLAD (n=25). Protein levels of alarmins such as S100A8, S100A9, S100A8/A9, S100A12, S100P, high-mobility group box 1 (HMGB1) and soluble receptor for advanced glycation end products (sRAGE) in BAL fluid were measured. RAS and BOS showed higher expressions of S100A8, S100A8/A9 and S100A12 compared to No CLAD (p<0.0001, p<0.0001, p<0.0001 in RAS vs. No CLAD, p=0.0006, p=0.0044, p=0.0086 in BOS vs. No CLAD, respectively). Moreover, RAS showed greater up-regulation of S100A9, S100A8/A9, S100A12, S100P and HMGB1 compared to BOS (p=0.0094, p=0.038, p=0.041, p=0.035 and p=0.010, respectively). sRAGE did not show significant difference among the three groups (p=0.174). Our results demonstrate distinct expression patterns of alveolar alarmins in RAS and BOS, suggesting that RAS and BOS may represent biologically different subtypes.

Chronic lung allograft dysfunction (CLAD) is a major cause of morbidity and mortality in long-term survivors of lung transplantation. The five-year survival rate associated with a functioning lung allograft is ~50%, which is considerably inferior to other solid organ transplantation[1]. Recently, we described a novel form of CLAD, restrictive allograft syndrome (RAS) that shows a rapid progression with pathological diagnoses of diffuse alveolar damage and pleuroparenchymal fibroelastosis, which is distinct from bronchiolitis obliterans syndrome (BOS)—the conventional form of CLAD [2,3]. These clinical and pathological distinctions lead to our hypothesis that RAS and BOS may represent biologically different CLAD subtypes. Biologic profiling of CLAD phenotypes may subsequently help to understand the underlying mechanisms and to ultimately develop precisely targeted and personalized therapy.

Accumulating evidence suggests that multiple immune system may contribute to the pathogenesis of CLAD[4]. Notably, the importance of innate immunity in the CLAD development has gained significant prominence. In fact, many of the identified risk factors of CLAD, such as primary graft dysfunction, cytomegalovirus (CMV) pneumonitis, gastroesophageal-reflux, and polymorphism in toll-like receptors would likely activate the innate immune response[4,5]. The innate immunity of the lung is reliant on recognition of an array of danger signals including damage-associated molecular patterns, also referred to as 'alarmins'—intracellular constitutive molecules that can turn into pro-inflammatory mediators once extracellularly released[6,7]. Intriguingly, our preliminary proteomic study revealed that several alarmins, such as S100 family proteins, were expressed in the bronchoalveolar lavage (BAL) fluid of patients who developed RAS, but not in those of CLAD-free recipients[8], suggesting that the alveolar release of alarmins may play a role in the RAS development. However, it remains unclear whether alveolar alarmins are uniformly associated with both RAS and BOS.

Human CLAD was characterized by profiling protein expressions of alarmins such as S100 family proteins (S100A8, S100A9, S100A8/A9 heterodimer and polymer complex, S100A12 and S100P), high-mobility group box 1 (HMGB1) and their decoy receptor, soluble form of receptor for advanced glycation end products (sRAGE) in BAL fluid.

Materials and Method
Study Population

Figure 8:
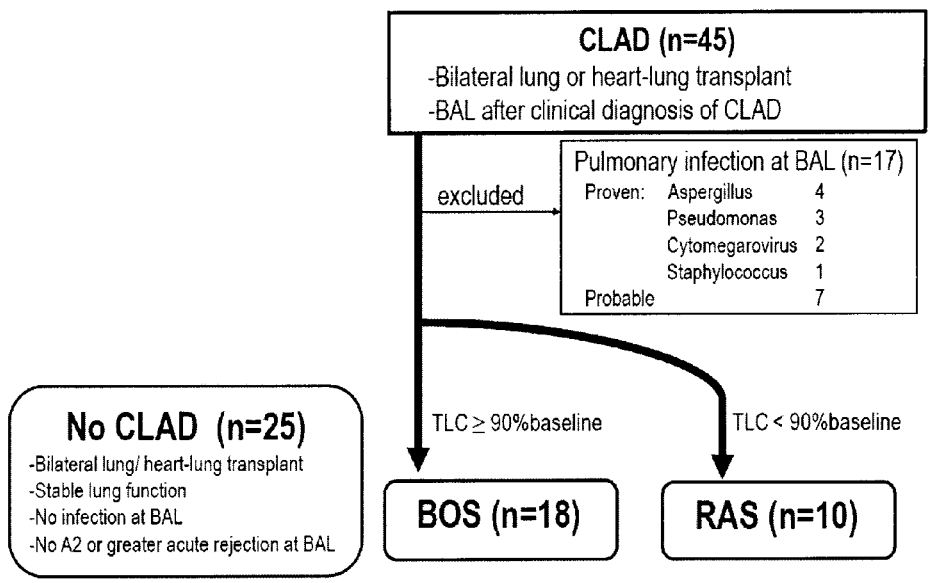
FIG. 8: Study population distribution. From banked bronchoalveolar lavage (BAL) samples, we initially identified 45 post-bilateral lung or heart-lung transplant recipients who developed CLAD prior to BAL. 17 cases were excluded due to overlapped proven or probable pulmonary infection. 10 RAS cases and 18 BOS cases were included in the study. All the BAL samples were collected after the diagnosis of RAS or BOS. We also included 25 post-double lung or heart-lung transplant recipients who showed stable lung function by the end of the observation period and no evidence of pulmonary infection or Grade A2-4 acute rejection at BAL. We selected BAL samples of No CLAD obtained more than 18 months after lung transplantation in order to match the interval between lung transplantation and BAL in No CLAD with RAS and BOS. BAL, bronchoalveolar lavage; BOS, bronchiolitis obliterans syndrome; CLAD, chronic lung allograft dysfunction; RAS, restrictive allograft syndrome; TLC, total lung capacity.

Designation of the study population is summarized in FIG. 8. From banked BAL specimens, samples were selected dependent on whether the post-bilateral lung or heart-lung transplant recipient developed CLAD prior to BAL. Through chart review, we initially identified 45 subjects with CLAD, of which 17 cases were excluded because of concurrent proven or probable pulmonary infection at the time of BAL, compliant with the International Society for Heart and Lung Transplantation (ISHLT) consensus statement[9]. In all, 28 samples from 28 patients identified with CLAD (10 with RAS and 18 with BOS) were included. Additionally, we included 25 post-bilateral lung or heart-lung transplant recipients with stable lung function as 'No CLAD' controls, matching the interval between lung transplantation and BAL with that of CLAD group.

Post-Transplant Follow-Up, Immunosupression and Treatment for CLAD

Standard post-transplant care was provided as previously described[10]. The lung transplant program employed cyclosporine A, azathioprine and prednisone as initial standard regimen[10] treatment for CLAD.

Post-transplant follow-up, immunosuppression and treatment for CLAD

BAL and transbronchial lung biopsies (TBBxs) were scheduled at 2 and 6 weeks and 3, 6, 9, 12, 18 and 24 months after lung transplantation and when clinically indicated[11]. Our lung transplant program employed cyclosporine A, azathioprine and prednisone as initial standard regimen_EN-REF_2_10. In brief, cyclosporin A was replaced with tacrolimus in patients who experience cyclosporine toxicity or who develop recurrent acute rejection with adequate cyclosporine levels. Mycophenolic acid or mycophenolate mofetil is used in patients with anti-HLA antibodies, patients who did not tolerate azathioprine or who developed recurrent rejection on azathioprine. When patients develop CLAD, they are routinely switched from cyclosporine A to tacrolimus, and thrice weekly azithromycin is implemented. A switch from azathioprine to mycophenolic acid is also considered.

Collection of Bronchoalveolar Lavage (BAL) Fluid

BAL fluid was collected and processed as described previously[11]. The quantity of recovered BAL fluid was greater than 30 mL of 100 mL-instillation in all 53 subjects except for one case with RAS.

BAL Cytology and Transbronchial Lung Biopsy (TBBx) Histology

Inflammation in BAL samples was semi-quantitatively assessed by a cytopathologist and described as follows; neutrophil-predominant (neutrophils >10% of 200 counted cells in the specimen), lymphocyte-predominant (lymphocytes >10%), mixed-type (a mix of neutrophils and lymphocytes >10%), or no inflammatory findings. Acute rejection was evaluated in the concomitant transbronchial lung biopsy (TBBx) specimen by pathologists based on the ISHLT grading system[12].

Measurement of Protein Expressions

Protein expression of S100A8, S100A9, S100A8/A9 heterodimer and polymer complex, S100A12, S100P, HMGB1 and sRAGE was measured in BAL supernatant by using specific enzyme-linked immunosorbent assay kits (S100A8, S100A9, S100A12, S100P, sRAGE, CycLex, Nagano, Japan; S100A8/A9, ALPCO, NH, USA; HMGB1, Shino-Test, Tokyo, Japan), following manufacturers' instructions.

Definition of CLAD, RAS, BOS and Acute Exacerbation
Statistical Analysis

The goal was to identify the relationship between alarmin profiles of CLAD phenotypes using post-transplant BAL samples. ANOVA, Kruskal-Wallis test and Fisher's exact test were performed to determine differences among patients with RAS, BOS and No CLAD. Mann-Whitney test was applied to compare the timing of BAL relative to the onset of RAS and BOS. $P<0.05$ were reported to be significant. To report diagnostic accuracy in differentiating CLAD from No CLAD or RAS from BOS, receiver operating characteristic (ROC) curves were constructed and the area under the ROC curve was calculated for the S100 proteins and HMGB1. GraphPad Prism version 6.02 for Windows (GraphPad Software, San Diego, Calif., Microsoft, Redmond, Wash., USA) was applied.

Results

Clinical characteristics of the study population are shown in Table 7. Recipient age at transplantation was significantly different among RAS, BOS and No CLAD (p=0.047), but paired post-tests between each group did not reach statistical significance (p=0.091 in No CLAD vs. BOS; p=0.189 in No CLAD vs. RAS; p>0.999 in BOS vs. RAS). However, patients with CLAD were significantly younger than those with No CLAD (p=0.013). No significant difference in primary diagnosis, transplantation type, gender matching or CMV serology matching were found among the three study groups. The median post-transplant follow-up in RAS, BOS and No CLAD were 39, 50 and 47 months (p=0.373). The median interval between lung transplantation and BAL in RAS, BOS and No CLAD were 36, 27 and 24 months (p=0.417). The median interval between disease onset of RAS or BOS and BAL were 165 and 38 days, which did not show significant difference (p=0.292). Three samples of RAS and two of BOS were collected during acute exacerbation of the disease, of which incidence did not show significant difference (p=0.315). Differences in pulmonary function test results were compatible with the definition of CLAD and its subtypes, but RAS and BOS did not show significant difference in forced expiratory volume in one second (mean, 50.3% baseline vs. 58.4% baseline, p=0.107). Tacrolimus and azithromycin administration were more common in patients with RAS and BOS compared to No CLAD (tacrolimus, p=0.0082 for RAS vs. No CLAD, p=0.0059 for BOS vs. No CLAD; azithromycin, p=0.0008 in RAS vs. No CLAD, p<0.0001 in BOS vs. No CLAD). There was no significant difference in the use of tacrolimus and azithromycin between RAS and BOS (p>0.999 and p=0.147).

Concurrent pathologic and microbiologic findings are summarized in Table 8. Cytopathological assessment was performed on all but one insufficient BAL specimen from a No CLAD patient. Neutrophil-predominant inflammation was frequently found in CLAD compared to No CLAD (p=0.0047) and in RAS compared to BOS and No CLAD (p=0.026 and p=0.0002). There was a greater tendency for neutrophil-predominant inflammation in BOS compared to No CLAD, but it did not reach statistical significance (p=0.054). Adequate TBBx sampling were achieved in 40.0% (4 of 10) of RAS, 66.7% (12 of 18) of BOS and 84.0% (21 of 25) of No CLAD cases, which showed significant difference between RAS and No CLAD (p=0.043), but not between RAS and BOS or between BOS and No CLAD (p=0.091 and p=0.207). No significant difference was observed in the acute rejection scores and in positivity in cultures for bacteria, acid-fast bacilli or *Aspergillus* across the three study groups. BAL specimens were also analyzed for CMV in 11 specimens (1 RAS, 4 BOS and 6 No CLAD), all of which showed negative results.

Protein levels of the S100 proteins, HMGB1 and sRAGE in BAL fluid are presented in FIGS. 9A-F and Table 10. S100A8, S100A8/A9 and S100A12 showed higher expressions in RAS and BOS compared with No CLAD (FIGS. 9A, 9C and 9D) (p<0.0001, p<0.0001 and p<0.0001 for S100A8, S100A8/A9 and S100A12 between RAS and No CLAD; p=0.0006, p=0.0044 and p=0.0086 for S100A8, S100A8/A9 and S100A12 between BOS and No CLAD). Moreover, up-regulation of S100A8/A9 and S100A12 were significantly greater in RAS compared to BOS (p=0.038 and p=0.041, respectively). Furthermore, RAS showed significantly higher expression of S100A9, S100P and HMGB1 (FIGS. 9B, 9E and 9F) compared to BOS and No CLAD (p=0.0094, p=0.035 and p=0.010 for S100A9, S100P and HMGB1 between RAS and BOS; p<0.0001, p<0.0001 and p=0.0018 for S100A9, S100P and HMGB1 between RAS and No CLAD). sRAGE (FIG. 9G) did not show any significant differences across the three study groups (p=0.174).

Area under the ROC curves are summarized in Table 9. S100A8 showed high accuracy in differentiating CLAD from No CLAD (AUC, 0.921; 95% confidence interval [CI], 0.853-0.990). S100A9 (AUC, 0.813; 95% CI, 0.698-0.927), S100A8/A9 (AUC, 0.889; 95% CI, 0.802-0.977) and S100A12 (AUC, 0.870; 95% CI, 0.774-0.966) showed moderate accuracy in predicting CLAD vs. No CLAD. As a biomarker differentiating RAS form BOS, S100A9 (AUC, 0.889; 95% CI, 0.762-1.016), S100A8/A9 (AUC, 0.889; 95% CI, 0.763-1.015), S100A12 (AUC, 0.867; 95% CI, 0.730-1.003) and HMGB1 (AUC, 0.833; 95% CI, 0.674-0.992) showed moderate accuracy.

Discussion

It has been recognized that CLAD is not a single entity, but rather a heterogenous one[4,14,15]. For better understanding of CLAD, several sub-phenotypes such as RAS[3], neutrophilic reversible allograft dysfunction, fibroproliferative BOS and early-onset BOS have been proposed[15]. Among them, RAS has been established as a widely accepted subtype of CLAD[15-17]. We initially proposed RAS as a novel form of CLAD for (1) its restrictive physiology that does not fit the original ISHLT definition of BOS[14], (2) its prevalence of 25-35% of all CLAD[3,17], and (3) its clinical and pathological distinctions from BOS[2,3,13,17]. The heterogeneity of CLAD might be attributed to multiple immunopathological mechanisms underlying the pathogenesis[4]; therefore, biologic profiling of RAS and BOS in turn may help to better understand CLAD.

Neutrophil-predominant inflammation was common in BAL samples of CLAD compared with No CLAD (Table 8). Although our semi-quantitative criteria for evaluating inflammation may limit generalizability and comparability, the results might further support previous findings describing the association between BAL neutrophilia and CLAD[17,18]. Intriguingly, neutrophil-predominant inflammation in BAL cytology was more common in RAS than in BOS. Since we excluded CLAD with pulmonary infection, combined with the result that all BAL from RAS patients showed negative culture results, the increase of neutrophils in BAL sample might be likely associated with RAS rather than possible concomitant infection. Activated neutrophils may contribute to the development of CLAD, especially RAS, by degrading extracellular matrix, depleting antioxidant defense and promoting fibroblast proliferation[18].

Figure 9A:
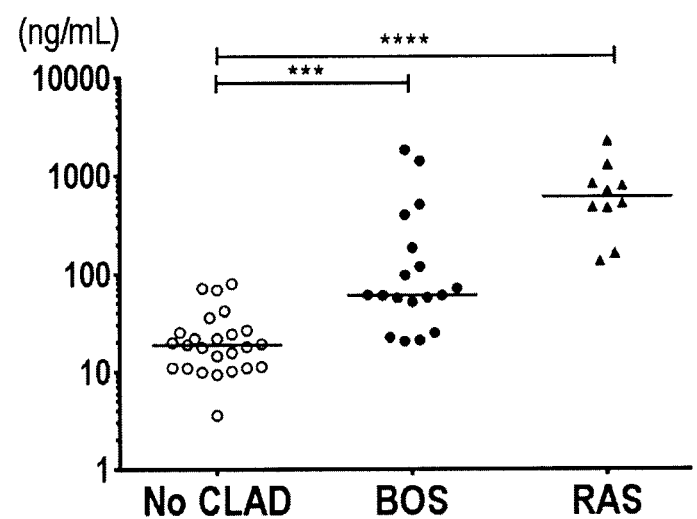
FIGS. 9A-G is a series of graphs showing the protein expressions of the S100 family proteins, HMGB1 and sRAGE in bronchoalveolar lavage fluid.

RAS and BOS seem to share similar up-regulation of S100A8, S100A8/A9 and S100A12 in BAL fluid (FIGS. 9A; 9C and 9D and Table 10). S100 proteins are a family of 10-12 kD calcium-binding proteins. S100A8, S100A9, S100A8/A9, S100A12 can be released from activated neutrophils, monocytes/macrophages and necrotic cells[7,19]. Extracellular S100 proteins ultimately lead to innate immune responses such as leukocyte recruitment and endothelial cell activation[19]. S100A8, S100A8/A9 and S100A12 may contribute to the development of both RAS and BOS by activating innate immune-dependent mechanisms. Considering the finding that RAS showed further up-regulation of alveolar S100A8/A9 and S100A12 compared to BOS (FIGS. 9C and 9D), S100A8/A9 and S100A12 might be more associated with RAS development.

Figure 9B:
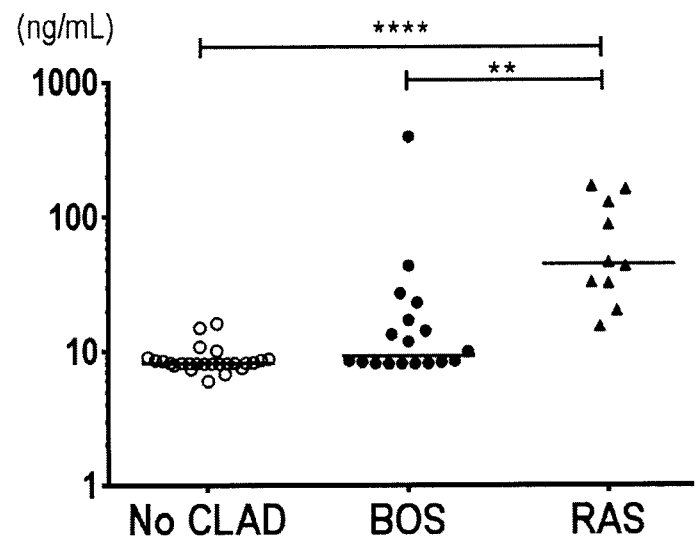
Figure 9C:
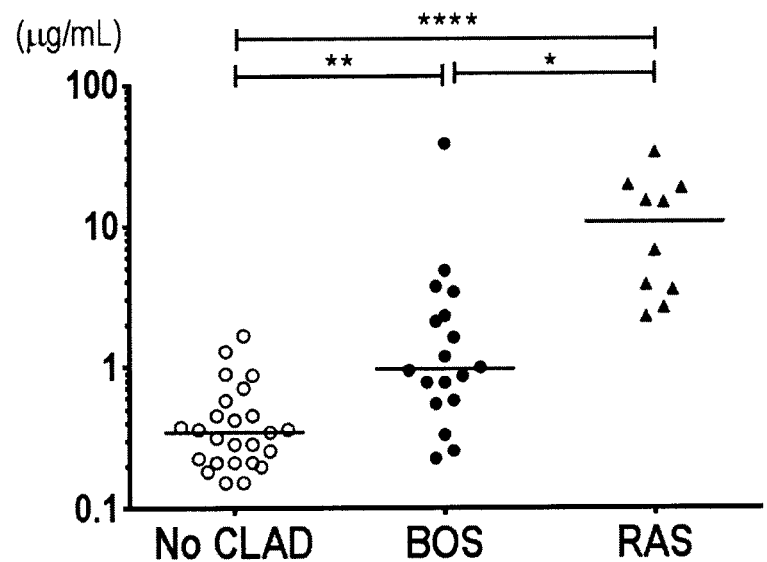
Figure 9D:
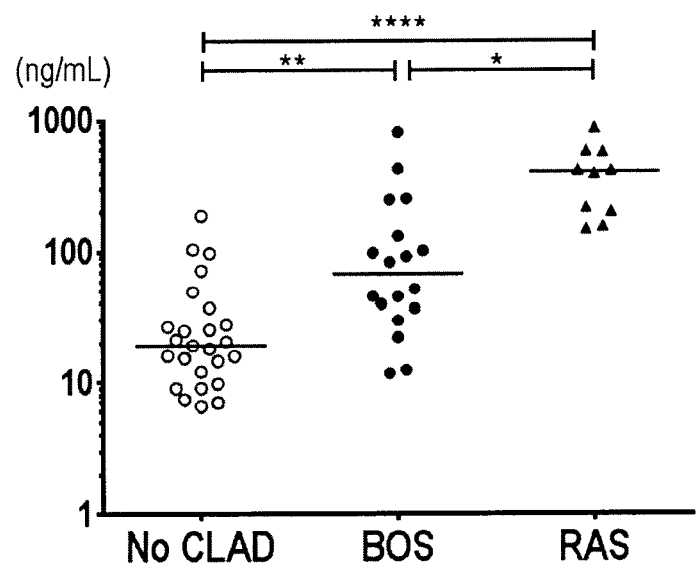
Figure 9E:
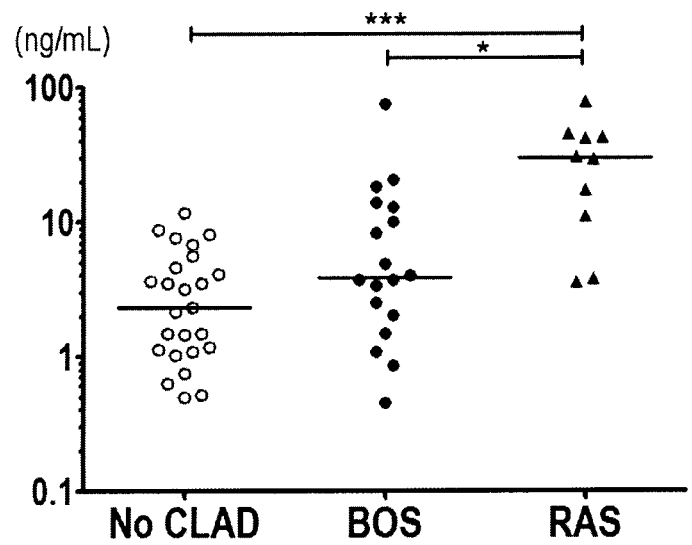
Figure 9F:
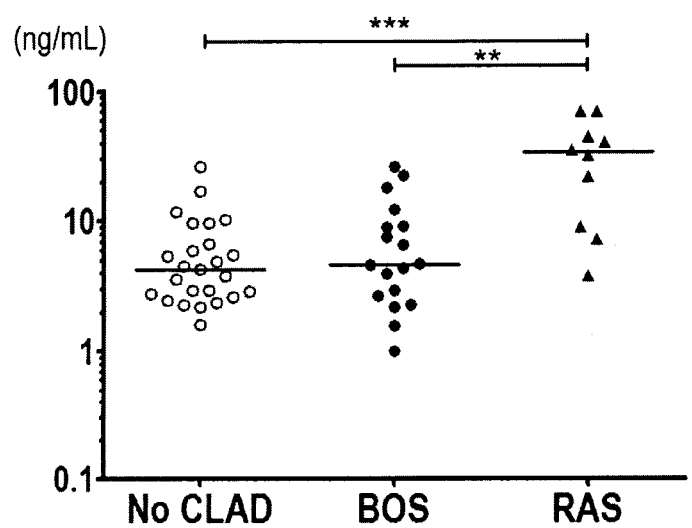
Figure 9G:
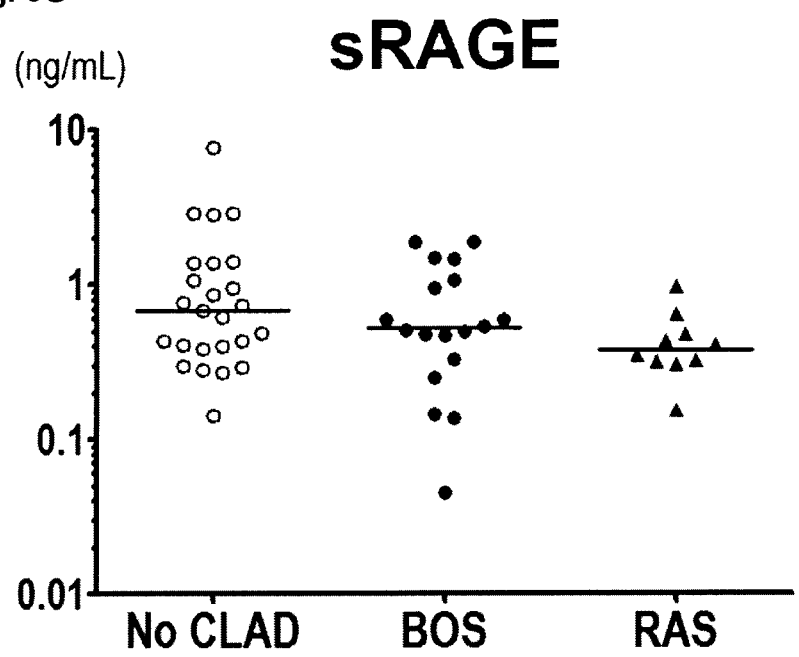

Strikingly, up-regulation of alveolar S100A9, S100P and HMGB1 were observed exclusively in RAS (FIGS. 9B, 9E and 9F and Table 10). Thus, S100A9 may contribute to pulmonary parenchymal fibrosis in RAS. Although the role of S100P in the context of pulmonary pathophysiology is not yet well understood, its potent function in mediating cell proliferation, metastasis and invasion may contribute to RAS development[21]. HMGB1 is a ubiquitous 30-kD DNA-binding nuclear protein that can be released from activated monocytes/macrophages, natural killer cells, mature myeloid dendritic cells and necrotic or apoptotic cells[7,22].

In contrast to S100s and HMGB1, alveolar sRAGE did not show significant differences among RAS, BOS and No CLAD (FIG. 9G and Table 10). sRAGE is a 48-kD C-terminally truncated RAGE and could be released via proteolytic cleavage of full-length membrane-bound RAGE expressed by alveolar type I epithelial cells during tissue injury (i.e. ALI/ARDS)[26]. For example, eosinophil cationic protein, implicated in the breakdown of sRAGE, is reportedly up-regulated in the BAL fluid of lung transplant recipients[27,28].

Specifically, S100A9 and S100A8/A9 appear to be useful to differentiate RAS from BOS, while S100A8 and S100A8/A9 appear to distinguish CLAD from No CLAD (Table 9). The data reported here was generated via a cross-sectional study. Longitudinal observation for the biomarkers can be used to reveal temporal dynamics as well as the predictive values. Through longitudinal observation, RAS and BOS seemed to show different pattern in alveolar alarmin expressions over time; sharp increase and plateau about 3 months prior to the onset in RAS, and temporal decrease and rapid increase in BOS.

The results identified distinct expression patterns of alveolar alarmins in RAS and BOS, supporting the contention that RAS and BOS may represent biologically different subtypes of CLAD. The goal is to predict CLAD and to delineate its subtypes more accurately.

TABLE 7

Demographics of 53 lung transplant patients.

| Characteristics | No CLAD (n = 25) | BOS (n = 18) | RAS (n = 10) | p-value |
|---|---|---|---|---|
| Recipient age at transplant, yr | 53 [48-64] | 42 [32-58] | 45 [37-54] | 0.047 |
| Primary diagnosis, (%) | | | | |
| Chronic obstructive pulmonary disease | 4 (16.0) | 2 (11.1) | 1 (10.0) | 0.917 |
| Idiopathic pulmonary fibrosis | 8 (32.0) | 6 (33.3) | 3 (30.0) | |
| Cystic fibrosis | 3 (12.0) | 5 (27.8) | 2 (20.0) | |
| Others | 10 (40.0) | 5 (27.8) | 4 (40.0) | |
| Transplant type, (%) | | | | |
| Bilateral lung | 22 (88.0) | 17 (94.4) | 10 | 0.659 |
| Heart-lung | 3 (12.0) | 1 (5.6) | — | |
| Gender matching, (%) | | | | |
| Male to Male | 10 (40.0) | 10 (55.6) | 4 (40.0) | 0.260 |
| Male to Female | 2 (8.0) | — | 3 (30.0) | |
| Female to Female | 9 (36.0) | 5 (27.8) | 1 (10.0) | |
| Female to Male | 4 (16.0) | 3 (16.7) | 2 (20.0) | |
| CMV serology matching, (%) | | | | |
| Donor −/Recipient − | 11 (44.0) | 6 (33.3) | 1 (10.0) | 0.182 |
| Donor −/Recipient + | 8 (32.0) | 4 (22.2) | 4 (40.0) | |
| Donor +/Recipient + | 5 (20.0) | 3 (16.7) | 2 (20.0) | |
| Donor +/Recipient − | 1 (4.0) | 5 (27.8) | 3 (30.0) | |
| Timing of BAL, | | | | |
| From transplantation to BAL, months | 24 [23-24] | 27 [21-61] | 36 [12-73] | 0.417 |
| Immunosuppression/treatment for CLAD | | | | |
| CsA/FK506 | 18/7 | 5/13†† | 2/8### | 0.0028 |
| AZA/MMF/MPA | 13/11/1 | 9/6/3 | 4/5/1 | 0.626 |
| Prednisone | 25 | 18 | 10 | — |
| Azithromycin | 1 | 16††† | 6### | <0.0001 |
| Pulmonary function at BAL | | | | |
| $FEV_1$, % baseline | 96.7 ± 5.6 | 58.4 ± 17.2†††† | 50.3 ± 14.9**** | <0.0001 |
| TLC, % baseline | 98.4 ± 3.9 | 102.8 ± 8.7† | 78.6 ± 8.5****,#### | <0.0001 |

Non-parametric continuous variables are expressed as median [interquartile range]. Parametric continuous variables are expressed as mean ± standard deviation. P values were calculated by the Fisher's exact test for categoric variables. Kruskal-Wallis ANOVA was applied for non-parametric continuous variables and one-way ANOVA was used for parametric continuous variables for No CLAD vs. BOS vs. RAS. Mann-Whitney test was applied for timing for BAL from the onset of BOS and RAS.
†$p < 0.05$, ††$p < 0.01$, and ††††$p < 0.0001$ in BOS vs. No CLAD;
$p < 0.01$, ###$p < 0.001$, and ####$p < 0.0001$ in RAS vs. No CLAD;
****$p < 0.0001$ in BOS vs RAS.
BAL, bronchoalveolar lavage;
BOS, bronchiolitis obliterans syndrome;
CLAD, chronic lung allograft dysfunction;
RAS, restrictive allograft syndrome;
CMV, cytomegalovirus;
COPD, chronic obstructive pulmonary disease;
FEV1, forced expiratory volume in one second;
TLC, total lung capacity.

TABLE 8

Concurrent pathologic and microbiologic findings.

| | No CLAD | BOS | RAS | p-value |
|---|---|---|---|---|
| Cytology on BALF, (%) | | | | |
| Acute inflammation | 2/24 (8.3) | 5/18 (27.8) | 8/10 (80.0)***,# | 0.0003 |
| Mixed inflammation | — | 2/18 (11.1) | — | |
| Chronic inflammation | 3/24 (12.5) | — | — | |
| No abnormal findings | 19/24 (79.2) | 11/18 (61.1) | 2/10 (20.0) | |
| Histology on TBLB, (%) | | | | |
| Acute rejection Grade X | — | — | 1/5 (20.0) | 0.195 |
| Grade 0 | 19/21 (90.5) | 10/12 (83.3) | 3/5 (60.0) | |
| Grade 1 | 2/21 (9.5) | 2/12 (16.7) | 1/5 (25.0) | |

TABLE 8-continued

Concurrent pathologic and microbiologic findings.

|  | No CLAD | BOS | RAS | p-value |
|---|---|---|---|---|
| Microbiology on BALF, (%) | | | | |
| Positive bacterial culture | 2/25 | 2/18 | 0/10 | 0.816 |
|  | P. Aeruginosa: 1 | P. aeruginosa: 1 | | |
|  | S. Maltophilia: 1 | H. influenzae: 1 | | |
| Positive acid-fast bacilli culture | 0/25 | 0/18 | 0/10 | — |
| Positive Aspergillus culture | 0/25 | 1/18 | 0/10 | 0.528 |

P values were calculated by the Fisher's exact test.
***$p < 0.001$ in RAS vs. No CLAD and #$p < 0.05$ in RAS vs. BOS.
BALF, bronchoalveolar lavage fluid;
BOS, bronchiolitis obliterans syndrome;
CLAD, chronic lung allograft dysfunction;
RAS, restrictive allograft syndrome;
TBLB, transbronchial lung biopsy.

TABLE 9

Diagnostic accuracy for the S100 family proteins and HMGB1.

| | Area under the ROC curve, (95% confidence interval) | |
|---|---|---|
| Protein | CLAD vs. No CLAD | RAS vs. BOS |
| S100A8 | 0.921 (0.853-0.990) | — |
| S100A9 | 0.813 (0.698-0.927) | 0.889 (0.762-1.016) |
| S100A8/A9 heterocomplex | 0.889 (0.802-0.977) | 0.889 (0.763-1.015) |
| S100A12 | 0.870 (0.774-0.966) | 0.867 (0.730-1.003) |
| S100P | 0.761 (0.633-0.890) | 0.817 (0.651-0.982) |
| HMGB1 | 0.665 (0.517-0.813) | 0.856 (0.702-1.009) |

BOS, bronchiolitis obliterans syndrome;
CLAD, chronic lung allograft dysfunction;
HMGB1, high-mobility box group 1;
RAS, restrictive allograft syndrome;
ROC, receiver-operating characteristic.

TABLE 10

Protein expressions in bronchoalveolar lavage fluid.

| Protein | No CLAD (n = 25) Median, [IQR] | BOS (n = 18) Median, [IQR] | RAS (n = 10) Median, [IQR] | p-value |
|---|---|---|---|---|
| Alarmins | | | | |
| S100A8, ng/mL | 18.9 [11.0-25.9] | 60.5 [44.9-238.5]††† | 607.8 [393.8-947.0]**** | <0.0001 |
| S100A9, ng/mL | 8.2 [8.1-8.7] | 9.3 [8.2-18.6] | 44.7 [29.4-137.4]****,## | <0.0001 |
| S100A8/A9, μg/mL | 0.35 [0.21-0.52] | 0.97 [0.57-2.6]†† | 10.7 [3.3-18.8]****,# | <0.0001 |
| S100A12, ng/mL | 19.2 [11.0-32.5] | 67.5 [35.0-160.5]†† | 404.0 [190.6-578.5]****,# | <0.0001 |
| S100P, ng/mL | 2.3 [1.1-5.1] | 3.9 [1.9-13.2] | 30.0 [9.2-43.0]****,# | 0.0002 |
| HMGB1, ng/mL | 4.2 [2.7-8.2] | 4.6 [2.6-10.0] | 33.5 [8.5-50.5]****,## | 0.001 |
| sRAGE, ng/mL | 0.68 [0.39-1.4] | 0.52 [0.31-1.2] | 0.38 [0.31-0.52] | 0.174 |

Non-parametric continuous variables are expressed as median [interquartile range]. P values were calculated by the Kruskal-Wallis ANOVA with Dunn's post-tests.
Adjusted p-values are: ††$p < 0.01$, †††$p < 0.001$ in BOS vs. No CLAD; ****$p < 0.0001$ in RAS vs. No CLAD; #$p < 0.05$, ##$p < 0.01$ in BOS vs. RAS.
BOS, bronchiolitis obliterans syndrome;
CLAD, chronic lung allograft dysfunction;
HMGB1, high-mobility box group 1;
RAS, restrictive allograft syndrome;
sRAGE, soluble receptor for advanced glycation end products.

Example 5

The long-term success of lung transplantation continues to be challenged by the development of chronic lung allograft dysfunction (CLAD). This study investigated the relationship between cytokine expression levels in pre-implanted donor lungs and the post-transplant development of CLAD and its subtypes, bronchiolitis obliterans syndrome (BOS) and restrictive allograft syndrome (RAS). Of 109 patients who underwent bilateral lung or heart-lung transplantation and survived for more than three months, 50 BOS, 21 RAS and 38 patients with No CLAD were identified by pulmonary function test results. Using donor lung tissue biopsies sampled from each patient, expression levels of IL-6, IL-1β, IL-8, IL-10, interferon-γ and tumor necrosis factor-α mRNA were measured. IL-6 expression levels were significantly higher in pre-implanted lungs of patients that ultimately developed BOS compared to RAS and No CLAD (p=0.025 and p=0.011, respectively). Cox regression analysis demonstrated an association between high IL-6 expression levels and BOS development (hazard ratio=4.98; 95% confidence interval=2.42-10.2, p<0.001). In conclusion, high IL-6 mRNA expression levels in pre-implanted donor lungs were associated with the development of BOS, not RAS. This association further supports the contention that early graft injury impacts on both late graft function as well as early graft function.

Background

Lung transplantation is a lifesaving technique for patients with end-stage lung disease. However, despite the improvement of early survival rates in lung transplant recipients, long-term success continues to be challenged by the development of chronic lung allograft dysfunction (CLAD), which is a major cause of morbidity and mortality in long-term survivors[1].

CLAD can be considered to be the consequence of a multitude of potential injuries experienced by donor lungs pre- and post-transplantation, involving multiple immune systems[2]. Acute damage may contribute to a vicious injury-remodeling cycle in the transplanted lung allograft, which may ultimately develop CLAD via activation of stromal resident cells such as epithelial and endothelial cells as well as the formation of lymphoid-like stroma[3-5]. Specifically, acute damage to the allograft, including episodes of acute rejection[6-8], primary graft dysfunction (PGD)[9,10], cytomegalovirus (CMV) pneumonitis[11], gastroesophageal-reflux[12] and early and late new-onset diffuse alveolar damage (DAD)[13], have all been shown to increase the risk of CLAD and its subtypes. Furthermore, increasing evidence suggests that cytokines may play important roles during the development of CLAD[3,14-17]. However, it remains unclear whether CLAD development, which has previously been shown to be associated with PGD and adverse early outcomes[18-21], is associated with pre-implantation cytokine expression levels in the donor lung.

While bronchiolitis obliterans syndrome (BOS) has previously characterized the conventional form of CLAD, restrictive allograft syndrome (RAS) has recently been described as a novel CLAD subtype[13]. Because BOS and RAS show distinct clinical, radiological and pathological characteristics[13,22,23], and these CLAD phenotypes may represent biologically distinct subtypes which should therefore be assessed separately. An improved understanding of these phenotypes may help to establish more precisely targeted and personalized therapeutic strategies.

In an analysis of the expression levels of traditional inflammatory cytokine mRNAs (IL-6, IL-1β, IL-8, IL-10, interferon (IFN)-γ and tumor necrosis factor (TNF)-α) in biopsy samples from 169 pre-implantation donor lungs, the ratio of IL-6 to IL-10 in pre-implantation donor lungs was associated with 30-day mortality[20]. In this study, the same population of 169 pre-transplantation donor lungs was investigated and cytokine expression levels were compared with long-term graft outcome. Relatively higher IL-6 gene expression in pre-transplantation donor lungs is shown here to be associated with early development of BOS, and not RAS.

Materials and Methods
Study Population

A retrospective review of the medical records of 169 lung transplant recipients who were included in a previous cytokine mRNA expression profiling study[20] was completed. Designation of the study population into subgroups (BOS, RAS and No CLAD) is summarized in FIG. 10A. 122 recipients of bilateral lung or heart-lung transplantation who survived more than three months after transplantation were identified. We excluded nine patients with forced expiratory volume in one second (FEV$_1$) below 80% of baseline due to co-morbidities: eight patients were identified as having an infection and one patient was identified with lung cancer. We also excluded four patients who developed CLAD but did not have sufficient data on total lung capacity (TLC) necessary to determine CLAD phenotype. In all, 109 patients met selection criteria for further analysis.

Biopsy of Pre-Implant Donor Lungs

From 1998-2003, we prospectively collected lung graft biopsies taken from donor lungs at the end of cold ischemia treatment (just prior to implantation) in the Toronto Lung Transplant Program. All lungs were derived from donation after brain death donors. Patients consented to biopsies of the donor lung prior to implantation or to the use of the excess lung tissue in donor lungs that would be removed to accommodate the recipients. A portion of the biopsy sample was taken from the peripheral part of the donor lung using a mechanical stapler and immediately snap-frozen in liquid nitrogen and stored at −80° C. for subsequent analysis.

Measurement of Gene Expression

All biopsies were analyzed to measure expression levels of IL-6, IL-1β, IL-8, IL-10, IFN-γ and TNF-α mRNA in a blinded fashion by quantitative real-time reverse transcription polymerase chain reaction (qRT-PCR) as previously described[20]. The primers used for the amplification of cytokine mRNAs are summarized in Table 11. Briefly, each primer pair for IL-6 and IL-1β mRNA spanned an intron. The forward primer for the measurement of TNF-α mRNA was located at an exon/exon junction. The primers employed for IL-10, IL-8 and IFN-γ mRNA were located within one respective exon. Reverse transcription reaction was conducted using random hexamers. Each assay included a standard curve of five serial dilutions and a no-template negative control. All assays were performed in duplicate. The cytokine expression levels were normalized to the level of 18S ribosomal RNA.

Post-Transplant Follow-Up

After the lungs were transplanted, standard care was provided as previously described[24]. Specifically, post-transplant transbronchial lung biopsies (TBLBs) were scheduled to be collected at 2 and 6 weeks and 3, 6, 9, 12, 18 and 24 months after lung transplantation and when clinically indicated. Acute rejection in TBLB samples was evaluated by pathologists based on the International Society for Heart and Lung Transplantation (ISHLT) grading system[25].

Definition of CLAD and its Subtypes

CLAD, BOS and RAS were defined as previously described in detail[13,26]. Baseline FEV$_1$ was defined according to the criteria recommended by ISHLT[27], and baseline TLC was calculated as the average of the parameters measured at the time of the best FEV$_1$ measurements. CLAD (i.e. BOS and RAS) was defined as an irreversible decline in FEV$_1$ below 80% of baseline. BOS was strictly defined as CLAD without the restrictive changes that define RAS. RAS was defined as CLAD with an irreversible decline in TLC below 90% of baseline.

The diagnosis of CLAD was made only if functional decline persisted after appropriate treatment for infection or acute rejection, or both. The diagnosis of BOS was not made until a valid TLC measurement was collected, in order to determine the presence or absence of RAS. Early-onset BOS was defined as BOS which developed within 3 years after lung transplant as previously described[28]. Declines in FEV$_1$ and TLC were considered reproducible only when two separate measurements at least three weeks apart met the threshold for CLAD and RAS, respectively. The first date of decline in FEV$_1$ and TLC that met the criterion of each condition was recorded as the onset date. The long-term outcome of each patient was assessed based on the last valid pulmonary function test result for each time point.

Statistical Analysis

One-way analysis of variance (ANOVA), Fisher's exact test and Kruskal-Wallis test were performed to demonstrate the difference among patients with BOS, RAS and No CLAD. Mann-Whitney and Kruskal-Wallis tests were applied to examine the difference in relative cytokine mRNA expression levels between patients with CLAD and those with No CLAD, and among patients with BOS, RAS and No CLAD, respectively. A Spearman correlation test was used to determine the strength of the relationships between expression levels of cytokines and between cytokine expression levels and donor factors.

Kaplan-Meier curve estimation was applied to visually reveal the relationship between the time after lung transplant and the long-term outcome (i.e. survival and CLAD-free survival). P-values were calculated by log-rank test with Bonferroni's correction. Difference in cumulative incidence of CLAD, BOS and RAS were analyzed by Gray's test with Bonferroni's correction. In this analysis, deaths unrelated to CLAD were considered as a competing event of CLAD, BOS and RAS. Additionally, onset of RAS was considered as a competing event of BOS and vice versa. Running log-rank statistics were applied to obtain the best-fit cutoff point of the cytokine mRNA expression levels for discriminating long-term outcomes over time[29]. Patients were then divided into two groups based on whether their cytokine mRNA expression levels were above or below the cutoff point.

Consequently, Cox regression was performed to find contributing factors of long-term outcome, including cytokine expression and potential risk and confounding factors. Donor age[30] and Grade A2-4 acute rejection[6-8] were included as potential risk factors of CLAD and BOS. $PaO_2/FiO_2$ ratio below 200 mmHg on arrival in the intensive care unit (ICU) after lung transplantation was also included as a surrogate factor for Grade 3 PGD T-zero[9,10], which is defined as a combination of $PaO_2/FiO_2$ ratio below 200 mmHg and radiographic infiltration consistent with pulmonary edema within 6 hours of reperfusion[31]. Early (≤3 months) diffuse alveolar damage (DAD) was included as a potential risk factor of both CLAD and BOS, whereas late new-onset (>3 months) DAD was included as a potential risk factor of CLAD; early and late new-onset DAD have been implicated as risk factors of BOS and RAS, respectively[26]. Potential confounding factors include recipient age, primary diagnosis of recipients, donor-recipient gender combination and CMV serology combination at the time of transplant.

Values of $p<0.05$ were considered significant. GraphPad Prism 6.02 (GraphPad Software, San Diego, Calif., USA) and EZR (Saitama Medical Center, Jichi Medical University, Saitama, Japan), a modified version of R commander (the R Foundation for Statistical Computing) for Windows (Microsoft, Redmond, Wash., USA), were used to complete the analysis.

Results

Figure 10A:
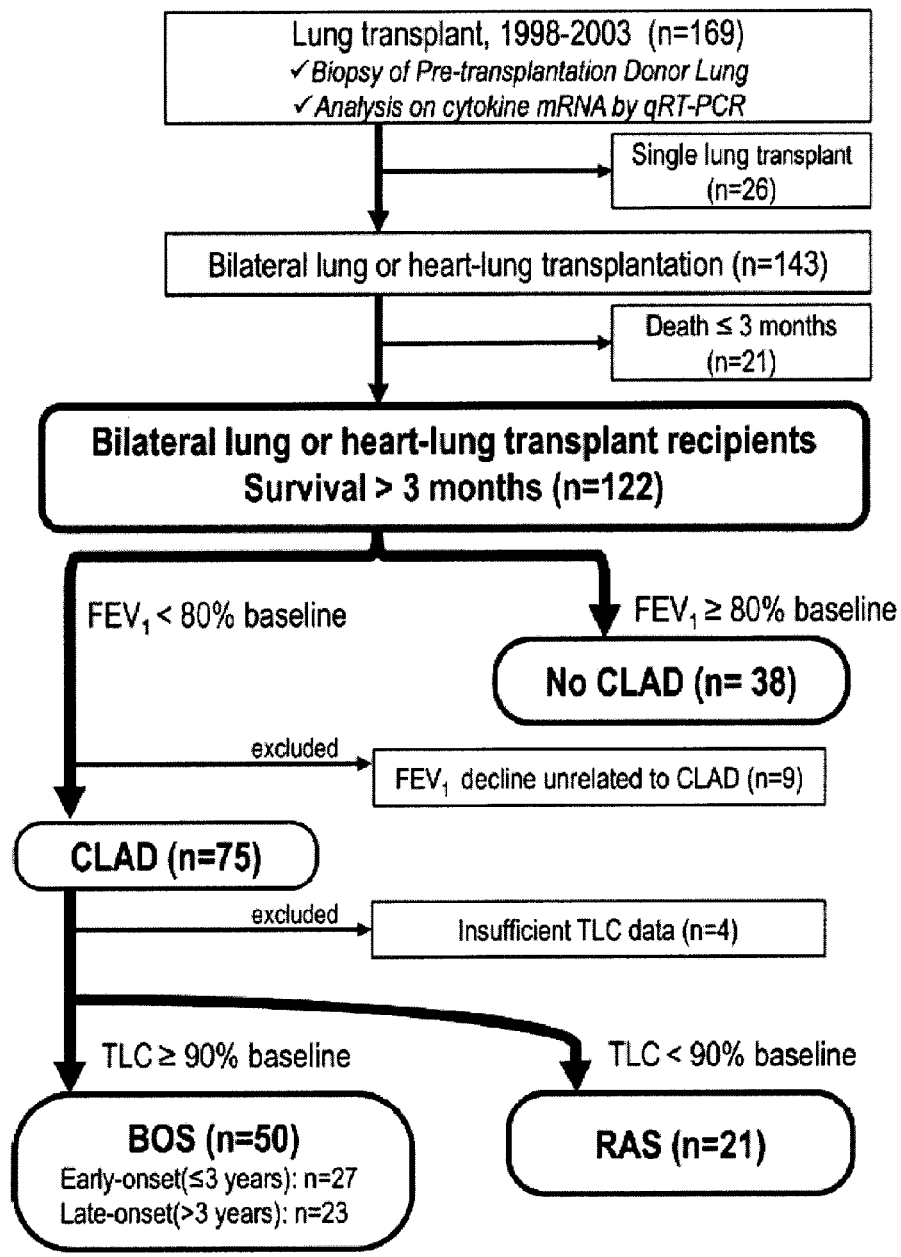
FIGS. 10A-D is a series of graphs showing an overview of the study population distribution and the long-term outcome of 109 patients.
Figure 10B:
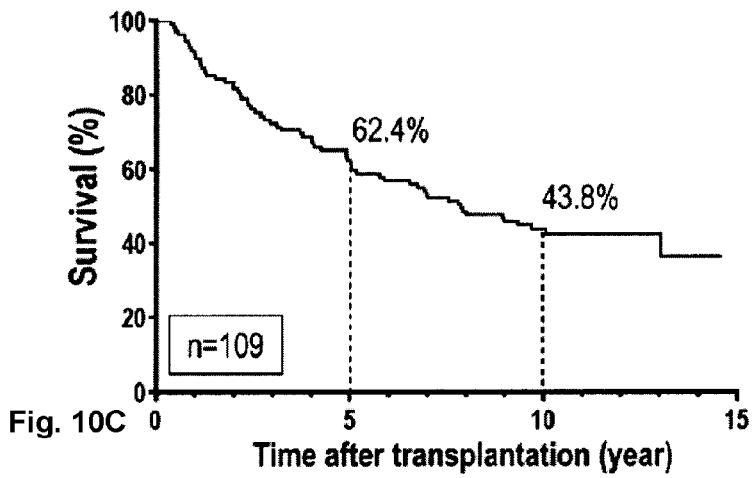
Figure 10C:
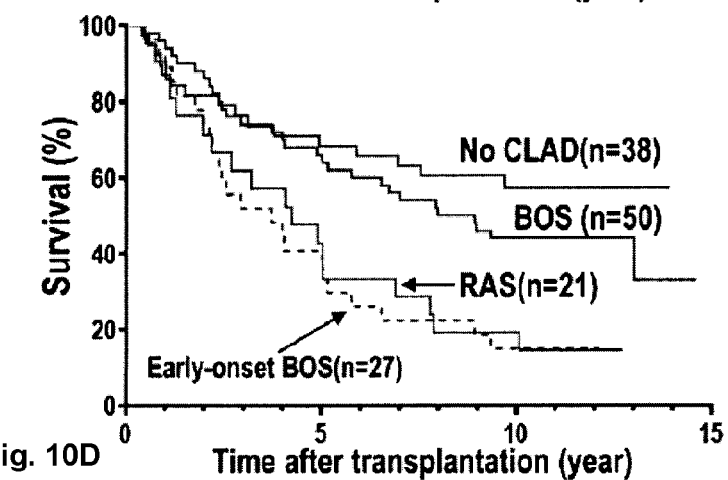
Figure 10D:
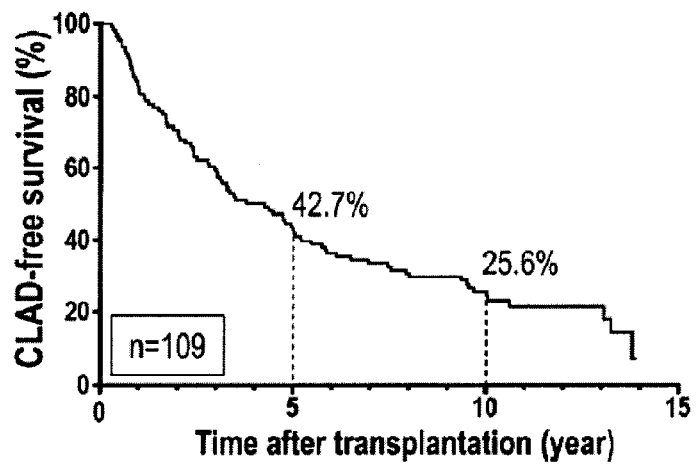

CLAD development was observed in 71 of 109 patients. Of these, 50 patients were diagnosed with BOS and 21 patients were diagnosed with RAS (FIG. 10A). Five- and ten-year survival rates were 62.4% and 43.8%, respectively (FIG. 10B). A survival curve plot of CLAD phenotypes demonstrated a five-year survival rate of 68.4% in No CLAD, 66.0% in BOS and 42.9% in RAS patients (FIG. 10C). The survival rate of RAS was significantly lower than that of No CLAD and BOS patients (adjusted p=0.008 and 0.029, respectively). Differences in survival rates between No CLAD and BOS did not reach statistical significance (adjusted p=0.795). However, early-onset BOS showed a significantly lower survival rate compared to No CLAD (adjusted p=0.005). CLAD-free survival rates were 42.7% and 25.6%, respectively (FIG. 10D).

Figure 11:
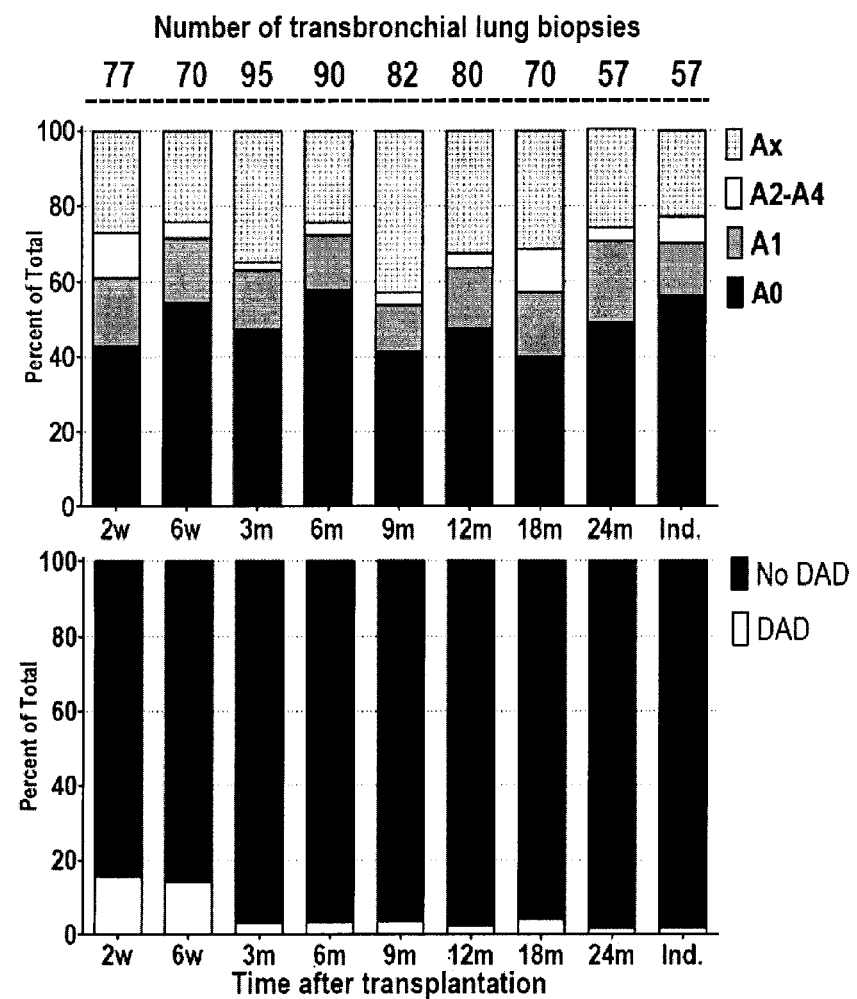
FIG. 11: Number of transbronchial lung biopsies and percentage of patients with each grade of acute rejection or presence/absence of diffuse alveolar damage according to the time of biopsy collection. Out of 109 recipients, transbronchial lung biopsies were collected from 77 cases at 2 weeks, 70 cases at 6 weeks, 95 cases at 3 months, 90 cases at 6 months, 82 cases at 9 months, 80 cases at 12 months, 70 cases at 18 months, 75 cases at 24 months and 57 cases when clinically indicated. In brief, in A2-4 cases the rate of acute rejection was 11.7% at 2 weeks, 4.3% at 6 weeks, 2.1% at 3 months, 3.3% at 6 months, 3.7% at 9 months, 3.8% at 12 months, 11.4% at 18 months, 3.5% at 24 months and 7.0$ at clinically indicated biopsy.

Clinical characteristics and postoperative findings of the 109 patients are summarized in Table 12. There was no significant difference in clinical characteristics among No CLAD, BOS or RAS groups, or between No CLAD and CLAD groups, with the exception of the duration of donor mechanical ventilation which was significantly longer only in RAS patients compared to No CLAD patients (p=0.025). There was no significant difference in $PaO_2/FiO_2$ on ICU arrival, incidence of Grade A2-4 acute rejection or early DAD among No CLAD, BOS or RAS groups or between No CLAD and CLAD patients. Late new-onset DAD was frequently observed in RAS patients (p=0.011). The number of transbronchial lung biopsies and percentage of patients with each grade of acute rejection and presence or absence of diffuse alveolar damage according to the timing of biopsies are summarized in FIG. 11.

Relative cytokine mRNA expression levels are summarized in Table 13. IL-6 had higher expression levels in the BOS group compared to No CLAD and RAS groups (p=0.011 and p=0.025, respectively). IL-6 and IL-1β were more highly expressed in CLAD vs. No CLAD (p=0.047 and 0.035, respectively), and IL-6 and IL-1β showed a high Spearman correlation coefficient (r=0.696, p<0.001). IL-8, IL-10, IFN-γ and TNF-α expression levels were not significantly different across study groups. IL-6 expression levels were weakly correlated with the duration of donor mechanical ventilation, donor age and cold ischemic time (CIT) (Spearman correlation r=−0.114, 0.122 and −0.150, respectively). IL-6 expression levels were not significantly different between genders (p=0.803), donor causes of death (i.e. cerebrovascular accident vs. head trauma, p=0.543), donor smoking histories (i.e. above vs. below 20 pack-year, p=0.982), or donor CMV serology (i.e. positive vs. negative, p=0.905).

Figure 12A:
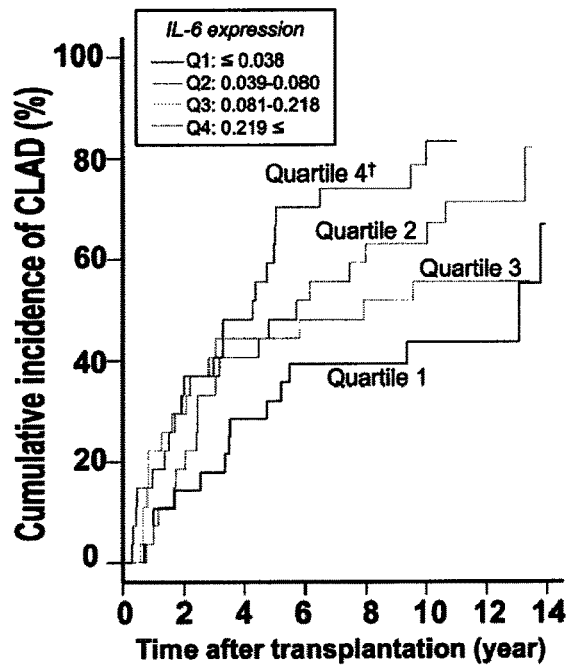
FIGS. 12A-C; is a series of panels showing the relationship between pre-implant IL-6 expression levels and development of CLAD and BOS.
Figure 12B:
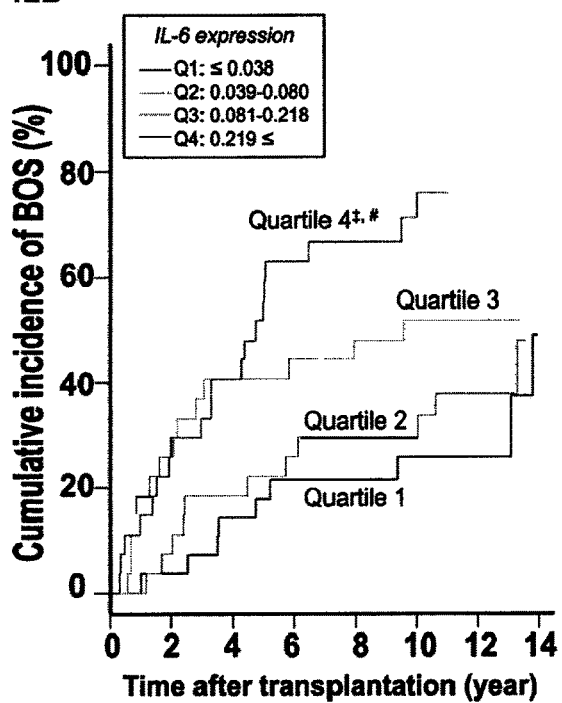
Figure 12C:
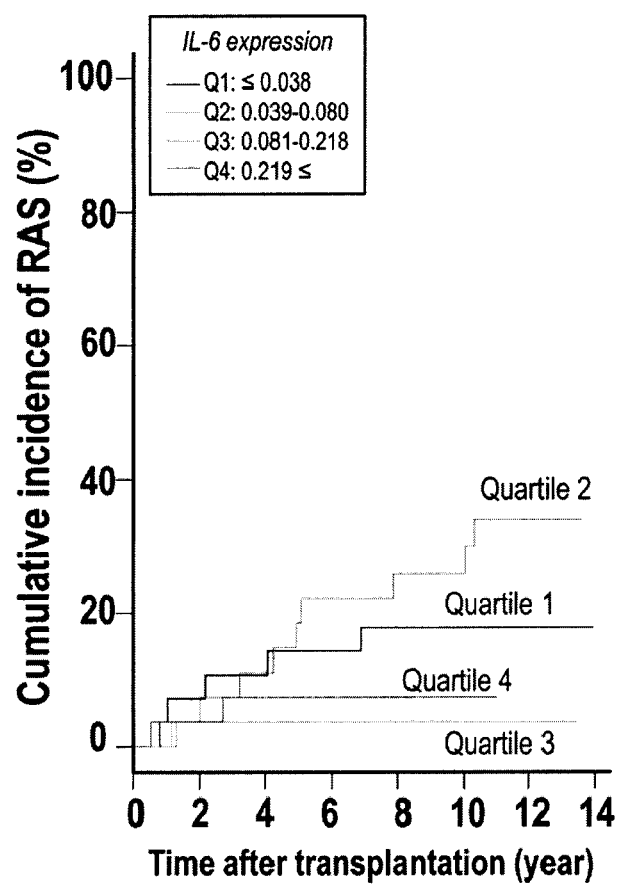
Figure 13:
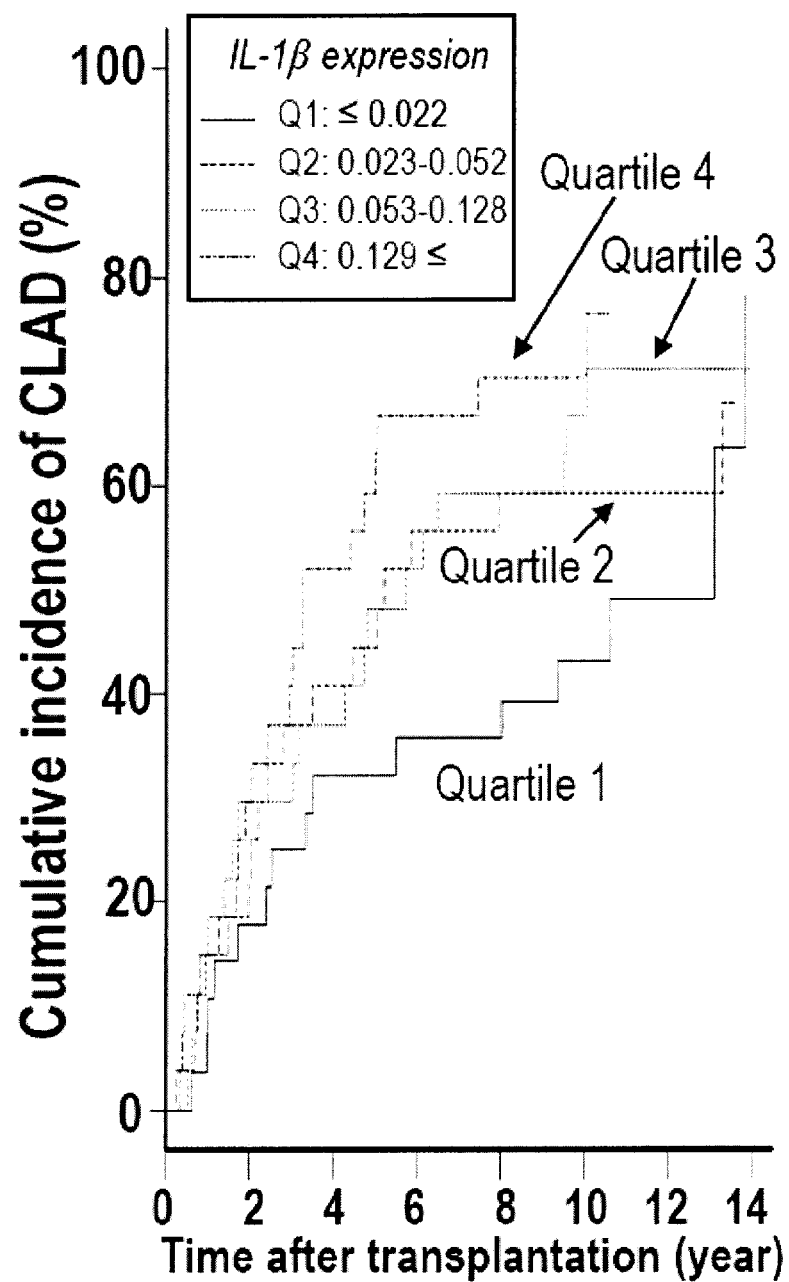
FIG. 13: Relationship between pre-transplantation IL-1β expression levels and development of CLAD and BOS. Cumulative incidence of CLAD tended to be higher in patient in the top quartile compared to those in the bottom quartile, but it did not reach statistical significance (adjusted p=0.120).

An estimation of cumulative incidence of developing CLAD, BOS and RAS according to quartiles of relative expression levels of IL-6 is shown in FIG. 12. Cumulative incidence of CLAD was higher in the top quartile compared to the bottom quartile (adjusted p=0.021, FIG. 12A). Cumulative incidence of BOS was higher in the top quartile compared to the bottom and lower middle quartile (adjusted p=0.002 and 0.016, respectively, FIG. 12B). Cumulative incidence of RAS in the lower middle quartile tended to be higher than the upper middle quartile, but it did not reach statistical significance (adjusted p=0.081, FIG. 2C). On the other hand, quartiles of IL-1β expression did not show significant difference in cumulative incidence of CLAD (FIG. 13). Based on these results, the potential role of IL-6 in CLAD and BOS development was analyzed.

Figure 14:
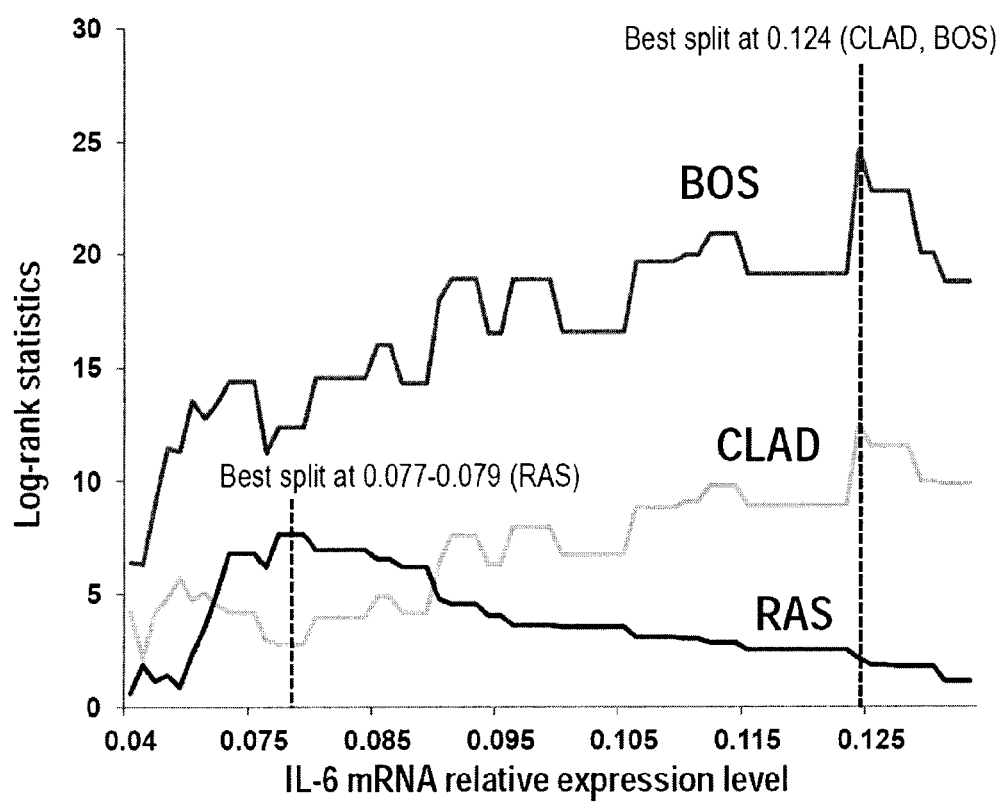
FIG. 14: Running log-rank statistics for a cutoff point of IL-6 relative expression. The maximum log-rank statistical value of developing BOS and CLAD were 24.6 and 12.5, respectively, both of which result in an optimal cutoff point for IL-6 mRNA relative expression level of 0.124. For RAS, the maximum log-rank statistical value was 7.64, with an optimal IL-6 mRNA level ranging from 0.077 to 0.079.

The maximum log-rank statistical values of developing CLAD and BOS were 12.5 and 24.6, respectively, both of which result in an optimal cutoff point for IL-6 mRNA relative expression level of 0.124 (FIG. 14).

Results from a multivariate Cox proportional-hazards regression treating acute rejection as a time-dependent covariate in relation to CLAD, BOS and early-onset BOS development is illustrated in Table 14. Development of CLAD was associated with higher levels of IL-6 mRNA expression (hazard ratio=2.56; 95% confidence interval (CI)= 1.41-4.52, p=0.001) and late new-onset DAD (hazard ratio=4.32; 95% CI=1.85-10.12.917-9.477, p<0.001). Moreover, BOS development was associated with higher IL-6 expression levels (hazard ratio=4.98; 95% CI=2.42-10.2, p<0.001). This effect was independent from $PaO_2/FiO_2$ below 200 mmHg at ICU arrival, which tended to be associated with BOS development, but did not reach statistical significance (p=0.181). Furthermore, early-onset BOS development was associated with higher IL-6 expression levels (hazard ratio=4.15; 95% CI=1.62-10.6, p=0.003) and $PaO_2/FiO_2$ below 200 mmHg at ICU arrival (hazard ratio=3.17; 95% CI=1.21-8.31, p=0.019). The effect of pretransplant high IL-6 expression was persistent when conditioning on 1-year survival (Table 15).

Discussion

CLAD is a major cause of morbidity and mortality in long-term survivors of lung transplantation. In our study population, only 42.7% of recipients were CLAD-free at five years after lung transplantation. Importantly, early-onset BOS and RAS showed negative impact on post-transplant survival, which is compatible with previous reports[13,23,28] (FIG. 10C). The establishment of effective preventive or therapeutic strategies for CLAD is essential to improve long-term outcomes of patients undergoing lung transplantation. Although accumulating evidence suggests that cytokines may play pivotal roles in the development of CLAD[3,14-17], the impact of cytokine expression in pre-implantation donor lung has yet to be elucidated. Herein, it is demonstrated that higher IL-6 relative expression levels are associated with the development of BOS.

Intriguingly, relative expression levels of IL-6 in pre-implantation donor lungs were significantly higher in patients who eventually developed BOS compared to patients who developed RAS or no CLAD (Table 13). Furthermore, it is demonstrated that higher relative expression levels of IL-6 in pre-implantation donor lungs were associated with the development of CLAD, BOS and early-onset BOS (Table 14). This effect seemed persistent over time and was independent from the $PaO_2/FiO_2$ ratio at ICU arrival, which is a major determinant for the classification of PGD T-zero severity[31].

IL-6 is a pleiotropic 21-kD glycoprotein that regulates immune response, inflammation, hematopoiesis, metabolism and regeneration. Unlike many other cytokines, IL-6 could be produced not only by immune responsive cells, but also by non-hematopoietic cells such as lung epithelial cells upon various stimuli[32].

It is increasingly suggested that IL-6 expression might be carefully controlled by posttranscriptional as well as transcriptional levels: whereas nuclear factor-kappa B and CCAAT enhancer binding protein β have been identified as important transcriptional regulators of IL-6 expression, the ribonuclease Regnase-1 has recently been shown to prevent autoimmunity by destabilizing IL-6 mRNA that could be counteracted by AT-rich interactive domain-containing protein 5A[33,34]. Therefore, IL-6 mRNA levels that could be measured by qRT-PCR would reflect IL-6 activity.

It has been recognized that IL-6 is an active regulator of immune response. For example, IL-6 orchestrates chemokine-directed leukocyte trafficking by modulating activation of resident tissue cells and controlling the immunological switch from innate to adaptive immunity through regulating leukocyte activation, differentiation and proliferation[35,36]. Moreover, IL-6, in combination with transforming growth factor β, has been shown to serve as a regulator of the effector fate of CD4+ T cells, inducing IL-17-producing T helper ($T_H17$) cell differentiation and suppressing regulatory T (Treg) cell differentiation[35,37]. IL-17 has been implicated in the triggering of a positive feedback loop through increased IL-6 expression and also plays a role in alloantibody and autoantibody production and in obliterative fibrosis of the airways[38,39]. Importantly, dysregulation of IL-6 may play a pivotal role in autoimmune response, as overproduction of IL-6 has been observed in several autoimmune and chronic inflammatory diseases, such as rheumatoid arthritis and juvenile idiopathic arthritis[37,36]. Through the examination of lungs affected by CLAD, we have previously demonstrated the formation of lymphoid-like stroma and activation of stromal resident cells, which would also develop autoimmune/chronic inflammatory diseases[3,4,40]. Interestingly, in a mouse model of bronchiolitis obliterans, Nakagiri and colleagues demonstrated that IL-6-producing lymphocytes and endothelium, with local increase in $T_H17$ in the allograft, showed airway obliteration[16]. Moreover, the lack of graft-producing IL-6 significantly prolonged allograft survival with reduced alloantibody production and/or increased intragraft Treg population in a mouse model of renal transplantation[41]. Additionally, several reports have indicated the association between IL-6 and the development of CLAD[42-44]. Collectively, upregulation of IL-6 in pre-implant donor lung may contribute to the development of CLAD—especially BOS—by promoting an autoimmune response and persistent chronic inflammation.

No single donor factor could be identified that may determine IL-6 expression levels in the donor lung. Expression levels of IL-6 were highly correlated with that of IL-1β. Both IL-6 and IL-1β production have been shown to be stimulated by the activation of toll-like receptors (TLRs), which then triggers an innate immune response[45,46]. IL-6 and IL-1β mRNA expression levels in pre-transplant donor lungs might be attributed to a multitude of various injurious events that could be recognized by TLRs.

Interestingly, IL-1β was upregulated in the CLAD group compared to the No CLAD group, although quartiles of IL-1β expression levels did not show a significant difference in the cumulative incidence of CLAD (Table 13 and FIG. 13). Since IL-1β has been shown to mediate innate immunity, which could likely be activated by many of the identified risk factors of CLAD including PGD, CMV pneumonitis and gastroesophageal-reflux[2], upregulated IL-1β in the pre-transplant donor lung may play a role in the development of CLAD by mediating the innate immune response.

From a therapeutic and preventive point of view, IL-6 blockade, neutralization or attenuation could be potential strategies to prevent BOS. Intriguingly, Nakagiri and colleagues demonstrated IL-6 neutralization could attenuate airway obliteration and IL-17 mRNA expression in a mouse model of obliterative bronchiolitis[16]. Encouragingly, we have found that adenoviral IL-10 gene therapy under normothermic ex vivo lung perfusion attenuated both IL-6 and IL-1β production in lung tissue after four hours of reperfusion in a large-animal lung transplant model[47,48]. This could be explored as a potential therapeutic pre-transplant intervention to prevent BOS.

In contrast to BOS, patients who developed RAS showed lower relative expression levels of IL-6 compared to those who developed BOS, which may indicate that RAS development may not be associated with pre-implant IL-6 upregulation and that biological distinctions may exist between BOS and RAS. Further investigation is necessary to identify biologic characteristics of pre-transplant donor lungs that eventually develop RAS.

It was confirmed $PaO_2/FiO_2$ values below 200 mmHg at ICU arrival as an independent risk factor of early-onset BOS, whereas A2-4 acute rejection could not be identified as a significant risk factor of CLAD or BOS in the multivariate analysis. This might be attributed to the relatively low incidence of A2-4 acute rejection in the cohort compared to previous reports[8,49] (Table 12 and FIG. 11). This finding might be partly due to our study population inclusion criteria, which excluded 21 subjects with early mortality and 9 patients with $FEV_1$ decline unrelated to CLAD, potentially hindering our statistical ability to evaluate casual risk factors such as A2-4 acute rejection. Another factor may also be inadequate sampling and inter-observer variability in the pathologic grading of acute rejection. Arcasoy and colleagues reported that the consensus pathologic panel confirmed the original center pathologists' diagnosis in 49.1% of A0, 21.1% of A1 and 53.5% of A2-4 cases[50]. Nevertheless, we cannot deny the possibility of underestimating the impact of A2-4 acute rejection in this study.

Potential risk factors of CLAD, such as post-transplant CMV infection, gastroesophageal reflux, pre-transplant HLA sensitization or de novo donor-specific antigen, were not assessed. The study was initiated before the current ISHLT PGD severity scoring system was made available, and $PaO_2/FiO_2$ values at ICU arrival were employed as a surrogate variable to reflect the severity of PGD at T-zero. Finally, the interpretation of this study is limited to donation after brain death (DBD) lungs. Recently, it has been reported that the cumulative incidence of CLAD was 7% in 72 recipients of donation after cardiac death (DCD) lungs with a median follow-up of 477 days[51]. Long-term outcomes of DCD lung transplantation might be linked to the relatively less inflammatory nature of DCD lungs, which have shown lower pre-transplant IL-6 expression levels compared to DBD lungs[52].

TABLE 11

Primers used for amplification of cytokines and 18S Ribosomal RNA.

| Gene | Forward Primer (5'-3') | SEQ ID NO. | Reverse primer (5'-3') | SEQ ID NO. | Note for primer design |
|---|---|---|---|---|---|
| IL-6 | CACACAGACAGCCACTCACC | 1 | TTTTCTGCCAGTGCCTCTTT | 2 | Spanning an intron |
| IL-1β | GGACAAGCTGAGGAAGATGC | 3 | TCGTTATCCCATGTGTCGAA | 4 | Spanning an intron |
| IL-8 | CAGGAATTGAATGGGTTTGC | 5 | AGCAGACTAGGGTTGCCAGA | 6 | Within an exon |
| IL-10 | AAGCCTGACCACGCTTTCTA | 7 | GCTCCCTGGTTTCTCTTCCT | 8 | Within an exon |
| IFN-γ | GTCCAACGCAAAGCAATACA | 9 | ATATTGCAGGCAGGACAACC | 10 | Within an exon |
| TNF-α | AGCCCATGTTGTAGCAAACC | 11 | TGAGGTACAGGCCCTCTGAT | 12 | Exon/exon junction (forward primer) |
| 18S ribosomal RNA | GTAACCCGTTGAACCCCATT | 13 | CCATCCAATCGGTAGTAGCG | 14 | — |

INF, interferon; TNF, tumor necrosis factor.

TABLE 12

Demographics of 109 lung transplant patients

| | No CLAD (n = 38) | BOS (n = 50) | RAS (n = 21) | CLAD (n = 71) | Three subgroups p-value | No CLAD vs. CLAD p-value |
|---|---|---|---|---|---|---|
| Pretransplant characteristics | | | | | | |
| Follow-up period, year | 9.7 [3.1-11.2] | 8.4 [2.8-10.8] | 4.2 [1.6-7.8] | 6.7 [2.4-10.3] | 0.058 | 0.262 |
| Donor age, year | 41.1 ± 15.7 | 43.6 ± 14.9 | 38.2 ± 16.8 | 42.0 ± 15.7 | 0.941 | 0.753 |
| Recipient age, year | 43.8 ± 15.6 | 44.3 ± 14.9 | 45.4 ± 14.3 | 44.6 ± 14.6 | 0.843 | 0.769 |
| Donor smoking, (%) | | | | | | |
| ≤20 pack-year | 28 (73.7%) | 39 (78.0%) | 11 (52.4%) | 50 (70.4%) | 0.106 | 0.825 |
| >20 pack-year | 10 (26.3%) | 11 (22.0%) | 10 (47.6%) | 21 (29.6%) | — | — |
| Donor mechanical ventilation, h | 33.7 [27.0-49.6] | 45.0 [31.3-71.8] | 52.5 [34.4-126.5]* | 46.4 [32.0-.72.8] | 0.032 | 0.021 |
| Donor cause of death, (%) | | | | | | |
| Cerebrovascular accident | 21 (55.3%) | 29 (58.0%) | 12 (57.1%) | 41 (57.7%) | 0.920 | 1.000 |
| Head trauma | 12 (31.6%) | 17 (34.0%) | 5 (23.8%) | 22 (31.0%) | — | — |
| Others | 5 (13.2%) | 4 (8.0%) | 4 (19.0%) | 8 (11.3%) | — | — |
| CIT (first lung), min | 196 [144-241] | 193 [152-242] | 193 [155-279] | 193 [153-244] | 0.894 | 0.989 |
| Primary diagnosis, (%) | | | | | | |
| IPF | 9 (23.7%) | 8 (16.0%) | 5 (23.8%) | 13 (18.3%) | 0.575 | 0.208 |
| COPD | 6 (15.8%) | 13 (26.0%) | 9 (42.9%) | 22 (31.0%) | — | — |
| Cystic fibrosis | 11 (28.9%) | 13 (26.0%) | 5 (23.8%) | 18 (25.4%) | — | — |
| PAH | 1 (2.6%) | 3 (6.0%) | 1 (4.8%) | 4 (5.6%) | — | — |
| α-1 antitrypsin deficiency | 4 (10.5%) | 2 (4.0%) | — | 2 (2.8%) | — | — |
| Others | 7 (18.4%) | 11 (22.0%) | 1 (4.8%) | 12 (16.9%) | — | — |

TABLE 12-continued

Demographics of 109 lung transplant patients

|  | No CLAD (n = 38) | BOS (n = 50) | RAS (n = 21) | CLAD (n = 71) | Three subgroups p-value | No CLAD vs. CLAD p-value |
|---|---|---|---|---|---|---|
| Transplant type, (%) |  |  |  |  |  |  |
| Bilateral lung | 37 (97.4%) | 49 (98.0%) | 21 | 70 (98.6%) | — | — |
| Heart-lung | 1 (2.6%) | 1 (2.0%) | — | 1 (1.4%) | — | — |
| Gender matching, (%) |  |  |  |  |  |  |
| Male to male | 21 (55.3%) | 19 (38.0%) | 9 (42.9%) | 28 (39.4%) | 0.444 | 0.228 |
| Male to female | 1 (2.6%) | 6 (12.0%) | 3 (14.3%) | 9 (12.7%) | — | — |
| Female to female | 10 (26.3%) | 18 (36.0%) | 5 (23.8%) | 23 (32.4%) | — | — |
| Female to male | 6 (15.8%) | 7 (14.0%) | 4 (19.0%) | 11 (15.5%) | — | — |
| CMV serology matching, (%) |  |  |  |  |  |  |
| Donor−/recipient− | 12 (31.6%) | 11 (22.0%) | 3 (14.3%) | 14 (19.7%) | 0.136 | 0.487 |
| Donor−/recipient+ | 11 (28.9%) | 14 (28.0%) | 5 (23.8%) | 19 (26.8%) | — | — |
| Donor+/recipient+ | 10 (26.3%) | 20 (40.0%) | 5 (23.8%) | 25 (35.2%) | — | — |
| Donor+/recipient− | 5 (13.2%) | 5 (10.0%) | 8 (38.0%) | 13 (18.3%) | — | — |
| Posttransplant findings |  |  |  |  |  |  |
| $PaO_2/FiO_2$ at ICU arrival | 398 [234-467] | 389 [266-476] | 415 [305-496] | 394 [296-481] | 0.684 | 0.513 |
| Acute rejection |  |  |  |  |  |  |
| Only A0 or A1 | 29/36[1] (80.6%) | 33/49[1] (67.3%) | 14/20[1] (70.0%) | 47/69[1] (68.1%) | 0.444 | 0.250 |
| A2-4 | 7/36[1] (19.4%) | 16/49[1] (32.7%) | 6/20[1] (30.0%) | 22/69[1] (31.9%) | — | — |
| Diffuse alveolar damage |  |  |  |  |  |  |
| Early onset (≤3 months) | 3/34[1] (7.9%) | 13/44[1] (29.5%) | 4/20[1] (19.0%) | 16/64[1] (22.5%) | 0.110 | 0.064 |
| Late new-onset (>3 months) | 2/34[1] (5.3%) | 4/44[1] (8.0%) | 7/20[1] (33.3%)**, *** | 11/64[1] (15.5%) | 0.011 | 0.209 |

ANOVA, analysis of variance; BOS, bronchiolitis obliterans syndrome; CIT, cold ischemic time; CLAD, chronic lung allograft dysfunction; CMV, cytomegalovirus; COPD, chronic obstructive pulmonary disease; ICU, intensive care unit; IPF, idiopathic pulmonary fibrosis; PAH, pulmonary arterial hypertension; RAS, restrictive allograft syndrome.
Parametric continuous variables are expressed as mean ± standard deviation. Nonparametric continuous variables are expressed as median (interquartile range).
p-Values were calculated using Fisher's exact test for categorical variables. One-way ANOVA and Student's t-test were used for parametric continuous variables to determine p-values for three subgroups (i.e. among No CLAD, BOS and RAS) and for No CLAD vs. CLAD, respectively. Kruskal-Wallis ANOVA test and Mann-Whitney test were applied for nonparametric continuous variables to determine p-value for the three subgroups and for No CLAD vs. CLAD, respectively.
*$p < 0.05$ in RAS vs. No CLAD.
**$p < 0.01$ in RAS vs. No CLAD.
***$p < 0.05$ in RAS vs. BOS.
[1]Only patients who received at least one biopsy were included.

TABLE 13

Relative expression levels of the key cytokines

| | Median (IQR) | | | | Three subgroups | |
|---|---|---|---|---|---|---|
| mRNA | No CLAD (n = 38) | BOS (n = 50) | RAS (n = 21) | CLAD (n = 71) | (Kruskal-Wallis ANOVA) p-value | No CLAD vs. CLAD p-value |
| IL-6 | 0.059 (0.021-0.115) | 0.138*, ** (0.062-0.275) | 0.058 (0.024-0.075) | 0.090 (0.043-0.248) | 0.0035 | 0.047 |
| IL-1β | 0.030 (0.017-0.099) | 0.066 (0.034-0.166) | 0.075 (0.015-0.137) | 0.070 (0.025-0.155) | 0.078 | 0.035 |
| IL-8 | 0.103 (0.032-0.254) | 0.152 (0.074-0.349) | 0.135 (0.080-0.249) | 0.153 (0.083-0.403) | 0.289 | 0.145 |
| IL-10 | 1.428 (0.749-3.821) | 1.457 (0.753-4.245) | 1.980 (0.791-9.720) | 1.560 (0.769-4.386) | 0.695 | 0.998 |
| IFN-γ | 2.492 (1.102-6.696) | 2.333 (0.751-.8.937) | 3.025 (0.977-13.72) | 2.809 (0.755-10.19) | 0.731 | 0.967 |
| TNF-α | 0.363 (0.146-0.476) | 0.425 (0.262-0.583) | 0.314 (0.222-0.601) | 0.401 (0.238-0.599) | 0.195 | 0.081 |

ANOVA, analysis of variance; BOS, bronchiolitis obliterans syndrome; CLAD, chronic lung allograft dysfunction; IFN, interferon; RAS, restrictive allograft syndrome; IQR, interquartile range; TNF, tumor necrosis factor.
Relative cytokine expression levels were normalized to the expression levels of 18S ribosomal RNA.
Kruskal-Wallis ANOVA test and Mann-Whitney test were applied to determine p-value for three subgroups (i.e. among No CLAD, BOS and RAS) and for No CLAD vs. CLAD, respectively. Steel-Dwass multiple comparison test was used as a post hoc test to determine p-values for BOS vs. No CLAD, RAS vs. No CLAD and BOS vs. RAS.
*$p = 0.011$ in BOS vs. No CLAD.
**$p = 0.025$ in BOS vs. RAS.

TABLE 14

The resurts of Cox regression model treating acute rejection as a time-dependent covariate

|  | CLAD | | | BOS | | | Early BOS (≤3 years) | | |
|---|---|---|---|---|---|---|---|---|---|
| Factors | HR | 95% CI | p Value | HR | 95% CI | p Value | HR | 95% CI | p-Value |
| Donor age at transplant[1] | 0.944 | 0.788-1.12 | 0.504 | 1.01 | 0.830-1.23 | 0.911 | 1.10 | 0.836-1.45 | 0.486 |
| Recipient age at transplant[1] | 1.00 | 0.972-1.03 | 0.993 | 1.01 | 0.976-1.04 | 0.696 | 1.02 | 0.977-1.07 | 0.341 |

TABLE 14-continued

The resurts of Cox regression model treating acute rejection as a time-dependent covariate

| Factors | CLAD | | | BOS | | | Early BOS (≤3 years) | | |
|---|---|---|---|---|---|---|---|---|---|
| | HR | 95% CI | p Value | HR | 95% CI | p Value | HR | 95% CI | p-Value |
| Primary diagnosis | | | | | | | | | |
| IPF | 1 | — | 0.625 | 1 | — | 0.777 | 1 | — | 0.925 |
| COPD | 1.92 | 0.746-4.96 | — | 1.84 | 0.569-5.92 | — | 0.991 | 0.246-4.00 | — |
| Cystic fibrosis | 1.26 | 0.362-4.42 | — | 2.62 | 0.590-11.7 | — | 2.16 | 0.326-14.3 | — |
| PAH | 1.99 | 0.250-3.92 | — | 2.89 | 0.610-13.7 | — | 2.80 | 0.224-35.1 | — |
| α-1 antitrypsin deficiency | 0.756 | 0.137-4.17 | — | 2.74 | 0.430-17.5 | — | — | — | — |
| Gender matching | | | | | | | | | |
| Male to male | 1 | — | 0.131 | 1 | — | 0.880 | 1 | — | 0.589 |
| Male to female | 2.55 | 1.09-5.97 | — | 1.40 | 0.504-3.86 | — | 1.24 | 0.350-4.38 | — |
| Female to female | 1.62 | 0.814-3.22 | — | 1.12 | 0.498-2.50 | — | 0.729 | 0.209-2.54 | — |
| Female to male | 1.07 | 0.423-2.68 | — | 0.858 | 0.278-2.65 | — | 0.296 | 0.048-1.83 | — |
| CMV serology matching | | | | | | | | | |
| Donor−/recipient− | 1 | — | 0.155 | 1 | — | 0.282 | 1 | — | 0.177 |
| Donor−/recipient+ | 1.05 | 0.482-2.29 | — | 1.48 | 0.589-3.74 | — | 1.18 | 0.270-5.14 | — |
| Donor+/recipient+ | 1.88 | 0.820-4.31 | — | 2.46 | 0.950-6.38 | — | 3.38 | 0.832-13.8 | — |
| Donor+/recipient− | 2.05 | 0.875-4.80 | — | 1.15 | 0.394-3.37 | — | 1.06 | 0.227-4.99 | — |
| Early DAD (≤3 months) | | | | | | | | | |
| Early DAD (−) | 1 | — | 0.133 | 1 | — | 0.137 | 1 | — | 0.579 |
| Early DAD (+) | 1.65 | 0.860-3.15 | — | 1.80 | 0833-3.80 | — | 1.39 | 0.434-4.45 | — |
| Late new-onset DAD (>3 months) | | | | | | | | | |
| Late new-onset DAD (−) | 1 | — | <0.001 | — | — | — | — | — | — |
| Late new-onset DAD (+) | 4.32 | 1.85-10.1 | — | — | — | — | — | — | — |
| Acute rejection | | | | | | | | | |
| Only A0 or A1 | 1 | — | 0.476 | 1 | — | 0.544 | 1 | — | 0.343 |
| A2-4 | 1.2 | 0.675-2.32 | — | 1.25 | 0.610-2.55 | — | 1.64 | 0.589-4.57 | — |
| PaO$_2$/FiO$_2$ at ICU arrival | | | | | | | | | |
| PaO$_2$/FiO$_2$ ≥ 200 mmHg | 1 | — | 0.963 | 1 | — | 0.181 | 1 | — | 0.019 |
| PaO$_2$/FiO$_2$ < 200 mmHg | 1.02 | 0.481-2.15 | — | 1.74 | 0.771-3.94 | — | 3.17 | 1.21-8.31 | — |
| Pretransplantation IL-6 mRNA | | | | | | | | | |
| Relatively lower: IL-6 ≤ 0.124 | 1 | — | 0.001 | 1 | — | <0.001 | 1 | — | 0.003 |
| Relatively higher: IL-6 > 0.124 | 2.56 | 1.41-4.52 | — | 4.98 | 2.42-10.2 | — | 4.15 | 1.62-10.6 | — |

Note.
that late new-onset DAD was included only in analysis on CLAD (i.e. BOS and RAS), as the previous report suggested late new-onset DAD could be a potential risk factor of RAS, not BOS.
BOS, bronchiolitis obliterans syndrome; CI, confidence interval; CLAD, chronic lung allograft dysfunction; COPD, chronic obstructive pulmonary disease; CMV, cytomegalovirus; DAD, diffuse alveolar damage; HR, hazard ratio; ICU, intensive care unit; IPF, idiopathic pulmonary fibrosis; PAH, pulmonary arterial hypertension; RAS, restrictive allograft syndrome.
[1]The hazard ratio indicates the change by an increase of donor or recipient age at transplant by 10.

TABLE 15

The results of Cox regression model treating acute rejection as a time-dependent covariate conditioned on 1-year survival.

| Factors | CLAD | | | BOS | | | Early BOS (≤3 years) | | |
|---|---|---|---|---|---|---|---|---|---|
| | HR | 95% CI | p-value | HR | 95% CI | p-value | HR | 95% CI | p-value |
| Donor age at transplant* | 1.01 | 0.834-1.23 | 0.916 | 1.01 | 0.823-1.25 | 0.893 | 1.10 | 0.807-1.49 | 0.560 |
| Recipient age at transplant* | 0.997 | 0.968-1.03 | 0.825 | 1.00 | 0.973-1.04 | 0.814 | 1.02 | 0.974-1.07 | 0.401 |
| Primary diagnosis | | | | | | | | | |
| IPF | 1 | — | 0.752 | 1 | — | 0.759 | 1 | — | 0.888 |
| COPD | 1.78 | 0.663-4.79 | | 1.80 | 0.527-6.17 | | 1.02 | 0.229-5.64 | |
| Cystic fibrosis | 1.04 | 0.288-3.77 | | 2.79 | 0.595-13.1 | | 2.53 | 0.360-4.54 | |
| PAH | 1.00 | 0.249-4.02 | | 3.01 | 0.615-14.7 | | 3.08 | 0.233-17.9 | |
| α-1 antitrypsin deficiency | 0.691 | 0.120-3.97 | | 2.88 | 0.448-18.6 | | — | — | |
| Gender matching | | | | | | | | | |
| Male to Male | 1 | — | 0.090 | 1 | — | 0.880 | 1 | — | 0.517 |
| Male to Female | 2.53 | 1.03-6.23 | | 1.24 | 0.412-3.74 | | 1.07 | 0.261-4.40 | |

TABLE 15-continued

The results of Cox regression model treating acute rejection as a time-dependent covariate conditioned on 1-year survival.

| Factors | CLAD | | | BOS | | | Early BOS (≤3 years) | | |
|---|---|---|---|---|---|---|---|---|---|
| | HR | 95% CI | p-value | HR | 95% CI | p-value | HR | 95% CI | p-value |
| Female to Female | 1.89 | 0.926-3.87 | | 1.26 | 0.554-2.85 | | 0.906 | 0.262-3.13 | |
| Female to Male | 1.01 | 0.381-2.66 | | 0.768 | 0.236-2.50 | | 0.185 | 0.019-1.80 | |
| CMV serology matching | | | | | | | | | |
| Donor−/Recipient− | 1 | — | 0.137 | 1 | — | 0.442 | 1 | — | 0.278 |
| Donor−/Recipient+ | 0.940 | 0.420-2.10 | | 1.42 | 0.553-3.62 | | 1.06 | 0.213-4.75 | |
| Donor+/Recipient+ | 1.52 | 0.652-3.52 | | 2.21 | 0.838-5.80 | | 3.01 | 0.719-12.6 | |
| Donor+/Recipient− | 2.29 | 0.965-5.43 | | 1.26 | 0.429-3.68 | | 1.30 | 0.280-6.03 | |
| Early DAD (≤3 mo) | | | | | | | | | |
| Early DAD (−) | 1 | — | 0.136 | 1 | — | 0.137 | 1 | — | 0.740 |
| Early DAD (+) | 1.66 | 0.852- 3.25 | | 1.73 | 0.793-3.75 | | 1.24 | 0.353-4.33 | |
| Late new-onset DAD (>3 mo) | | | | | | | | | |
| Late new-onset DAD (−) | 1 | — | 0.003 | — | — | — | — | — | — |
| Late new-onset DAD (+) | 4.13 | 1.64-10.4 | | | | | | | |
| Acute rejection | | | | | | | | | |
| Only A0 or A1 | 1 | — | 0.476 | 1 | — | 0.469 | 1 | — | 0.490 |
| A2-4 | 1.25 | 0.675-2.32 | | 1.31 | 0.633-2.71 | | 1.45 | 0.508-4.11 | |
| $PaO_2/FiO_2$ at ICU arrival | | | | | | | | | |
| $PaO_2/FiO_2$ ≥ 200 mmHg | 1 | — | 0.485 | 1 | — | 0.828 | 1 | — | 0.274 |
| $PaO_2/FiO_2$ < 200 mmHg | 0.742 | 0.321-1.71 | | 1.11 | 0.434-2.84 | | 1.86 | 0.613-5.82 | |
| Pre-transplantation IL-6 mRNA | | | | | | | | | |
| Relatively lower: IL-6 ≤ 0.124 | 1 | — | 0.008 | 1 | — | <0.001 | 1 | — | 0.007 |
| Relatively higher: IL-6 > 0.124 | 2.25 | 1.23-4.12 | | 4.93 | 2.32-10.5 | | 3.79 | 1.44-9.97 | |

*The hazard ratio indicates the change by an increase of donor or recipient age at transplant by 10.
Note
that late new-onset DAD was included only in analysis on CLAD (i.e. BOS and RAS), as the previous report suggested late new-onset DAD could be a potential risk factor of RAS, not BOS.
CI, confidence interval; CLAD, chronic lung allograft dysfunction; COPD, chronic obstructive pulmonary disease; CMV, cytomegaloviris; DAD, diffuse alveolar damage; HR, hazard ratio; ICU, intensive care unit; IPF, idiopathic pulmonary fibrosis; PAH, pulmonary arterial hypertension.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Specifically, the sequences associated with each accession numbers provided herein including for example accession numbers and/or biomarker sequences (e.g. protein and/or nucleic acid) provided in the Tables or elsewhere, are incorporated by reference in its entirely.

CITATIONS FOR REFERENCES REFERRED TO IN THE SPECIFICATION

1. Christie J D, Edwards L B, Kucheryavaya A Y, Benden C, Dipchand A I, Dobbels F, Kirk R, Rahmel A O, Stehlik J, Hertz M I. The registry of the international society for heart and lung transplantation: 29th adult lung and heart-lung transplant report-2012. *J Heart Lung Transplant* 2012; 31:1073-86.
2. Sato M, Keshavjee S. Bronchiolitis Obliterans Syndrome: Alloimmune-Dependent and -Independent Injury with Aberrant Tissue Remodeling. *Seminars in Thoracic and Cardiovascular Surgery* 2008; 20:173-82.
3. Sato M. Chronic lung allograft dysfunction after lung transplantation: the moving target. *General Thoracic and Cardiovascular Surgery* 2012.
4. Sato M, Hirayama S, Matsuda Y, Wagnetz D, Hwang D M, Guan Z, Liu M, Keshavjee S. Stromal Activation and Formation of Lymphoid-Like Stroma in Chronic Lung Allograft Dysfunction. *Transplantation* 2011; 92:1398-405.
5. Wagnez D S M, Yeung J, Hirayama S, Waddell T, Liu M, Keshavjee S. De novo formation of lymphoid tissue in the lung evolves post transplant obliterative airway. *J Heart Lung Transplant* 2010; 29(2):S109.
6. Meloni F, Vitulo P, Cascina A, Oggionni T, Bulgheroni A, Paschetto E, Klersy C, D'Armini A M, Fietta A, Bianco A M, Arbustini E, Vigano M. Bronchoalveolar lavage cytokine profile in a cohort of lung transplant recipients: a predictive role of interleukin-12 with respect to onset of bronchiolitis obliterans syndrome. *J Heart Lung Transplant* 2004; 23:1053-60.
7. Vos R, Vanaudenaerde B M, De Vleeschauwer S I, Willems-Widyastuti A, Scheers H, Van Raemdonck D E, Dupont L J, Verleden G M. Circulating and intrapulmonary C-reactive protein: a predictor of bronchiolitis obliterans syndrome and pulmonary allograft outcome. *J Heart Lung Transplant* 2009; 28:799-807.
8. Neujahr D C, Perez S D, Mohammed A, Ulukpo O, Lawrence E C, Fernandez F, Pickens A, Force S D, Song M, Larsen C P, Kirk A D. Cumulative Exposure to Gamma Interferon-Dependent Chemokines CXCL9 and CXCL10 Correlates with Worse Outcome After Lung Transplant. *Am J Transplant* 2012; 12:438-46.

9. Gilpin S E, Lung K C, Sato M, Singer L G, Keshavjee S, Waddell T K. Altered progenitor cell and cytokine profiles in bronchiolitis obliterans syndrome. *J Heart Lung Transplant* 2012; 31:222-8.
10. Ofek E, Sato M, Saito T, Wagnetz U, Roberts H C, Chaparro C, Waddell T K, Singer L G, Hutcheon M A, Keshavjee S, Hwang D M. Restrictive allograft syndrome post lung transplantation is characterized by pleuroparenchymal fibroelastosis. *Mod Pathol* 2012.
11. Sato M, Waddell T K, Wagnetz U, Roberts H C, Hwang D M, Haroon A, Wagnetz D, Chaparro C, Singer L G, Hutcheon M A, Keshavjee S. Restrictive allograft syndrome (RAS): A novel form of chronic lung allograft dysfunction. *J Heart Lung Transplant* 2011; 30:735-42.
12. Rozen S, Skaletsky H. Primer3 on the WWW for general users and for biologist programmers. *Methods Mol Biol* 2000; 132:365-86.
13. Sato M, Hwang D M, Ohmori-Matsuda K, Chaparro C, Waddell T K, Singer L G, Hutcheon M A, Keshavjee S. Revisiting the pathologic finding of diffuse alveolar damage after lung transplantation. *J Heart Lung Transplant* 2012.
14. Estenne M, Maurer J R, Boehler A, Egan J J, Frost A, Hertz M, Mallory G B, Snell G I, Yousem S. Bronchiolitis obliterans syndrome 2001: an update of the diagnostic criteria. *J Heart Lung Transplant* 2002; 21:297-310.
15. Yeung J C, Keshavjee S, Liu M. The Role of Toll-Like Receptors in Lung Transplantation. In: Greene C M, ed. Toll-Like Receptors in Diseases of the Lung: Bentham Science; 2012:151-62.
16. Manicassamy S, Pulendran B. Modulation of adaptive immunity with Toll-like receptors. *Semin Immunol* 2009; 21:185-93.
17. Andrade C F, Waddell T K, Keshavjee S, Liu M. Innate immunity and organ transplantation: the potential role of toll-like receptors. *Am J Transplant* 2005; 5:969-75.
18. Kosanam H, Sato M, Batruch I, Smith C, Keshavjee S, Liu M, Diamandis E P. Differential proteomic analysis of bronchoalveolar lavage fluid from lung transplant patients with and without chronic graft dysfunction. *Clin Biochem* 2012; 45:223-30.
19. Konen E, Weisbrod G L, Pakhale S, Chung T, Paul N S, Hutcheon M A. Fibrosis of the upper lobes: a newly identified late-onset complication after lung transplantation? *AJR Am J Roentgenol* 2003; 181(6):1539-43.
20. Choi Y W, Rossi S E, Palmer S M, DeLong D, Erasmus J J, McAdams H P. Bronchiolitis obliterans syndrome in lung transplant recipients: correlation of computed tomography findings with bronchiolitis obliterans syndrome stage. J Thorac Imaginge 2003; 18(2):72-9.
21. Sato M, Hwang D M, Ohmori-Madsuda K, Chaparro C, Waddell T K, Singer L G, Hutcheon M A, Keshavjee S. Revisiting the pathologic finding of diffuse alveolar damage after lung transplantation. *J Heart Lung Transplant* 2012; 31(4):354-63.

REFERENCES FROM EXAMPLE 4

1. Organ Procurement and Transplantation Network and Scientific Registry of Transplant Recipients 2010 data report. *Am J Transplant* 2012; 12:1-156.
2. Ofek E, Sato M, Saito T, Wagnetz U, Roberts H C, Chaparro C, Waddell T K, Singer L G, Hutcheon M A, Keshavjee S, Hwang D M. Restrictive allograft syndrome post lung transplantation is characterized by pleuroparenchymal fibroelastosis. *Mod Pathol* 2013; 26:350-6.
3. Sato M, Waddell T K, Wagnetz U, Roberts H C, Hwang D M, Haroon A, Wagnetz D, Chaparro C, Singer L G, Hutcheon M A, Keshavjee S. Restrictive allograft syndrome (RAS): A novel form of chronic lung allograft dysfunction. J Heart Lung Transplant 2011; 30:735-42.
4. Todd J L, Palmer S M. Bronchiolitis obliterans syndrome: the final frontier for lung transplantation. *Chest* 2011; 140:502-8.
5. Kastelijn E A, van Moorsel C H, Rijkers G T, Ruven H J, Karthaus V, Kwakkel-van Erp J M, van de Graaf E A, Zanen P, van Kessel D A, Grutters J C, van den Bosch J M. Polymorphisms in innate immunity genes associated with development of bronchiolitis obliterans after lung transplantation. *J Heart Lung Transplant* 2010; 29:665-71.
6. Guo W A, Knight P R, Raghavendran K. The receptor for advanced glycation end products and acute lung injury/acute respiratory distress syndrome. *Intensive Care Med* 2012; 38:1588-98.
7. Chan J K, Roth J, Oppenheim J J, Tracey K J, Vogl T, Feldmann M, Horwood N, Nanchahal J. Alarmins: awaiting a clinical response. *J Clin Invest* 2012; 122:2711-9.
8. Kosanam H, Sato M, Batruch I, Smith C, Keshavjee S, Liu M, Diamandis E P. Differential proteomic analysis of bronchoalveolar lavage fluid from lung transplant patients with and without chronic graft dysfunction. Clin Biochem 2012; 45:223-30.
9. Husain S, Mooney M L, Danziger-Isakov L, Mattner F, Singh N, Avery R, Ison M, Humar A, Padera R F, Lawler L P, Fisher A, Drew R J, Gould K F, Sole A, Studer S, Munoz P, Singer L G, Hannan M. A 2010 working formulation for the standardization of definitions of infections in cardiothoracic transplant recipients. *J Heart Lung Transplant* 2011; 30:361-74.
10. de Perrot M, Chaparro C, McRae K, Waddell T K, Hadjiliadis D, Singer L G, Pierre A F, Hutcheon M, Keshavjee S. Twenty-year experience of lung transplantation at a single center: Influence of recipient diagnosis on long-term survival. *J Thorac Cardiovasc Surg* 2004; 127:1493-501.
11. D'Ovidio F, Mura M, Ridsdale R, Takahashi H, Waddell T K, Hutcheon M, Hadjiliadis D, Singer L G, Pierre A, Chaparro C, Gutierrez C, Miller L, Darling G, Liu M, Post M, Keshavjee S. The effect of reflux and bile acid aspiration on the lung allograft and its surfactant and innate immunity molecules SP-A and SP-D. *Am J Transplant* 2006; 6:1930-8.
12. Stewart S, Fishbein M C, Snell G I, Berry G J, Boehler A, Burke M M, Glanville A, Gould F K, Magro C, Marboe C C, McNeil K D, Reed E F, Reinsmoen N L, Scott J P, Studer S M, Tazelaar H D, Wallwork J L, Westall G, Zamora M R, Zeevi A, Yousem S A. Revision of the 1996 working formulation for the standardization of nomenclature in the diagnosis of lung rejection. *J Heart Lung Transplant* 2007; 26:1229-42.
13. Sato M, Hwang D M, Waddell T K, Singer L G, Keshavjee S. Progression pattern of restrictive allograft syndrome after lung transplantation. J Heart Lung Transplant 2013; 32:23-30.
14. Estenne M, Maurer J R, Boehler A, Egan J J, Frost A, Hertz M, Mallory G B, Snell G I, Yousem S. Bronchiolitis obliterans syndrome 2001: an update of the diagnostic criteria. J Heart Lung Transplant 2002; 21:297-310.
15. Meyer K C, Glanville A R. Bronchiolitis Obliterans Syndrome and Chronic Lung Allograft Dysfunction:

Evolving Concepts and Nomenclature. In: Bronchiolitis Obliterans Syndrome in Lung Transplantation: Springer; 2013:1-19.

16. Snell G I, Paraskeva M, Westall G P. Managing Bronchiolitis Obliterans Syndrome (BOS) and Chronic Lung Allograft Dysfunction (CLAD) in Children: What Does the Future Hold? *Paediatr Drugs* 2013; 15:281-9.

17. Verleden S E, Ruttens D, Vandermeulen E, Vaneylen A, Dupont L J, Van Raemdonck D E, Verleden G M, Vanaudenaerde B M, Vos R. Bronchiolitis Obliterans Syndrome and Restrictive Allograft Syndrome: Do Risk Factors Differ? *Transplantation* 2013; 95:1167-72.

18. Kennedy V E, Todd J L, Palmer S M. Bronchoalveolar Lavage as a Tool to Predict, Diagnose and Understand Bronchiolitis Obliterans Syndrome. *Am J Transplant* 2013; 13:552-61.

19. Wittkowski H, Sturrock A, van Zoelen M A, Viemann D, van der Poll T, Hoidal J R, Roth J, Foell D. Neutrophil-derived S100A12 in acute lung injury and respiratory distress syndrome. *Crit Care Med* 2007; 35:1369-75.

20. Korthagen N M, Nagtegaal M M, van Moorsel C H, Kazemier K M, van den Bosch J M, Grutters J C. MRP14 is elevated in the bronchoalveolar lavage fluid of fibrosing interstitial lung diseases. *Clin Exp Immunol* 2010; 161: 342-7.

21. Jiang H, Hu H, Tong X, Jiang Q, Zhu H, Zhang S. Calcium-binding protein S100P and cancer: mechanisms and clinical relevance. *J Cancer Res Clin Oncol* 2012; 138:1-9.

22. Li G, Liang X, Lotze M T. HMGB1: The Central Cytokine for All Lymphoid Cells. *Front Immunol* 2013; 4:68.

23. Nakagiri T, Inoue M, Morii E, Minami M, Sawabata N, Utsumi T, Kadota Y, Ideguchi K, Tokunaga T, Okumura M. Local IL-17 production and a decrease in peripheral blood regulatory T cells in an animal model of bronchiolitis obliterans. *Transplantation* 2010; 89:1312-9.

24. Kruger B, Yin N, Zhang N, Yadav A, Coward W, Lal G, Zang W, P S H, Bromberg J S, Murphy B, Schroppel B. Islet-expressed TLR2 and TLR4 sense injury and mediate early graft failure after transplantation. *Eur J Immunol* 2010; 40:2914-24.

25. Ueno H, Matsuda T, Hashimoto S, Amaya F, Kitamura Y, Tanaka M, Kobayashi A, Maruyama I, Yamada S, Hasegawa N, Soejima J, Koh H, Ishizaka A. Contributions of high mobility group box protein in experimental and clinical acute lung injury. *Am J Respir Crit Care Med* 2004; 170:1310-6.

26. Uchida T, Shirasawa M, Ware L B, Kojima K, Hata Y, Makita K, Mednick G, Matthay Z A, Matthay M A. Receptor for advanced glycation end-products is a marker of type I cell injury in acute lung injury. *Am J Respir Crit Care Med* 2006; 173:1008-15.

27. Van Crombruggen K, Holtappels G, De Ruyck N, Derycke L, Tomassen P, Bachert C. RAGE processing in chronic airway conditions: involvement of *Staphylococcus aureus* and ECP. *J Allergy Clin Immunol* 2012; 129:1515-21 e8.

28. Bargagli E, Madioni C, Prasse A, Fossi A, Filippi R, Bianchi N, Voltolini L, Muller-Quernheim J, Rottoli P. Eosinophilic cationic protein in bronchoalveolar lavage fluid of lung transplant patients. *Clin Chem Lab Med* 2008; 46:563-4.

REFERENCES FROM EXAMPLE 5

1. Christie J D, Edwards L B, Kucheryavaya A Y, Benden C, Dipchand A I, Dobbels F, Kirk R, Rahmel A O, Stehlik J, Hertz M I. The registry of the international society for heart and lung transplantation: 29th adult lung and heart-lung transplant report-2012. *J Heart Lung Transplant* 2012; 31:1073-86.

2. Todd J L, Palmer S M. Bronchiolitis obliterans syndrome: the final frontier for lung transplantation. *Chest* 2011; 140:502-8.

3. Sato M, Hirayama S, Matsuda Y, Wagnetz D, Hwang D M, Guan Z, Liu M, Keshavjee S. Stromal Activation and Formation of Lymphoid-Like Stroma in Chronic Lung Allograft Dysfunction. *Transplantation* 2011; 92:1398-405.

4. Sato M, Hirayama S, Hwang D M, Lara-Guerra H, Wagnetz D, Waddell T K, Liu M, Keshavjee S. The Role of Intrapulmonary De Novo Lymphoid Tissue in Obliterative Bronchiolitis after Lung Transplantation. *The Journal of Immunology* 2009; 182:7307-16.

5. Sato M, Keshavjee S. Bronchiolitis Obliterans Syndrome: Alloimmune-Dependent and -Independent Injury with Aberrant Tissue Remodeling. *Seminars in Thoracic and Cardiovascular Surgery* 2008; 20:173-82.

6. Sharples L D, McNeil K, Stewart S, Wallwork J. Risk factors for bronchiolitis obliterans: a systematic review of recent publications. *J Heart Lung Transplant* 2002; 21:271-81.

7. Burton C M, Iversen M, Carlsen J, Mortensen J, Andersen C B, Steinbruchel D, Scheike T. Acute cellular rejection is a risk factor for bronchiolitis obliterans syndrome independent of post-transplant baseline FEV1. *J Heart Lung Transplant* 2009; 28:888-93.

8. Khalifa A P, Hachem R R, Chakinala M M, Yusen R D, Aloush A, Patterson G A, Mohanakumar T, Trulock E P, Walter M J. Minimal acute rejection after lung transplantation: a risk for bronchiolitis obliterans syndrome. *Am J Transplant* 2005; 5:2022-30.

9. Huang H J, Yusen R D, Meyers B F, Walter M J, Mohanakumar T, Patterson G A, Trulock E P, Hachem R R. Late primary graft dysfunction after lung transplantation and bronchiolitis obliterans syndrome. *Am J Transplant* 2008; 8:2454-62.

10. Daud S A, Yusen R D, Meyers B F, Chakinala M M, Walter M J, Aloush A A, Patterson G A, Trulock E P, Hachem R R. Impact of immediate primary lung allograft dysfunction on bronchiolitis obliterans syndrome. *Am J Respir Crit Care Med* 2007; 175:507-13.

11. Kroshus T J, Kshettry V R, Savik K, John R, Hertz M I, Bolman R M, 3rd. Risk factors for the development of bronchiolitis obliterans syndrome after lung transplantation. *J Thorac Cardiovasc Surg* 1997; 114:195-202.

12. D'Ovidio F, Mura M, Ridsdale R, Takahashi H, Waddell T K, Hutcheon M, Hadjiliadis D, Singer L G, Pierre A, Chaparro C, Gutierrez C, Miller L, Darling G, Liu M, Post M, Keshavjee S. The effect of reflux and bile acid aspiration on the lung allograft and its surfactant and innate immunity molecules SP-A and SP-D. *Am J Transplant* 2006; 6:1930-8.

13. Sato M, Waddell T K, Wagnetz U, Roberts H C, Hwang D M, Haroon A, Wagnetz D, Chaparro C, Singer L G, Hutcheon M A, Keshavjee S. Restrictive allograft syndrome (RAS): A novel form of chronic lung allograft dysfunction. *J Heart Lung Transplant* 2011; 30:735-42.

14. Neujahr D C, Perez S D, Mohammed A, Ulukpo O, Lawrence E C, Fernandez F, Pickens A, Force S D, Song M, Larsen C P, Kirk A D. Cumulative Exposure to Gamma Interferon-Dependent Chemokines CXCL9 and CXCL10 Correlates with Worse Outcome After Lung Transplant. *Am J Transplant* 2012; 12:438-46.

15. Gilpin S E, Lung K C, Sato M, Singer L G, Keshavjee S, Waddell T K. Altered progenitor cell and cytokine profiles in bronchiolitis obliterans syndrome. *J Heart Lung Transplant* 2012; 31:222-8.
16. Nakagiri T, Inoue M, Morii E, Minami M, Sawabata N, Utsumi T, Kadota Y, Ideguchi K, Tokunaga T, Okumura M. Local IL-17 production and a decrease in peripheral blood regulatory T cells in an animal model of bronchiolitis obliterans. *Transplantation* 2010; 89:1312-9.
17. Vanaudenaerde B M, De Vleeschauwer S I, Vos R, Meyts I, Bullens D M, Reynders V, Wuyts W A, Van Raemdonck D E, Dupont L J, Verleden G M. The role of the IL23/IL17 axis in bronchiolitis obliterans syndrome after lung transplantation. *Am J Transplant* 2008; 8:1911-20.
18. Cypel M, Yeung J C, Liu M, Anraku M, Chen F, Karolak W, Sato M, Laratta J, Azad S, Madonik M, Chow C W, Chaparro C, Hutcheon M, Singer L G, Slutsky A S, Yasufuku K, de Perrot M, Pierre A F, Waddell T K, Keshavjee S. Normothermic ex vivo lung perfusion in clinical lung transplantation. *N Engl J Med* 2011; 364:1431-40.
19. Anraku M, Cameron M J, Waddell T K, Liu M, Arenovich T, Sato M, Cypel M, Pierre A F, de Perrot M, Kelvin D J, Keshavjee S. Impact of Human Donor Lung Gene Expression Profiles on Survival after Lung Transplantation: A Case-Control Study. *Am J Transplant* 2008; 8:2140-8.
20. Kaneda H, Waddell T K, de Perrot M, Bai X H, Gutierrez C, Arenovich T, Chaparro C, Liu M, Keshavjee S. Pre-Implantation Multiple Cytokine mRNA Expression Analysis of Donor Lung Grafts Predicts Survival After Lung Transplantation in Humans. *Am J Transplant* 2006; 6:544-51.
21. De Perrot M, Sekine Y, Fischer S, Waddell T K, McRae K, Liu M, Wigle D A, Keshavjee S. Interleukin-8 release during early reperfusion predicts graft function in human lung transplantation. *Am J Respir Crit Care Med* 2002; 165:211-5.
22. Ofek E, Sato M, Saito T, Wagnetz U, Roberts H C, Chaparro C, Waddell T K, Singer L G, Hutcheon M A, Keshavjee S, Hwang D M. Restrictive allograft syndrome post lung transplantation is characterized by pleuroparenchymal fibroelastosis. *Mod Pathol* 2012.
23. Verleden G M, Vos R, Verleden S E, De Wever W, De Vleeschauwer S I, Willems-Widyastuti A, Scheers H, Dupont L J, Van Raemdonck D E, Vanaudenaerde B M. Survival determinants in lung transplant patients with chronic allograft dysfunction. *Transplantation* 2011; 92:703-8.
24. de Perrot M, Chaparro C, McRae K, Waddell T K, Hadjiliadis D, Singer L G, Pierre A F, Hutcheon M, Keshavjee S. Twenty-year experience of lung transplantation at a single center: Influence of recipient diagnosis on long-term survival. *J Thorac Cardiovasc Surg* 2004; 127:1493-501.
25. Stewart S, Fishbein M C, Snell G I, Berry G J, Boehler A, Burke M M, Glanville A, Gould F K, Magro C, Marboe C C, McNeil K D, Reed E F, Reinsmoen N L, Scott J P, Studer S M, Tazelaar H D, Wallwork J L, Westall G, Zamora M R, Zeevi A, Yousem S A. Revision of the 1996 working formulation for the standardization of nomenclature in the diagnosis of lung rejection. *J Heart Lung Transplant* 2007; 26:1229-42.
26. Sato M, Hwang D M, Ohmori-Matsuda K, Chaparro C, Waddell T K, Singer L G, Hutcheon M A, Keshavjee S. Revisiting the pathologic finding of diffuse alveolar damage after lung transplantation. *J Heart Lung Transplant* 2012.
27. Estenne M, Maurer J R, Boehler A, Egan J J, Frost A, Hertz M, Mallory G B, Snell G I, Yousem S. Bronchiolitis obliterans syndrome 2001: an update of the diagnostic criteria. *J Heart Lung Transplant* 2002; 21:297-310.
28. Sato M, Ohmori-Matsuda K, Saito T, Matsuda Y, Hwang D M, Waddell T K, Singer L G, Keshavjee S. Time-dependent changes in the risk of death in pure bronchiolitis obliterans syndrome (BOS). *J Heart Lung Transplant* 2013.
29. Crowley J, LeBlanc M, Jacobson J, Salmon S. Some Exploratory Tools for Survival Analysis. In: Lecture Notes in Statistics Proceedings of the First Seattle Symposium in Biostatistics. New York: Springer; 1997:199-229.
30. Hennessy S A, Hranjec T, Swenson B R, Kozower B D, Jones D R, Ailawadi G, Kron I L, Lau C L. Donor Factors Are Associated With Bronchiolitis Obliterans Syndrome After Lung Transplantation. *Ann Thorac Surg* 2010; 89:1555-62.
31. Christie J, Carby M, Bag R, Corris P, Hertz M, Weill D. Report of the ISHLT Working Group on Primary Lung Graft Dysfunction Part II: Definition. A Consensus Statement of the International Society for Heart and Lung Transplantation. *J Heart Lung Transplant* 2005; 24:1454-9.
32. Neveu W A, Bernardo E, Allard J L, Nagaleekar V, Wargo M J, Davis R J, Iwakura Y, Whittaker L A, Rincon M. Fungal allergen beta-glucans trigger p38 mitogen-activated protein kinase-mediated IL-6 translation in lung epithelial cells. *Am J Respir Cell Mol Biol* 2011; 45:1133-41.
33. Masuda K, Ripley B, Nishimura R, Mino T, Takeuchi O, Shioi G, Kiyonari H, Kishimoto T. Arid5a controls IL-6 mRNA stability, which contributes to elevation of IL-6 level in vivo. *Proc Natl Acad Sci USA* 2013; 110:9409-14.
34. Matsushita K, Takeuchi O, Standley D M, Kumagai Y, Kawagoe T, Miyake T, Satoh T, Kato H, Tsujimura T, Nakamura H, Akira S. Zc3h12a is an RNase essential for controlling immune responses by regulating mRNA decay. *Nature* 2009; 458:1185-90.
35. Jones S A, Scheller J, Rose-John S. Therapeutic strategies for the clinical blockade of IL-6/gp130 signaling. *J Clin Invest* 2011; 121:3375-83.
36. Tanaka T, Narazaki M, Kishimoto T. Therapeutic targeting of the interleukin-6 receptor. *Annu Rev Pharmacol Toxicol* 2012; 52:199-219.
37. Kishimoto T. IL-6: from its discovery to clinical applications. *Int Immunol* 2010; 22:347-52.
38. Ogura H, Murakami M, Okuyama Y, Tsuruoka M, Kitabayashi C, Kanamoto M, Nishihara M, Iwakura Y, Hirano T. Interleukin-17 promotes autoimmunity by triggering a positive-feedback loop via interleukin-6 induction. *Immunity* 2008; 29:628-36.
39. Weber D J, Wilkes D S. The role of autoimmunity in obliterative bronchiolitis after lung transplantation. *Am J Physiol Lung Cell Mol Physiol* 2013; 304:L307-11.
40. Aloisi F, Pujol-Borrell R. Lymphoid neogenesis in chronic inflammatory diseases. *Nat Rev Immunol* 2006; 6:205-17.
41. Wang H, Guan Q, Lan Z, Li S, Ge W, Chen H, Nguan C Y, Du C. Prolonged renal allograft survival by donor interleukin-6 deficiency: association with decreased alloantibodies and increased intragraft T regulatory cells. *Am J Physiol Renal Physiol* 2012; 302:F276-83.

42. Hall D J, Baz M, Daniels M J, Staples E D, Klodell C T, Moldawer L L, Beaver T M. Immediate postoperative inflammatory response predicts long-term outcome in lung-transplant recipients. *Interact Cardiovasc Thorac Surg* 2012; 15:603-7.
43. Lu K C, Jaramillo A, Lecha R L, Schuessler R B, Aloush A, Trulock E P, Mendeloff E N, Huddleston C B, Alexander Patterson G, Mohanakumar T. Interleukin-6 and interferon-gamma gene polymorphisms in the development of bronchiolitis obliterans syndrome after lung transplantation. *Transplantation* 2002; 74:1297-302.
44. Scholma J, Slebos D J, Boezen H M, van den Berg J W, van der Bij W, de Boer W J, Koeter G H, Timens W, Kauffman H F, Postma D S. Eosinophilic granulocytes and interleukin-6 level in bronchoalveolar lavage fluid are associated with the development of obliterative bronchiolitis after lung transplantation. *Am J Respir Crit Care Med* 2000; 162:2221-5.
45. Opitz B, van Laak V, Eitel J, Suttorp N. Innate immune recognition in infectious and noninfectious diseases of the lung. *Am J Respir Crit Care Med* 2010; 181:1294-309.
46. Tawara K, Oxford J T, Jorcyk C L. Clinical significance of interleukin (IL)-6 in cancer metastasis to bone: potential of anti-IL-6 therapies. *Cancer Manag Res* 2011; 3:177-89.
47. Yeung J C, Wagnetz D, Cypel M, Rubacha M, Koike T, Chun Y M, Hu J, Waddell T K, Hwang D M, Liu M, Keshavjee S. Ex Vivo Adenoviral Vector Gene Delivery Results in Decreased Vector-associated Inflammation Pre- and Post-lung Transplantation in the Pig. *Mol Ther* 2012.
48. Cypel M, Liu M, Rubacha M, Yeung J C, Hirayama S, Anraku M, Sato M, Medin J, Davidson B L, de Perrot M, Waddell T K, Slutsky A S, Keshavjee S. Functional Repair of Human Donor Lungs by IL-10 Gene Therapy. *Science Translational Medicine* 2009; 1:4ra9-4ra9.
49. Burton C M, Iversen M, Scheike T, Carlsen J, Andersen C B. Minimal acute cellular rejection remains prevalent up to 2 years after lung transplantation: a retrospective analysis of 2697 transbronchial biopsies. *Transplantation* 2008; 85:547-53.
50. Arcasoy S M, Berry G, Marboe C C, Tazelaar H D, Zamora M R, Wolters H J, Fang K C, Keshavjee S. Pathologic interpretation of transbronchial biopsy for acute rejection of lung allograft is highly variable. *Am J Transplant* 2011; 11:320-8.
51. Levvey B J, Harkess M, Hopkins P, Chambers D, Merry C, Glanville A R, Snell G I. Excellent clinical outcomes from a national donation-after-determination-of-cardiac-death lung transplant collaborative. *Am J Transplant* 2012; 12:2406-13.
52. Kang C H, Anraku M, Cypel M, Sato M, Yeung J, Gharib S A, Pierre A F, de Perrot M, Waddell T K, Liu M, Keshavjee S. Transcriptional signatures in donor lungs from donation after cardiac death vs after brain death: a functional pathway analysis. *J Heart Lung Transplant* 2011; 30:289-98.

The invention claimed is:

1. A method for assaying a donor lung for bronchiolitis obliterans syndrome (BOS) subtype and/or restrictive allograft syndrome (RAS) subtype of chronic allograft lung dysfunction (CLAD) or risk of developing BOS subtype and/or RAS subtype CLAD in a recipient post-transplant, the method comprising:
   a) obtaining a bronchoalveolar lavage (BAL) fluid sample from the recipient post-transplant;
   b) treating the BAL fluid sample with a protease inhibitor;
   c) determining a normalized expression level of one or more of S100A8 and S100A9 polypeptide expression product(s) in the BAL sample;
   d) assessing the likelihood of the donor lung developing BOS subtype CLAD or RAS subtype CLAD in the recipient post-transplant based on said S100A8 and S100A9 polypeptide expression level(s); wherein an increased S100A8, level compared to a control indicates RAS or BOS subtype CLAD or an increased likelihood of developing RAS or BOS subtype CLAD in the recipient post-transplant, and an increased S100A9 or polypeptide expression level compared to a control, indicates RAS subtype CLAD or an increased likelihood of developing RAS subtype CLAD in the recipient post-transplant; and
   e) initiating therapeutic and/or preventative treatment when the recipient is labelled as having an increase in S100A8 and/or S100A9 compared to the control, wherein the therapeutic and/or preventative treatment is an immunosuppressant and/or anti-bacterial treatment.

2. The method of claim 1, wherein the assessing step further comprises assessing one or more of diffuse alveolar damage (DAD), acute rejection CMV mismatch and late new onset DAD.

3. The method of claim 1, wherein the level of S100A9 identifying the donor lung as having or having an increased likelihood of developing RAS subtype CLAD is at least 6 ng/mL, 10 ng/mL, 12, ng/mL, 14 ng/mL, 16 ng/mL, 18 ng/mL, 20 ng/mL, 22 ng/mL, 24 ng/mL, 26 ng/mL, 28 ng/mL, 30 ng/mL, 32 ng/mL, 34 ng/mL, 36 ng/mL, 38 ng/mL, 40 ng/mL, 42 ng/mL, 44 ng/mL, 46 ng/mL, 48 ng/mL, 50 ng/mL, 52 ng/mL, 54 ng/mL, 56 ng/mL or 58 ng/mL; wherein the level of S100A8 identifying the donor lung as having or having an increased likelihood of developing BOS subtype CLAD is greater than about 20 ng/mL, 22 ng/mL, 24 ng/mL, 26 ng/mL, 28 ng/mL, 30 ng/mL, 32 ng/mL, 34 ng/mL, 36 ng/mL, 38 ng/mL, 40 ng/mL, and less than about 200 ng/mL; and/or wherein the level of S100A8 identifying the donor lung as having or having an increased likelihood of developing RAS subtype CLAD is greater than about 200 ng/mL.

4. The method of claim 1, wherein the level of S100A8 identifying the donor lung as having or having an increased likelihood of developing RAS subtype CLAD is greater than about 200 ng/mL.

5. The method of claim 1, wherein the level of polypeptide expression product is measured by immunoassay.

6. The method of claim 5, wherein the immunoassay is an ELISA.

7. The method of claim 1, wherein the immunosuppressant treatment comprises tacrolimus and/or the antibacterial treatment comprises azithromycin.

8. The method of claim 1, wherein the level of S100A8 identifying the donor lung as having or having an increased likelihood of developing RAS subtype CLAD is at least 20, at least 25, at least 30 times increased compared to a CLAD threshold, above which is indicative CLAD and below which is indicative of no CLAD.

9. The method of claim 1, wherein determining a normalized expression level comprises for each of the one or more of S100A8 and S100A9, contacting the protease treated BAL fluid sample with an antibody specific for the one or more of S100A8 and S100A9 and creating a biomarker: antibody complex normalizing the amount of biomarker antibody complex to obtain the normalized expression level.

10. The method of claim 1, wherein the normalized expression level determined is for S100A8.

11. The method of claim 1, wherein the normalized expression level determined is for S100A9.

12. The method of claim 1, wherein the normalized expression level is for S100A8 and S100A9.

* * * * *